(12) United States Patent
Bilodeau et al.

(10) Patent No.: US 8,829,196 B2
(45) Date of Patent: Sep. 9, 2014

(54) TRPA1 ANTAGONISTS

(75) Inventors: Mark T. Bilodeau, Landsdale, PA (US);
Melissa Egbertson, Ambler, PA (US);
Ahren Green, Landsale, PA (US); John C. Hartnett, Philadelphia, PA (US);
Yiwei Li, Lower Gwynedd, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 153 days.

(21) Appl. No.: 13/499,844

(22) PCT Filed: Sep. 28, 2010

(86) PCT No.: PCT/US2010/050493
§ 371 (c)(1),
(2), (4) Date: Apr. 2, 2012

(87) PCT Pub. No.: WO2011/043954
PCT Pub. Date: Apr. 14, 2011

(65) Prior Publication Data
US 2012/0196894 A1    Aug. 2, 2012

Related U.S. Application Data

(60) Provisional application No. 61/249,360, filed on Oct. 7, 2009.

(51) Int. Cl.
| | | |
|---|---|---|
| *C07D 215/38* | (2006.01) | |
| *C07C 215/20* | (2006.01) | |
| *C07C 211/34* | (2006.01) | |
| *C07C 25/02* | (2006.01) | |
| *A61K 31/133* | (2006.01) | |

(52) U.S. Cl.
CPC ............. *C07C 215/20* (2013.01); *C07C 211/34* (2013.01); *C07C 25/02* (2013.01); *A61K 31/133* (2013.01)
USPC .......................................... 546/312; 546/159

(58) Field of Classification Search
CPC .... C07C 215/20; C07C 211/34; C07C 25/02; A61K 31/133
USPC ................... 514/576; 546/312, 159
See application file for complete search history.

(56) References Cited

U.S. PATENT DOCUMENTS

| | | | |
|---|---|---|---|
| 5,369,094 A | 11/1994 | Schally et al. | |
| 7,488,740 B2 | 2/2009 | Bakthavatchalam et al. | |
| 2004/0167336 A1 | 8/2004 | Apodaca et al. | |
| 2007/0196866 A1 | 8/2007 | Patapoutian et al. | |
| 2007/0219222 A1 | 9/2007 | Moran et al. | |
| 2008/0312316 A1 | 12/2008 | Culshaw et al. | |
| 2009/0023773 A1 | 1/2009 | Vohra et al. | |

FOREIGN PATENT DOCUMENTS

WO    WO2007073505    6/2007

OTHER PUBLICATIONS

Wang, Org Lett, vol. 11 (15), pp. 3410-3413, 2009.*
Corey et al., "TRPA1 is a Candidate for the Mechanosensitive Transduction Channel of Vertebrate hair Cells", Nature 2004, vol. 432, pp. 723-730.
Diogenes et al., "NGF Up-Regulates TRPA1: Implications for Orofacial Pain", J Dent Res, 2007, vol. 86, pp. 550-555.
Story et al., "ANKTM1, a TRP-Like Channel Expressed in Nociceptive Neurons, Is Activated by Cold Temperatures", Cell 2003, Vo. 112, pp. 819-829.
McNamara et al.,"TRPA1 Mediates Formalin-Induced Pain", Proc Natl Acad Sci USA, 2007, vol. 104, pp. 13525-13530.
Jordt et al., Mustard Oils and Cannabinoids Excite Sensory nerve Fibres Through the TRP Channel ANKTM1, Nature 2004, vol. 427, pp. 260-265.
MacPherson et al., "The Pungency of Garlic: Activation of TRPA1 and TRPV1 in Response to Allicine", Curr Biol., 2005, vol. 15, pp. 929-934.
Macpherson et al., "An Ion Channel Essential for Sensing Chemical Damage", J. Neurosci, 2007, vol. 27, pp. 11412-11415.
Namer et al., "TRPA1 and TrPM8 Activation in Humans: Effects of Cinnamaldehyde and Menthol", Neuroreport, 2005, vol. 16, pp. 955-959.
Ward et al., "A Comparison of the Effects of Noxious and Innocuous Counterstimuli on Experimentally Induced itch and Pain", Pain 1996, vol. 64, pp. 129-138.
Taylor-Clark et al., "Orostaglandin-Induced Activation of Nociceptive Neurons via Direct Interaction with Transient Receptor Potential A1 (TRPA1)", Mol Pharmacol, 2008, vol. 73, pp. 274-281.
Trevisani et al.,"4-Hydroxynonenal, an Endogenous Aldehyde, Causes Pain and Neurogenic Inflammation through Activation of the Irritant Receptor TRPA1", Proc Natl Acad Sci USA, 2007, vol. 104, pp. 13519-13524.
Hinman et al., "TRP Channel Activation by Reversible Covalent Modification", Proc Natl Acad Sci USA, 2006, vol. 103, pp. 19564-19568.

(Continued)

*Primary Examiner* — D M Seaman
(74) *Attorney, Agent, or Firm* — Sylvia A. Ayler; John C. Todaro

(57) ABSTRACT

The present invention relates to compositions and methods that modulate at least one TRP family member. Specifically, the present invention relates to novel TRPA1 antagonists and their use in the treatment of pain such as chronic inflammatory and neuropathic pain. Compounds that can modulate one or more TRPA1 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or misregulation of TRPA1 expression or function. The present invention further relates to methods and compositions that antagonize both a function of TRPA1 and a function of one or more additional TRP channels.

12 Claims, No Drawings

(56) References Cited

OTHER PUBLICATIONS

Macpherson et al., "Noxious Compounds Activate TRPA1 Ion Channels Through Covalent Modification of Cysteines", Nature, 2007, vol. 445, pp. 541-545.

Bautista et al., "Pungent products from Garlic Activate the Sensory Ion Channel TRPA1", 2005, PNAS, vol. 102, pp. 12248-12252.

E.L. Eliel et al., Stereochemistry of Carbon Compounds:, (John Wiley and Sons, New York 1994), pp. 1119-1190.

Berge et al., "Pharmaceutical Salts," J. Pharm. Sci., 1977, vol. 66, pp. 1-19.

Foresta et al., "Extracellular ATP Is a Trigger for the Acrosome Reaction in Human Spermatozoa", 1992, J. Biol. Chem. vol. 257, pp. 19443-19447.

Wang et al., "Extracellular ATP Shows Synergistic Enhancement of DNA Synthesis When Combined with Agents that Are Active in Wound Healing or as Neurotransmitters", 1990, Bioehirn. Biophys. Res. Commun, vol. 166, pp. 251-258.

Burnstock et al., "P2 Purinergic Receptors: Modulation of Cell Function and Therapeutc Potential", 2000, J. Pharmacol. Exp. Ther., vol. 295, pp. 862-869.

Burnstock, "Pathophysiology and Therapeutic Potential of Purinergic Signaling", Pharmacol Rev., 2006, vol. 58, pp. 58-86.

Jacobsen et al., "Scope and Mecanics of Tandem Cationic Aza-Cope Rearrangement—Mannich Cyclization Reactions", . J. Am. Chem. Soc. 1988, vol. 110, pp. 4329-4336.

Yeh et al., "A Facile Approach to the Synthesis of Allylic Spiro Ethers and Lactones", Synthesis, 2006,vol. 21, pp. 3621-3624.

\* cited by examiner

SEQUENCE LISTING

<160> NUMBER OF SEQ ID NOS: 1

<210> SEQ ID NO 1
<211> LENGTH: 1119
<212> TYPE: PRT
<213> ORGANISM: Homosapien

<400> SEQUENCE: 1

```
Met Lys Cys Ser Leu Arg Lys Met Trp Arg Pro Gly Glu Lys Lys Glu
 1               5                  10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Thr Cys Asp Asp Met Asp Thr
    50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Asn Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
    210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
```

```
                260                 265                 270
Cys Thr Ala Ile His Phe Ala Ala Thr Gln Gly Ala Thr Glu Ile Val
            275                 280                 285
Lys Leu Met Ile Ser Ser Tyr Ser Gly Ser Val Asp Ile Val Asn Thr
        290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
                325                 330                 335
Lys Ile Asp Ser Glu Gly Arg Ser Pro Leu Ile Leu Ala Thr Ala Ser
            340                 345                 350
Ala Ser Trp Asn Ile Val Asn Leu Leu Leu Ser Lys Gly Ala Gln Val
        355                 360                 365
Asp Ile Lys Asp Asn Phe Gly Arg Asn Phe Leu His Leu Thr Val Gln
    370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
                420                 425                 430
Leu Gly Phe Asn Val Ser Ile His Ser Lys Ser Lys Asp Lys Lys Ser
        435                 440                 445
Pro Leu His Phe Ala Ala Ser Tyr Gly Arg Ile Asn Thr Cys Gln Arg
    450                 455                 460
Leu Leu Gln Asp Ile Ser Asp Thr Arg Leu Leu Asn Glu Gly Asp Leu
465                 470                 475                 480
His Gly Met Thr Pro Leu His Leu Ala Ala Lys Asn Gly His Asp Lys
                485                 490                 495
Val Val Gln Leu Leu Leu Lys Lys Gly Ala Leu Phe Leu Ser Asp His
            500                 505                 510
Asn Gly Trp Thr Ala Leu His His Ala Ser Met Gly Gly Tyr Thr Gln
        515                 520                 525
Thr Met Lys Val Ile Leu Asp Thr Asn Leu Lys Cys Thr Asp Arg Leu
    530                 535                 540
Asp Glu Asp Gly Asn Thr Ala Leu His Phe Ala Ala Arg Glu Gly His
545                 550                 555                 560
Ala Lys Ala Val Ala Leu Leu Leu Ser His Asn Ala Asp Ile Val Leu
                565                 570                 575
Asn Lys Gln Gln Ala Ser Phe Leu His Leu Ala Leu His Asn Lys Arg
            580                 585                 590
Lys Glu Val Val Leu Thr Ile Ile Arg Ser Lys Arg Trp Asp Glu Cys
        595                 600                 605
Leu Lys Ile Phe Ser His Asn Ser Pro Gly Asn Lys Cys Pro Ile Thr
    610                 615                 620
Glu Met Ile Glu Tyr Leu Pro Glu Cys Met Lys Val Leu Leu Asp Phe
625                 630                 635                 640
Cys Met Leu His Ser Thr Glu Asp Lys Ser Cys Arg Asp Tyr Tyr Ile
                645                 650                 655
Glu Tyr Asn Phe Lys Tyr Leu Gln Cys Pro Leu Glu Phe Thr Lys Lys
            660                 665                 670
Thr Pro Thr Gln Asp Val Ile Tyr Glu Pro Leu Thr Ala Leu Asn Ala
        675                 680                 685
```

```
Met Val Gln Asn Asn Arg Ile Glu Leu Leu Asn His Pro Val Cys Lys
    690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
        755                 760                 765

Leu Ile Lys Thr Cys Met Ile Leu Val Phe Leu Ser Ile Phe Gly
770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
        915                 920                 925

Asn Glu Leu Ala His Pro Val Leu Ser Phe Ala Gln Leu Val Ser Phe
930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
        995                 1000                1005

Lys Pro Arg Ser Gly Gly Met Leu Phe His Ile Phe Cys Phe Leu Phe
1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
            1060                1065                1070

Glu Ile Ile Ser Glu Thr Glu Asp Asp Ser His Cys Ser Phe Gln
        1075                1080                1085

Asp Arg Phe Lys Lys Glu Gln Met Glu Gln Arg Asn Ser Arg Trp Asn
1090                1095                1100
```

```
Thr Val Leu Arg Ala Val Lys Ala Lys Thr His His Leu Glu Pro
1105                1110                1115
```

TRPA1 ANTAGONISTS

CROSS REFERENCE TO RELATED APPLICATIONS

This application is the National Stage of International Application No. PCT/US2010/050493 filed on Sep. 28, 2010, which claims the benefit under 35 U.S.C. 119(e) of U.S. Provisional Application No. 61/249,360, filed Oct. 7, 2009.

BACKGROUND OF THE INVENTION

The TRP channels constitute a large and important class of channels involved in modulating cellular homeostatis. The channels are generally classified into six groups: TRPC (short), TRPV (vanilloid), TRPM (long, melastatin), TRPP (polycystins), TRPML (mucolipins), and TRPA (Ankyrin). The TRPC family has four groups TRPC1, TRPC4,5, TRPC3,6,7 and TRPC2; based on sequence homology and functional similarities. The TRPV family has 6 members, including TRPV5 and TRPV6, which are more closely related to each other than to TRPV1, TRPV2, TRPV3, and TRPV4. The TRPM family has 8 members, TRPMI (Melastatin or LTRPCI), TRPM3 (KIAA16I6 or LTRPC3), TRPM7 (TRP-PLIK, ChaK(1), LTRPC7), TRPM6 (ChaK2), TRPM2 (TRPC7 or LTRPC2), TRPM8 (Trp-p8 or CMRI), TRPMS (Mtrl or LTRPC5), and TRPM4 (FLJ2004I or LTRPC4). The sole mammalian member of the TRPA family is ANKTM1, also known as TRPA1. TRPA1 is most closely related to TRPV3, and is more closely related to TRPV1 and TRPV2 than to TRPV5 and TRPV6. The TRPML family include TRPMLI (mucolipins 1), TRPML2 (mucolipins 2), and TRPML3 (mucolipin3). The TRPP family contains two groups of channels, those believed to have six trans-membrane domains (TRPP2 (PKD2), TRPP3 (PKD2L1), TRPP5 (PKD2L2)) and those that have 11 (TRPPI (PKDI, PC I), PKD-REJ and PKD-1 LI).

TRPA1 is a non-selective cation channel and is the sole mammalian member that defines the TRPA subfamily. In addition to calcium, ions, TRPA1 channels are permeable to other cations, for example sodium and Zinc. Thus, TRPA1 channels modulate membrane potential by modulating the flux of cations. Although non-selective cation channels such as TRPA1 modulate, among other things, calcium ion flux, they are mechanistically distinct from voltage-gated calcium channels. Voltage-gated calcium channels generally respond to depolarization of the potential difference across the membrane and can open to permit an influx of calcium from the extracellular medium and a rapid increase in intracellular calcium levels or concentrations. However, non-selective cation channels are generally signal transduction gated, long lasting, and produce less rapid changes in ion concentration. These mechanistic differences are accompanied by structural differences among voltage-gated and cation permeable channels. Thus, it is important to recognize the significant structural, functional, and mechanistic differences among different classes of ion channels even though many of the diverse channels act to regulate ion flux and membrane potential in various cell types and in response to numerous stimuli.

TRPA1 was shown to be highly expressed in dorsal root, trigeminal, and nodose ganglia in a specific subpopulation of neurons coexpressing another transient receptor potential family member, TRPV1, and in the hair cells of the inner ear (See Corey D P, et al., *Nature* 2004, 432(7018):723-730; Diogenes A, et al., *J Dent Res* 2007, 86(6):550-555; and Story G M, et al., *Cell* 2003, 112(6):819-829). After originally being characterized as a noxious cold-activated ion channel, several reports showed that TRPA1 can be activated by a large number of pungent or irritant compounds, such as cinnamaldehyde, AITC, acrolein, allicin, and formalin, all of which can induce acute pain, hyperalgesia, or neurogenic inflammation in animals and humans (See McNamara C R, et A, *Proc Natl Acad Sci USA* 2007, 104(33):13525-13530; Jordt S E, et al., *Nature* 2004, 427(6971):260-265; Macpherson 1-1, et al., *Curr Biol* 2005, 15(10):929-934; Macpherson L J, et al., *J Neurosci* 2007, 27(42):11412-11415; Namer B, et al., *Neuroreport* 2005, 16(9):955-959; and Ward L, et al., *Pain* 1996, 64(1):129-138). Additionally, these compounds have been shown to activate primary afferent nociceptors and enhance spontaneous and stimulus-evoked responses of spinal dorsal horn sensory neurons following peripheral application. More recently, the alpha, beta-unsaturated aldehyde, 4-hydroxy-2-nonenal (TINE) and the electrophilic carbon-containing PGJ2 metabolite, 15dPGJ2, released in response to tissue injury, inflammation, and oxidative stress, were reported to be the first endogenous activators of TRPA1 (Taylor-Clark T E, et al., *Mol Pharmacol* 2008, 73(2):274-281; and Trevisani M, et al., *Proc. Natl. Acad Sci USA* 2007, 104(33):13519-13524). It has also been reported that the majority of TRPA1 activators gate the channel through chemical reactivity of their electrophilic groups with some of the nucleophilic cysteine residues at the N-terminus of the channel and that TRPA1 can be gated through another mode of activation involving its N-terminal EF-hand calcium binding domain (Sec Hinman A, et al., *Proc Natl Acad Sci USA* 2006, 103(51):19564-19568; Macpherson L J, et al., *Nature* 2007, 445(7127):541-545). See also TRPA1 (Jordt et al. (2004) Nature 427:260-265; Bautista et al., (2005) PNAS: 102(34):12248-12252), WO2007073505, US2007219222, U.S. Pat. No. 5,369,094, and US2007196866.

The recent discoveries and descriptions of the transient receptor potential family of receptors, including TRPV1 and TRPA1, has provided a number of potential new therapeutic targets for treating chronic and acute pain, including acute formalin and CFA induced pain. Safe and effective treatment for chronic inflammatory and neuropathic pain remains a key unmet medical need for many patients.

SUMMARY OF THE INVENTION

The present invention relates to compositions and methods that modulate at least one TRP family member. Specifically, the present invention relates to novel TRPA1 antagonists and their use in the treatment of pain such as chronic inflammatory and neuropathic pain. Antagonizing a function of TRPA1 provides a means for modulating calcium homeostasis, sodium homeostasis, intracellular calcium levels, membrane polarization (resting membrane potential), and/or cation levels in a cell. Compounds that can modulate one or more TRPA1 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or misregulation of TRPA1 expression or function. The present invention further relates to methods and compositions that antagonize both a function of TRPA1 and a function of one or more additional TRP channels.

The present invention provides compounds that modulate TRPA1 function, and methods employing these compounds. Another aspect of the invention is a method of modulating a TRPA1 function in a cell or animal comprising administering an effective amount of a compound that inhibits a TRPA1 function, wherein the compound inhibits a TRPA1-mediated ion flux. Another aspect of the invention relates to a method of modulating a TRPA1 function in a cell comprising administering to the cell an effective amount of a compound that inhibits TRPA1 function, wherein the compound inhibits calcium influx mediated by TRPA1. Another aspect of the present invention relates to a method of preventing or treating a disease or condition related to TRPA1 function in a subject comprising administering to the subject a therapeutically effective amount of a compound that inhibits TRPA1 function, wherein the compound inhibits the calcium influx mediated by TRPA1. Still another aspect of the present invention relates to method of preventing or treating a disease or condition related to TRPA1 function in a subject comprising administering to the subject a therapeutically effective amount of a compound that inhibits TRPA 1 function, wherein the compound inhibits the calcium flux mediated by TRPA1. Inhibition of the calcium influx refers to the ability of a compound to inhibit that calcium influx in either an in vitro or an in vivo assay. Inhibition of calcium flux in either an in vivo or an in vitro assay serves as a proxy for the particular functional activity of the particular compound.

These and other aspects of the invention will be realized upon review of the specification in its entirety.

DETAILED DESCRIPTION OF THE INVENTION

The present invention is directed to compounds of Formula I:

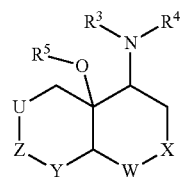

I or a pharmaceutically acceptable salt thereof, a solvate, hydrate, stereoisomer, enantiomer, or prodrug of the compound or its salt wherein:
W represents $CH_2$, $NC(O)R^4$, $NC(O)NR^3R^4$, $NR^4$, $CHR^4$, —O—
U, X, Y, and Z independently represent $CH_2$, or —O—;
$R^2$ represents hydrogen, or $C_{1-6}$ alkyl;
$R^5$ represents hydrogen, or $C_{1-6}$ alkyl, $C(O)N(R^2)_2$, $C(O)R^2$, $C(O)O(CH_2)_nC_{6-10}$ aryl, $(CHR^2)_nC_{5-10}$ heterocyclyl, $(CHR^2)_nC_{6-10}$ aryl; said alkyl, heterocyclyl and aryl optionally substituted with 1 to 3 groups of $R^a$;
$R^3$ and $R^4$ independently represent H, $(CH_2)_nOR^2$, $(CH_2)_nOR^5$, $CH(OR^2)_2$, $CH_2O(CH_2)_nOR^2$, $CHF_2$, $(CH_2)_nNR^2R^5$, $(CHR^2)_nC_{5-10}$ heterocyclyl, $(CHR^2)_nC_{6-10}$ aryl, $(CHR^2)_nC_{3-10}$ cycloalkyl, $C_{1-6}$ alkoxy, $C_{2-6}$ alkenyl, $CF_3$, $CF_2$, $CH_2Si(C_{5-6}$ aryl$)_2R^2$, $C(O)_{1-2}R^2$, or $C_{1-6}$ alkyl; said alkyl, cycloalkyl, heterocyclyl and aryl optionally substituted with 1 to 3 groups of $R^a$;
or $R^3$ and $R^4$ can be combined with the nitrogen to which they are attached to form a $C_{5-10}$ heterocyclyl optionally containing one or more additional heteroatoms selected from O, N, and S and optionally substituted with 1 to 3 groups of $R^a$;
$R^a$ represents $C_{1-6}$ alkyl, halogen, hydroxyl, $OR^2$, $(CH_2)_nCF_3$, $C_{3-6}$ cycloalkyl, $C(O)N(R^2)_2$, $C(R^2)_2OR^2$, $C(O)R^2$, $NO_2$, $CN$, $N(R^2)_2$, $C(O)OR^2$, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN; and
n represents 0 to 4.

Another aspect of this invention is realized when $R^5$ is hydrogen and all other variables are as originally described.

Another aspect of this invention is realized when $R^5$ is $C_{1-6}$ alkyl and all other variables are as originally described. A sub-embodiment of this invention is realized when $R^5$ is methyl.

Another aspect of this invention is realized when $R^3$ and $R^4$ are independently selected from the group consisting of H, $(CHR^2)_nC_{5-10}$ heterocyclyl, $(CHR^2)_nC_{6-10}$ aryl, $(CHR^2)_nC_{3-10}$ cycloalkyl, or $C_{1-6}$ alkyl; said alkyl, cycloalkyl, heterocyclyl and aryl optionally substituted with 1 to 3 groups of $R^a$ and all other variables are as originally described. A subembodiment of this aspect of $R^3$ and $R^4$ is realized when one of $R^3$ and $R^4$ is hydrogen, or $CH_3$, and the other is not. A further subembodiment of this aspect of $R^3$ and $R^4$ is realized when one of $R^3$ and $R^4$ is hydrogen and the other is selected from the group consisting of $C_{1-6}$ alkyl, cyclopropyl, cyclobutyl, cyclopentyl, cyclohexyl, indeneyl, $(CHR^2)_n$phenyl, $(CHR^2)_n$indolyl, $(CHR^2)_n$napthyl, piperonyl, $(CHR^2)_n$pridyl, $(CHR^2)_n$imidazolyl, $(CHR^2)_n$pyrimidinyl, pyranoyl, $(CHR^2)_n$quinolinyl, $(CHR^2)_n$isoquinolinyl, all optionally substituted with 1 to 3 groups of $R^a$ and all other variables are as originally described. A subembodiment of this aspect of $R^3$ and $R^4$ is realized when the $C_{1-6}$ alkyl is selected from the group consisting of methyl, ethyl, propyl, isopropyl, butyl, isobutyl, and the like, all of which are optionally substituted with 1 to 3 groups of $R^a$.

Another aspect of this invention is realized when $R^3$ and $R^4$ are combined with the nitrogen to which they are attached to form a $C_{5-10}$ heterocyclyl optionally containing one or more additional heteroatoms selected from O, N and S, and optionally substituted with 1 to 3 groups of $R^a$ and all other variables are as originally described. A subembodiment of this aspect of $R^3$ and $R^4$ is realized when they are combined to form morpholinyl.

Another aspect of this invention is realized when $R^a$ is selected from the group consisting of $C_{1-6}$ alkyl, halogen, CN, $OR^2$, $(CH_2)_nCF_3$, $C_{3-6}$ cycloalkyl, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN. A subembodiment of this aspect of $R^a$ is realized when it is selected from the group consisting of fluorine, chlorine, methoxy, methyl, ethyl, propyl, butyl, OH, CN, $CF_3$, and $OR^2$.

Another aspect of this invention is realized when W is —$CHR^4$ and all other variables are as originally described. A sub-embodiment of this invention is realized when $R^4$ is H. Another sub-embodiment of this invention is realized when $R^4$ is selected from the group consisting of $(CH_2)_nC_{5-10}$ heterocyclyl, $C_{1-6}$ alkoxy, $(CH_2)_nOH$ and $CH_2OSi(Phenyl)_2R^2$, said heterocyclyl, alkoxy and phenyl optionally substituted with 1 to 3 groups of $R^a$.

Still another aspect of this invention is realized when W is $NR^4$ and all other variables are as originally described.

Yet another aspect of this invention is realized when W is —O— and all other variables are as originally described.

Another aspect of this invention is realized when W is —$NC(O)R^4$ and all other variables are as originally described. A subembodiment of this invention is realized when $R^4$ is selected from the group consisting of $(CH_2)_nC_{5-10}$ heterocyclyl, $(CH_2)_nC_{6-10}$ aryl, $(CH_2)_nC_{3-10}$ cycloalkyl, or $C_{1-6}$ alkyl, said alkyl, heterocyclyl, aryl, and cycloalkyl optionally substituented with 1 to 3 groups of $R^a$. Still another subembodiment of this invention is realized when $R^4$ is selected from the group consisting of $C_{1-6}$ alkyl, $(CH_2)_n$phenyl, $(CH_2)_n$indenyl, pyranoyl, and, piperonyl, said alkyl, phenyl, and indenyl optionally substituented with 1 to 3 groups of $R^a$.

Another aspect of this invention is realized when W is or —NC(O)NR³R⁴— and all other variables are as originally described. A subembodiment of this invention is realized when one of $R^3$ and $R^4$ is hydrogen and the other is selected from the group consisting of $(CH_2)_nC_{5-10}$ heterocyclyl, $(CH_2)_nC_{6-10}$ aryl, $(CH_2)_nC_{3-10}$ cycloalkyl, or $C_{1-6}$ alkyl, said alkyl, heterocyclyl, aryl, and cycloalkyl optionally substituented with 1 to 3 groups of $R^a$. Still another subembodiment of this invention is realized when one of $R^3$ and $R^4$ is hydrogen and the other is selected from the group consisting of $C_{1-6}$ alkyl, and $(CH_2)_a$phenyl, said alkyl, and phenyl optionally substituented with 1 to 3 groups of $R^a$.

Yet another aspect of this invention is realized when W, U, Z, Y and X are $CH_2$ and all other variables are as originally described.

Still another aspect of this invention is realized when W is $NC(O)R^4$, U, Z, Y and X are $CH_2$, and all other variables are as originally described.

Another aspect of this invention is realized when W is $NC(O)NR^3R^4$, U, Z, Y and X are $CH_2$, and all other variables are as originally described.

Another aspect of this invention is realized when W is $NR^4$, U, Z, Y and X are $CH_2$, and all other variables are as originally described.

Another aspect of this invention is realized when Y is —O—, W, U, Z and X are $CH_2$, and all other variables are as originally described.

Another aspect of this invention is realized when X is —O—, W, U, Z and Y are $CH_2$, and all other variables are as originally described.

Another aspect of this invention is realized when Z is —O—, W, U, Y and X are $CH_2$, and all other variables are as originally described.

Another aspect of this invention is realized when W is —O—, Z, U, Y and X are $CH_2$, and all other variables are as originally described.

Still another aspect of this invention is realized with the compound of structural formula Ia:

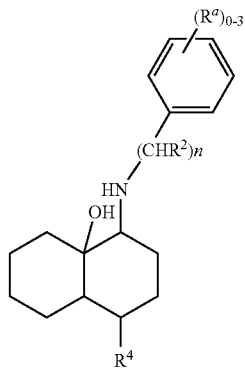

Ia or a pharmaceutically acceptable salt thereof, a solvate, hydrate, stereoisomer, enantiomer, or prodrug of the compound or its salt,
wherein $R^a$ and n are as described herein, and $R^4$ is selected from the group consisting of H, $(CH_2)_nOR^2$, $CH(OR^2)_2$, and $CH_2Si(C_{5-6} aryl)_2R^2$. A subembodiment of the compound of formula Ia is realized when $R^a$ is selected from the group consisting of $C_{1-6}$ alkyl, halogen, CN, $OR^2$, $(CH_2)_nCF_3$, $C_{3-6}$ cycloalkyl, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN. A further subembodiment of this aspect of formula Ia is realized when $R^a$ selected from the group consisting of fluorine, chlorine, methyl, ethyl, propyl, butyl, phenyl, tetrazolyl, OH, CN, $CF_3$, and $OR^2$, preferably fluorine, chlorine, phenyl, tetrazolyl, methyl, methoxy, OH, and CN. Another subembodiment of the compound of formula Ia is realized when n is 0-3, preferably 0-2, 0-1 or 0. Still another subembodiment of the compound of formula Ia is realized when $R^2$ is hydrogen. Another subembodiment of the compound of formula Ia is realized when $R^2$ is methyl.

Still another aspect of this invention is realized with the compound of structural formulas Ib:

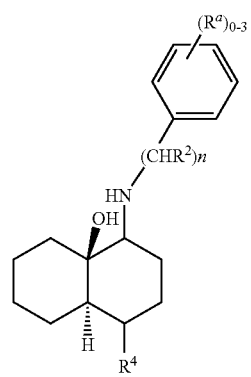

Ib or a pharmaceutically acceptable salt thereof, or a solvate, hydrate, stereoisomer, enantiomer, or prodrug of the compound or its salt, wherein $R^a$ and n are as described herein. A subembodiment of the compound of formula Ib is realized when $R^a$ is selected from the group consisting of $C_{1-6}$ alkyl, halogen, CN, $OR^2$, $(CH_2)_nCF_3$, $C_{3-6}$ cycloalkyl, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN. A further subembodiment of this aspect of formula Ib and Ib1 is realized when $R^a$ selected from the group consisting of fluorine, chlorine, methyl, ethyl, propyl, butyl, phenyl, tetrazolyl, OH, CN, $CF_3$, and $OR^2$, preferably fluorine, chlorine, phenyl, tetrazolyl, methyl, methoxy, OH, and CN. Another subembodiment of the compound of formula Ib is realized when n is 0-3, preferably 0-2, 0-1, or 0. Still another subembodiment of the compound of formula Ib is realized when $R^2$ of formula Ib is hydrogen. Another subembodiment of the compound of formula Ib is realized when $R^2$ is methyl.

Still another aspect of this invention is realized with the compound of structural formula Ic:

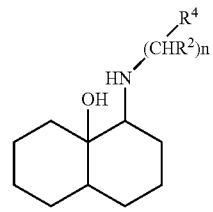

Ic or a pharmaceutically acceptable salt thereof, a solvate, hydrate, stereoisomer, enantiomer, or prodrug of the compound or its salt, wherein $R^4$ is selected from the group consisting of $(CHR^2)_nC_{5-10}$ heterocyclyl, $(CHR^2)_nC_{6-10}$ aryl, $(CHR^2)_nC_{3-10}$ cycloalkyl, or $C_{1-6}$ alkyl; said alkyl, cycloalkyl, heterocyclyl and aryl optionally substituted with 1 to 3 groups of $R^a$. A subembodiment of the compound of formula Ic is realized when $R^4$ is methyl, ethyl, propyl, or butyl optionally substituted with 1 to 3 groups of $R^a$. Another subembodiment of the compound of formula Ic is realized when $R^4$ is cyclobutyl, cyclopropyl, cyclopentyl, or cyclohexyl, all optionally substituted with 1 to 3 groups of $R^a$ and $R^2$ of formula Ic, when present is hydrogen or methyl. Another embodiment of the compound of formula Ic is realized when $R^4$ is optionally substituted piperonyl, indolyl, pyridyl, imidazolyl, pyrimidinly, quinolinyl, isoquinolinyl, pyranoyl, or naphthyl, and $R^2$ of formula. Ic when present is hydrogen or methyl. For the compounds of the formula Ic, optionally substituted means substituted with 1 to 3 groups of $R^a$. Another subembodiment of the compound of formula Ic is realized when n is 0-3, preferably 0-2, 0-1 or 0.

Still another aspect of this invention is realized with the compound of structural formula Id:

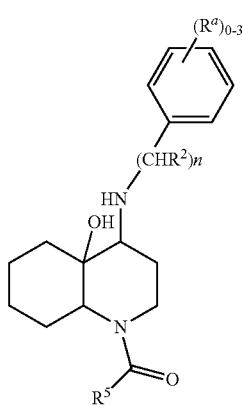

Id or a pharmaceutically acceptable salt thereof, a solvate, hydrate, stereoisomer, enantiomer, or prodrug of the compound or its salt, wherein $R^a$ and n are as originally described herein and $R^5$ is $R^4$ or —$NR^3R^4$. A subembodiment of the compound of formula Id is realized when $R^5$ is $R^4$ which is selected from the group consisting of $C_{1-6}$ alkyl, $C_{3-6}$ cycloalkyl, $(CH_2)_nC_{5-10}$ heterocyclyl, or $(CH_2)_nC_{6-10}$ aryl, said cycloalkyl, heterocyclyl and aryl optionally substituted with 1 to 3 of $R^a$. A further subembodiment of the compound of formula Id is realized when $R^5$ is $C_{1-6}$ alkyl, $(CH_2)_n$phenyl, pyranoyl, or indenyl, said alkyl, phenyl andindeneyl optionally substituted with 1 to 3 groups of $R^a$. Another subembodiment of the compound of formula Id is realized when $R^5$ is —$NR^3R^4$, wherein one of $R^3$ and $R^4$ is hydrogen and the other is selected from the group consisting of $C_{1-6}$ alkyl, $C_{3-6}$ cycloalkyl, $(CH_2)_nC_{5-10}$ heterocyclyl, or $(CH_2)_nC_{6-10}$ aryl, said cycloalkyl, heterocyclyl and aryl optionally substituted with 1 to 3 of $R^a$. A further subembodiment of the compound of formula Id when $R^4$ is —$NR^3R^4$ is realized when one of $R^3$ and $R^4$ is hydrogen and the other is $C_{1-6}$ alkyl, and $(CH_2)_n$phenyl, said alkyl, and phenyl optionally substituted with 1 to 3 groups of $R^a$. Another subembodiment of the compound of formula Id is realized when $R^a$ is selected from the group consisting of $C_{1-6}$ alkyl, halogen, CN, $OR^2$, $(CH_2)_nCF_3$, $C_{3-6}$ cycloalkyl, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN. A further subembodiment of this aspect of formula Id is realized when $R^a$ selected from the group consisting of fluorine, chlorine, methyl, ethyl, propyl, butyl, phenyl, tetrazolyl, OH, CN, $CF_3$, and $OR^2$, preferably fluorine, chlorine, phenyl, tetrazolyl, methyl, methoxy, OH, and CN. Another subembodiment of the compound of formula Id is realized when n is 0-3, preferably 0-2, 0-1 or 0. Still another subembodiment of the compound of formula Id is realized when $R^2$ if present, is hydrogen.

Another subembodiment of the compound of formula Id is realized when $R^2$ if present, is methyl.

Still another aspect of this invention is realized with the compound of structural formula Ie:

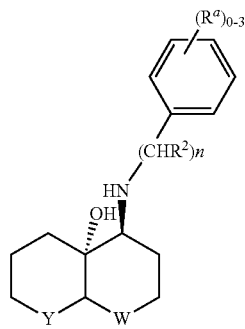

Ie or a pharmaceutically acceptable salt thereof, a solvate, hydrate, stereoisomer, enantiomer, or prodrug of the compound or its salt, wherein $R^a$ and n are as described herein, and W is $CHR^4$, or —O— and Y is $CH_2$ or —O—, $R^4$ is selected from the group consisting of H, $(CH_2)_nOR^2$, $CH(OR^2)_2$, and $CH_2Si(C_{5-6}$ aryl$)_2R^2$, provided that both Y and W are not —O— at the same time. A subembodiment of the compound of formula Ie is realized when $R^a$ is selected from the group consisting of $C_{1-6}$ alkyl, halogen, CN, $OR^2$, $(CH_2)_nCF_3$, $C_{3-6}$ cycloalkyl, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN. A further subembodiment of this aspect of formula Ie is realized when $R^a$ selected from the group consisting of fluorine, chlorine, methyl, ethyl, propyl, butyl, phenyl, tetrazolyl, OH, CN, $CF_3$, and $OR^2$, preferably fluorine, chlorine, phenyl, tetrazolyl, methyl, methoxy, OH, and CN. Another subembodiment of the compound of formula Ie is realized when n is 0-3, preferably 0-2, 0-1 or 0. Still another subembodiment of the compound of formula Ie is realized when $R^2$ is hydrogen. Another subembodiment of the compound of formula Ie is realized when $R^2$ is methyl.

Another aspect of this invention is realized with the compound of structural formula If:

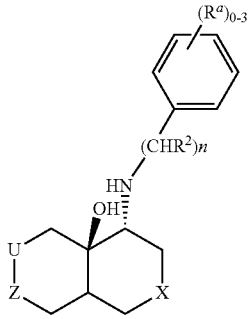

If or a pharmaceutically acceptable salt thereof, a solvate, hydrate, stereoisomer, enantiomer, or prodrug of the compound or its salt, wherein $R^a$ and n are as described herein, and U, X, and Z are independently selected from $CH_2$ or —O—, provided that only one of U, X, and Z can be —O— at any given time. A subembodiment of the compound of formula If is realized when $R^a$ is selected from the group consisting of $C_{1-6}$ alkyl, halogen, CN, $OR^2$, $(CH_2)_nCF_3$, $C_{3-6}$ cycloalkyl, $(CH_2)_nC_{5-10}$ heterocyclyl, or $(CH_2)_nC_{6-10}$ aryl, said heterocyclyl and aryl optionally substituted with 1 to 3 groups of $C_{1-6}$ alkyl, halogen, hydroxyl, $(CH_2)_nCF_3$, or CN. A further subembodiment of this aspect of formula If is realized when $R^a$ selected from the group consisting of fluorine, chlorine, methyl, ethyl, propyl, butyl, phenyl, tetrazolyl, OH, CN, $CF_3$, and $OR^2$, preferably fluorine, chlorine, phenyl, tetrazolyl, methyl, methoxy, OH, and CN. Another subembodiment of the compound of formula If is realized when n is 0-3, preferably 0-2, 0-1 or 0. Still another subembodiment of the compound of formula If is realized when $R^2$ is hydrogen. Another subembodiment of the compound of formula If is realized when $R^2$ is methyl.

Examples of compounds of this invention are found in Tables A and B:

TABLE A

| COMPOUND | |
|---|---|
| (4aR,8aR)-4-[(4-fluorophenyl)amino]octahydronaphthalen-4a(2H)-ol | 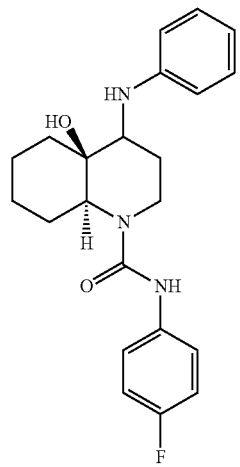 [SMILES: O=C(Nc1ccc(F)cc1)N1CCC(Nc2ccccc2)[C@@]2(O)CCCC[C@H]12] |
| (4aR,8aR)-4-[(3,4-difluorophenyl)amino]octahydronaphthalen-4a(2H)-ol | 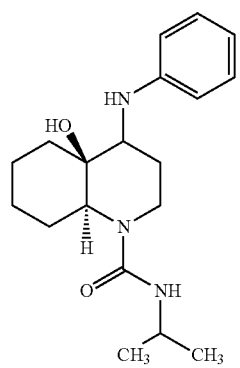 [SMILES: CC(C)NC(=O)N1CCC(Nc2ccccc2)[C@@]2(O)CCCC[C@H]12] |
| 2,3-dihydro-1H-inden-1-yl-[(4aS,8aS)-4a-hydroxy-4-(phenylamino)octahydroquinolin-1(2H)-yl]methanone | 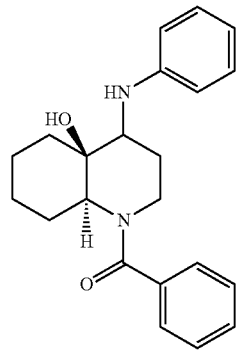 [SMILES: O=C(c1ccccc1)N1CCC(Nc2ccccc2)[C@@]2(O)CCCC[C@H]12] |

TABLE A-continued

| COMPOUND | |
|---|---|
| (4aS,8aS)-N-(4-fluorophenyl)-4a-hydroxy-4-(phenylamino)octahydroquinoline-1(2H)-carboxamide | 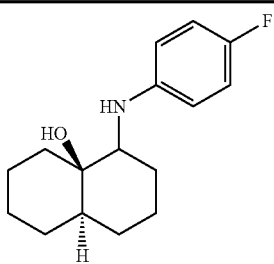 |
| (4aS,8aS)-4a-hydroxy-4-(phenylamino)-N-(propan-2-yl)octahydroquinoline-1(2H)-carboxamide | 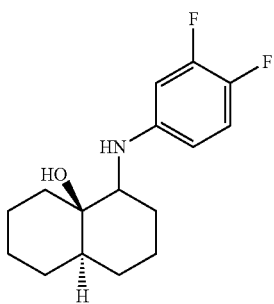 |
| [(4aS,8aS)-4a-hydroxy-4-(phenylamino)octahydroquinolin-1(2H)-yl](phenyl)methanone | 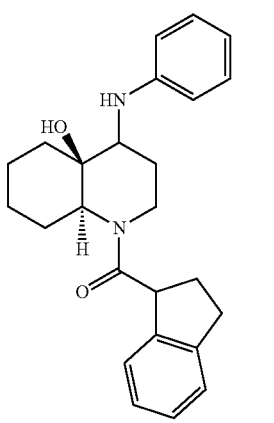 |
| [(4aS,8aS)-4a-hydroxy-4-(phenylamino)-octahydroquinolin-1(2H)-yl](tetrahydro-2H-pyran-4-yl)methanone | 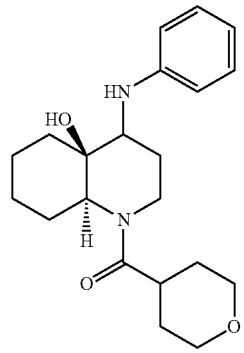 [SMILES: O=C(C1CCOCC1)N1CCC(Nc2ccccc2)[C@@]2(O)CCCC[C@H]12] |

TABLE A-continued

| COMPOUND | |
|---|---|
| (4aS,8aS)-4a-hydroxy-N-phenyl-1-(3,3,3-trifluoropropanoyl)decahydroquinolin-4-aminium trifluoroacetate | 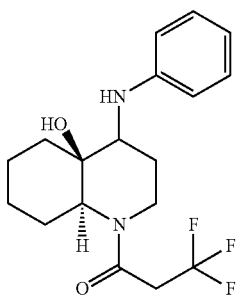 [SMILES: O=C(CC(F)(F)F)N1CCC(Nc2ccccc2)[C@@]2(O)CCCC[C@H]12] |
| 1-[(4aS,8aS)-4a-hydroxy-4-(phenylamino)octahydroquinolin-1(2H)-yl]-3-methylbutan-1-one | 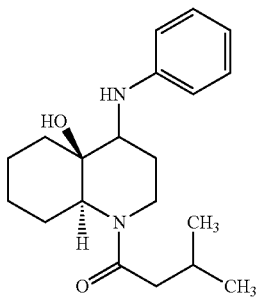 [SMILES: CC(C)CC(=O)N1CCC(Nc2ccccc2)[C@@]2(O)CCCC[C@H]12] |
| 1-[(4aS,8aS)-4a-hydroxy-4-(phenylamino)octahydroquinolin-1(2H)-yl]pentan-1-one | 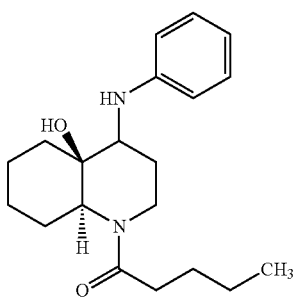 [SMILES: CCCCC(=O)N1CCC(Nc2ccccc2)[C@@]2(O)CCCC[C@H]12] |
| 1-[(4aS,8aS)-4a-hydroxy-4-(phenylamino)octahydroquinolin-1(2H)-yl]ethanone | 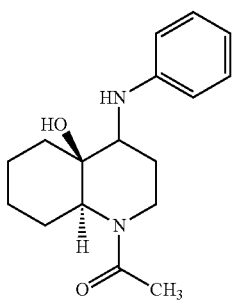 [SMILES: CC(=O)N1CCC(Nc2ccccc2)[C@@]2(O)CCCC[C@H]12] |
| (4aS,8aS)-1-benzyl-4-(phenylamino)octahydroquinolin-4a(2H)-ol | 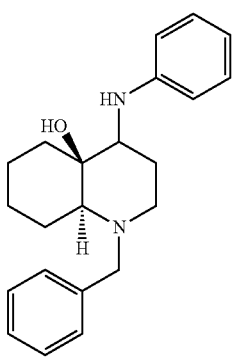 [SMILES: O[C@]12CCCC[C@@H]1N(Cc1ccccc1)CCC2Nc1ccccc1] |

TABLE A-continued

| COMPOUND | |
|---|---|
| (4aR,8aR)-4-(cyclopropylamino)octahydronaphthalen-4a(2H)-ol | 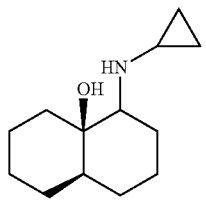 [SMILES: O[C@]12CCCC[C@@H]1CCCC2NC1CC1] |
| (4aR,8aR)-4-(propan-2-ylamino)octahydronaphthalen-4a(2H)-ol | 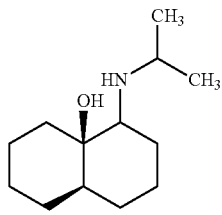 |
| (4aR,8aR)-4-[(2,4,6-trifluorophenyl)amino]octahydronaphthalen-4a(2H)-ol | 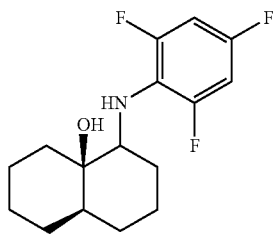 [SMILES: O[C@]12CCCC[C@@H]1CCCC2Nc1c(F)cc(F)cc1F] |
| (4aR,8aR)-4-[(2,4,5-trifluorophenyl)amino]octahydronaphthalen-4a(2H)-ol | 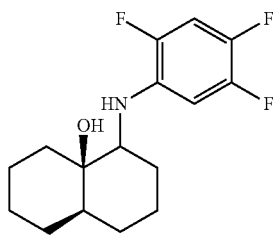 [SMILES: O[C@]12CCCC[C@@H]1CCCC2Nc1cc(F)c(F)cc1F] |
| (4aR,8aR)-4-[(3,4,5-trifluorophenyl)amino]octahydronaphthalen-4a(2H)-ol | 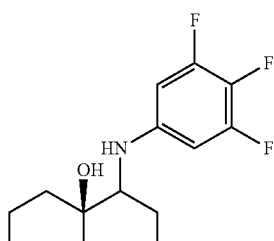 |
| (4aR,8aR)-4-[(2,3,5-trifluorophenyl)amino]octahydronaphthalen-4a(2H)-ol | 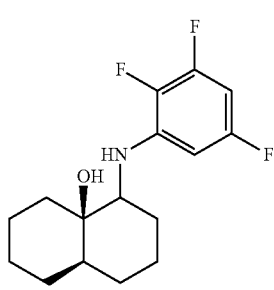 [SMILES: O[C@]12CCCC[C@@H]1CCCC2Nc1cc(F)cc(F)c1F] |

TABLE A-continued

| COMPOUND | |
|---|---|
| (4aR,8aR)-4-[(2,3,4-trifluorophenyl)amino]octahydronaphthalen-4a(2H)-ol | 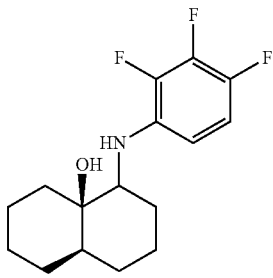 [SMILES: O[C@]12CCCC[C@@H]1CCCC2Nc1ccc(F)c(F)c1F] |
| (4aR,8aR)-4-[(3,5-difluorophenyl)amino]octahydronaphthalen-4a(2H)-ol | 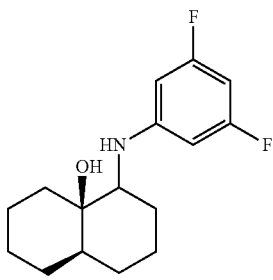 [SMILES: O[C@]12CCCC[C@@H]1CCCC2Nc1cc(F)cc(F)c1] |
| (4aR,8aR)-4-[(3,4-difluorophenyl)amino]octahydronaphthalen-4a(2H)-ol | 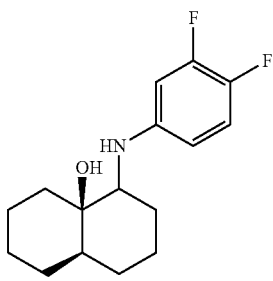 [SMILES: O[C@]12CCCC[C@@H]1CCCC2Nc1ccc(F)c(F)c1] |
| (4aR,8aR)-4-[(2,6-difluorophenyl)amino]octahydronaphthalen-4a(2H)-ol | 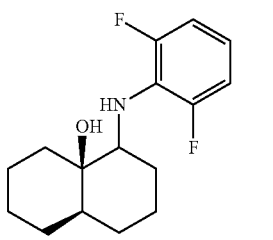 [SMILES: O[C@]12CCCC[C@@H]1CCCC2Nc1c(F)cccc1F] |
| (4aR,8aR)-4-[(2,3-difluorophenyl)amino]octahydronaphthalen-4a(2H)-ol | 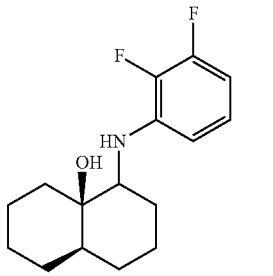 [SMILES: O[C@]12CCCC[C@@H]1CCCC2Nc1cccc(F)c1F] |
| (4aR,8aR)-4-[(4-fluorophenyl)amino]octahydronaphthalen-4a(2H)-ol | 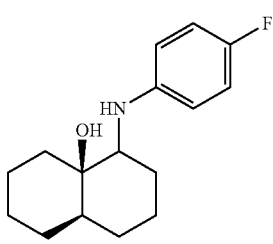 [SMILES: O[C@]12CCCC[C@@H]1CCCC2Nc1ccc(F)cc1] |
| (4aR,8aR)-4-[(3-fluorophenyl)amino]octahydronaphthalen-4a(2H)-ol | 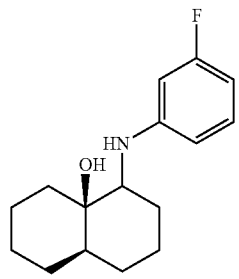 [SMILES: O[C@]12CCCC[C@@H]1CCCC2Nc1cccc(F)c1] |
| (4aR,8aR)-4-[(2-fluorophenyl)amino]octahydronaphthalen-4a(2H)-ol | 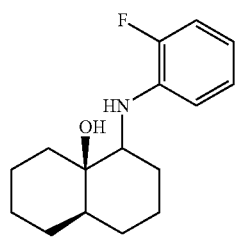 [SMILES: O[C@]12CCCC[C@@H]1CCCC2Nc1ccccc1F] |
| (4aR,8aR)-4-{[4-(1H-tetrazol-5-yl)phenyl]amino}octahydronaphthalen-4a(2H)-ol | 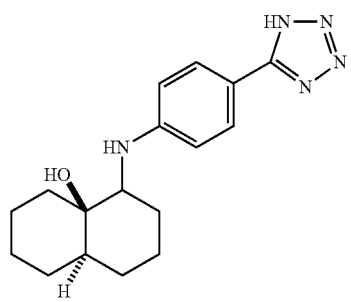 [SMILES: O[C@]12CCCC[C@@H]1CCCC2Nc1ccc(-c2nnn[nH]2)cc1] |
| (4aR,8aR)-4-{[3-(1H-tetrazol-5-yl)phenyl]amino}octahydronaphthalen-4a(2H)-ol | 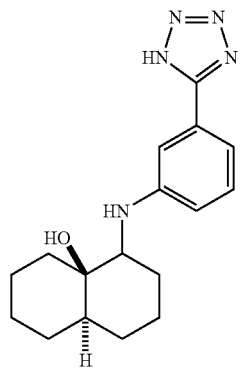 [SMILES: O[C@]12CCCC[C@@H]1CCCC2Nc1cccc(-c2nnn[nH]2)c1] |
| (4aR,8aR)-4-{[2-(1H-tetrazol-5-yl)phenyl]amino}octahydronaphthalen-4a(2H)-ol | 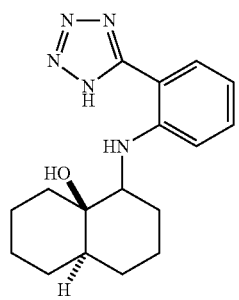 [SMILES: O[C@]12CCCC[C@@H]1CCCC2Nc1ccccc1-c1nnn[nH]1] |

TABLE A-continued

| COMPOUND | |
|---|---|
| 4-(phenylamino)octahydronaphthalen-4a(2H)-ol | |
| 4-(phenylamino)-octahydronaphthalen-4a(2H)-ol | |
| (4aR,8aR)-4-(1H-indol-7-ylamino)-octahydronaphthalen-4a(2H)-ol | |
| (4aR,8aR)-4-(biphenyl-4-ylamino)octahydro-naphthalen-4a(2H)-ol | |
| (4aR,8aR)-4-(biphenyl-3-ylamino)octahydro-naphthalen-4a(2H)-ol | |
| ethyl 3-{[(4aR,8aR)-8a-hydroxydeca-hydronaphthalen-1-yl]amino}-1H-indole-2-carboxylate | |
| (4aR,8aR)-4-(1H-indol-4-ylamino)-octahydronaphthalen-4a(2H)-ol | |
| (4aR,8aR)-4-(quinolin-8-ylamino)octahydro-naphthalen-4a(2H)-ol | |
| (4aR,8aR)-4-(isoquinolin-5-ylamino)octahydro-naphthalen-4a(2H)-ol | |
| (4aR,8aR)-4-(quinolin-5-ylamino)octahydro-naphthalen-4a(2H)-ol | |

TABLE A-continued

| COMPOUND | |
|---|---|
| (4aR,8aR)-4-(isoquinolin-1-ylamino)octahydro-naphthalen-4a(2H)-ol | |
| (4aR,8aR)-4-(quinolin-2-ylamino)octahydro-naphthalen-4a(2H)-ol | |
| (4aR,8aR)-4-(quinolin-6-ylamino)octahydro-naphthalen-4a(2H)-ol | |
| (4aR,8aR)-4-(quinolin-3-ylamino)octahydro-naphthalen-4a(2H)-ol | |
| (4aR,8aR)-4-(isoquinolin-3-ylamino)octahydro-naphthalen-4a(2H)-ol | |
| (4aR,8aR)-4-[(2,5-difluorophenyl)amino]octahydronaphthalen-4a(2H)-ol | |
| (4aR,8aR)-4-(naphthalen-2-ylamino)octahydro-naphthalen-4a(2H)-ol | |
| (4aR,8aR)-4-(naphthalen-1-ylamino)octahydro-naphthalen-4a(2H)-ol | |
| (4aR,8aR)-4-(biphenyl-2-ylamino)octahydro-naphthalen-4a(2H)-ol | |
| (4aS,8aR)-4-(morpholin-4-yl)octahydro-naphthalen-4a(2H)-ol | |

TABLE A-continued

| COMPOUND | |
|---|---|
| (4S,4aS,8aR)-4-{[2-(1H-indol-3-yl)ethyl]amino}octahydronaphthalen-4a(2H)-ol | 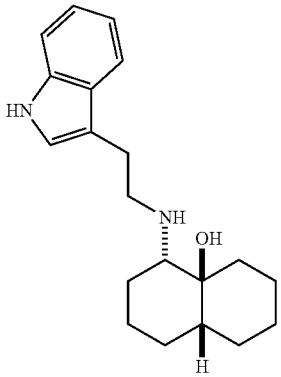 [SMILES: O[C@@]12CCCC[C@@H]1CCC[C@@H]2NCCc1c[nH]c2ccccc12] |
| (4R,4aS,8aR)-4-{[2-(1H-indol-3-yl)ethyl]amino}octahydronaphthalen-4a(2H)-ol | 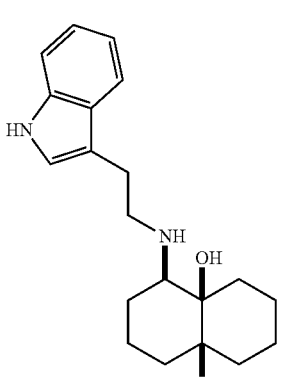 |
| (4S,4aS,8aR)-4-[(2-phenylethyl)-amino]octahydronaphthalen-4a(2H)-ol | 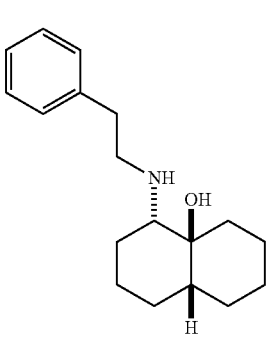 [SMILES: O[C@@]12CCCC[C@@H]1CCC[C@@H]2NCCc1ccccc1] |
| (4R,4aS,8aR)-4-[(2-phenylethyl)amino]octahydronaphthalen-4a(2H)-ol | 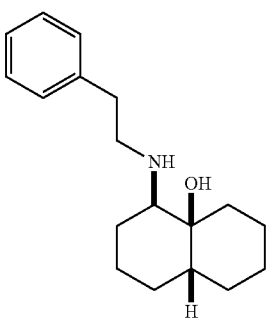 [SMILES: O[C@@]12CCCC[C@@H]1CCC[C@H]2NCCc1ccccc1] |
| (4R,4aS,8aR)-4-[(3-chlorophenyl)amino]octahydronaphthalen-4a(2H)-ol | 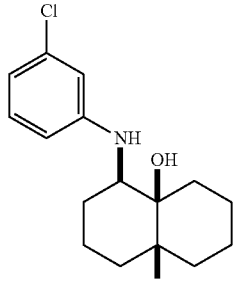 |
| (4R,4aS,8aR)-4-[(1,3-benzodioxol-5-ylmethyl)amino]octahydronaphthalen-4a(2H)-ol | 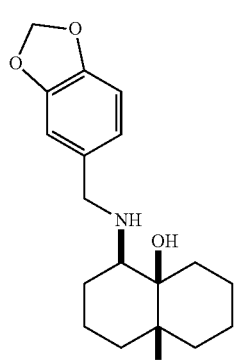 |
| (4S,4aS,8aR)-4-[(1,3-benzodioxol-5-ylmethyl)amino-]octahydronaphthalen-4a(2H)-ol | 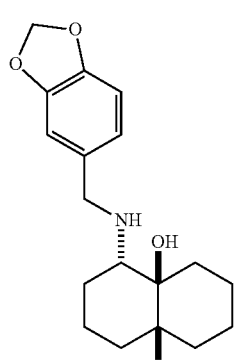 |
| (1R,4aR,8aS)-8a-hydroxy-N-(1-phenylethyl)decahydronaphthalen-1-aminium | 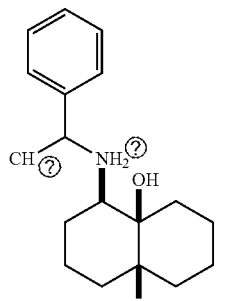 |

TABLE A-continued

| COMPOUND | |
|---|---|
| (1S,4aR,8aS)-8a-hydroxy-N-(1-phenylethyl)decahydronaphthalen-1-aminium | |
| (1R,4aR,8aS)-N-benzyl-8a-hydroxydecahydronaphthalen-1-aminium | |
| (1S,4aR,8aS)-N-benzyl-8a-hydroxydecahydronaphthalen-1-aminium | |
| (4aS,8aR)-4-(3,4-dihydroisoquinolin-2(1H)-yl)octahydronaphthalen-4a(2H)-ol | |
| (4aS,8aR)-4-(pyridin-3-ylamino)octahydronaphthalen-4a(2H)-ol | |
| (4R,4aS,8aR)-4-(1,3-benzodioxol-5-ylamino)octahydronaphthalen-4a(2H)-ol | |
| (4S,4aS,8aR)-4-(1,3-benzodioxol-5-ylamino)octahydronaphthalen-4a(2H)-ol | |
| (4R,4aS,8aR)-4-[(4-methylphenyl)amino]octahydronaphthalen-4a(2H)-ol | |
| (4S,4aS,8aR)-4-[(4-methylphenyl)amino]octahydronaphthalen-4a(2H)-ol | |
| (4S,4aS,8aR)-4-[(3-chlorophenyl)amino]octahydronaphthalen-4a(2H)-ol | |

TABLE A-continued

| COMPOUND | |
|---|---|
| (4aS,8aR)-4-[(2-chlorophenyl)amino]octahydronaphthalen-4a(2H)-ol | |
| (4R,4aS,8aR)-4-[(4-methoxyphenyl)amino]octahydronaphthalen-4a(2H)-ol | |
| (4S,4aS,8aR)-4-[(4-methoxyphenyl)amino]octahydronaphthalen-4a(2H)-ol | |
| (4R,4aS,8aR)-4-[(3-methoxyphenyl)amino]octahydronaphthalen-4a(2H)-ol | |
| (4S,4aS,8aR)-4-[(3-methoxyphenyl)amino]octahydronaphthalen-4a(2H)-ol | |
| (4R,4aS,8aR)-4-[(2-methoxyphenyl)amino]octahydronaphthalen-4a(2H)-ol | |
| (4S,4aS,8aR)-4-[(2-methoxyphenyl)amino]octahydronaphthalen-4a(2H)-ol | |
| 4-{[(1R,4aR,8aS)-8a-hydroxydecahydro-naphthalen-1-yl]amino}benzonitrile | |
| 4-{[(1S,4aR,8aS)-8a-hydroxydecahydro-naphthalen-1-yl]amino}benzonitrile | |
| 3-{[(1R,4aR,8aS)-8a-hydroxydecahydro-naphthalen-1-yl]amino}benzonitrile | |

TABLE A-continued

| COMPOUND | | COMPOUND | |
|---|---|---|---|
| 3-{[(1S,4aR,8aS)-8a-hydroxydecahydro-naphthalen-1-yl]amino}benzonitrile | | (4aR,8aR)-4-[(2,5-difluorophenyl)amino]octahydronaphthalen-4a(2H)-ol | |
| (4R,4aS,8aR)-4-(phenylamino)octahydronaphthalen-4a(2H)-ol | | (4aR,8aR)-4-[(2-methylpropyl)amino]octahydronaphthalen-4a(2H)-ol | |
| (4S,4aS,8aR)-4-(phenylamino)octa-hydronaphthalen-4a(2H)-ol | | (4aR,8aR)-4-(1H-indol-5-ylamino)octahydro-naphthalen-4a(2H)-ol | |
| (4aR,8aR)-4-(2,3-dihydro-1H-inden-2-ylamino)octahydro-naphthalen-4a(2H)-ol | | (4aR,8aR)-4-(pyridin-4-yl-amino)octahydro-naphthalen-4a(2H)-ol | |
| (4aR,8aR)-4-(2,3-dihydro-1H-inden-1-ylamino)octa-hydronaphthalen-4a(2H)-ol | | (4S,4aR,8aR)-4-(tetrahydro-2H-pyran-4-ylamino)octahydro-naphthalen-4a(2H)-ol | |
| | | (4R,4aR,8aR)-4-(tetrahydro-2H-pyran-4-ylamino)-octahydronaphthalen-4a(2H)-ol | |

TABLE A-continued

| COMPOUND | |
|---|---|
| (4aR,8aR)-4-(cyclopentylamino)octahydronaphthalen-4a(2H)-ol | |
| (4aR,8aR)-4-(1,2,3,4-tetrahydro-naphthalen-1-yl-amino)octahydro-naphthalen-4a(2H)-ol | |
| (4aR,8aR)-4-{[(1S,2R)-2-hydroxycyclohexyl-]amino}octahydro-naphthalen-4a(2H)-ol | |
| (4aR,8aR)-4-[(pyrimidin-5-ylmethyl)amino]octa-hydronaphthalen-4a(2H)-ol | |
| (4aR,8aR)-4-(tetrahydro-2H-pyran-3-ylamino)-octahydro-naphthalen-4a(2H)-ol | |
| (4aR,8aR)-4-[(2,2,2-trifluoroethyl)amino]octahydronaphthalen-4a(2H)-ol | |
| (4aR,8aR)-4-[(2-methylcyclohexyl)amino]octahydronaphthalen-4a(2H)-ol | |
| (4aR,8aR)-4-[(2-methoxyethyl)amino]octahydronaphthalen-4a(2H)-ol | |
| (4aR,8aR)-4[(3S,5S,7S)tricyclo[3.3.1.1$^{3,7}$]dec-1-ylamino]octahydro-naphthalen-4a(2H)-ol | |
| (4aR,8aR)-4-(2,3-dihydro-1H-inden-2-ylamino)-octahydronaphthalen-4a(2H)-ol | |
| (4aR,8aR)-4-(morpholin-4-yl)octahydronaphthalen-4a(2H)-ol | |

TABLE A-continued

| COMPOUND | |
|---|---|
| (4aR,8aR)-4-{[2-(1H-indol-3-yl)ethyl]amino}octahydronaphthalen-4a(2H)-ol | 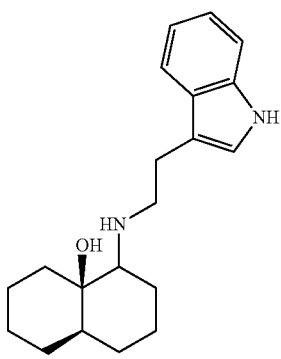 [SMILES: O[C@]12CCCC[C@@H]1CCCC2NCCc1c[nH]c2ccccc12] |
| (4aR,8aR)-4-[(2-phenylethyl)amino]octahydronaphthalen-4a(2H)-ol | 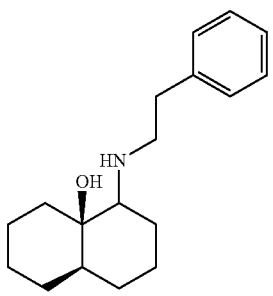 [SMILES: O[C@]12CCCC[C@@H]1CCCC2NCCc1ccccc1] |
| (4aR,8aR)-4-[(1,3-benzodioxol-5-ylmethyl)amino]octahydronaphthalen-4a(2H)-ol | 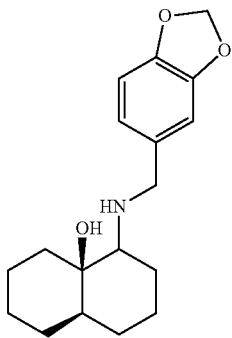 [SMILES: O[C@]12CCCC[C@@H]1CCCC2NCc1ccc2c(c1)OCO2] |
| (4aR,8aR)-4-[(1-phenylethyl)amino]octahydronaphthalen-4a(2H)-ol | 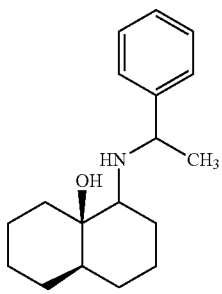 [SMILES: CC(NC1CCC[C@H]2CCCC[C@]12O)c1ccccc1] |
| (4aR,8aR)-4-(benzylamino)octahydronaphthalen-4a(2H)-ol | 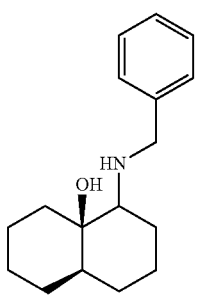 [SMILES: O[C@]12CCCC[C@@H]1CCCC2NCc1ccccc1] |
| (4aR,8aR)-4-(3,4-dihydroisoquinolin-2(1H)-yl)octahydronaphthalen-4a(2H)-ol | 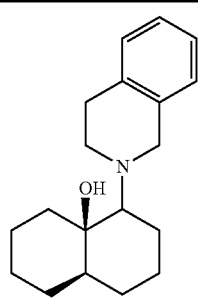 |
| (4aR,8aR)-4-(pyridin-3-ylamino)octahydronaphthalen-4a(2H)-ol | 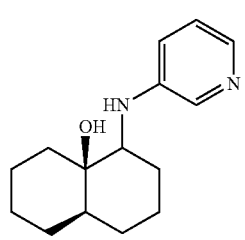 [SMILES: O[C@]12CCCC[C@@H]1CCCC2Nc1cccnc1] |
| (4aR,8aR)-4-(1,3-benzodioxol-5-ylamino)octahydronaphthalen-4a(2H)-ol | 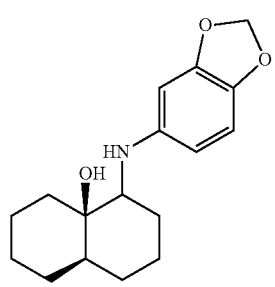 [SMILES: O[C@]12CCCC[C@@H]1CCCC2Nc1ccc2c(c1)OCO2] |
| (4aR,8aR)-4-[(4-methylphenyl)amino]octahydronaphthalen-4a(2H)-ol | 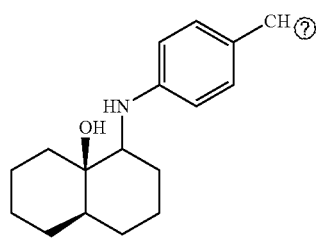 [SMILES: Cc1ccc(NC2CCC[C@H]3CCCC[C@]23O)cc1] |
| (4aR,8aR)-4-[(3-chlorophenyl)amino]octahydronaphthalen-4a(2H)-ol | 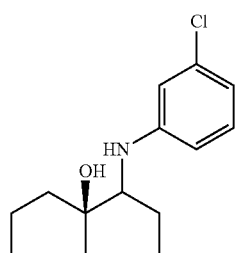 |
| (4aR,8aR)-4-[(3-chlorophenyl)amino]octahydronaphthalen-4a(2H)-ol | 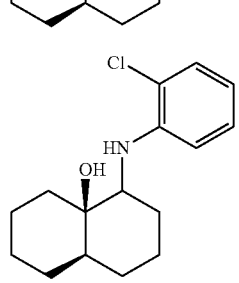 |

TABLE A-continued

| COMPOUND | |
|---|---|
| (4aR,8aR)-4-[(4-methoxyphenyl)amino]octahydronaphthalen-4a(2H)-ol | 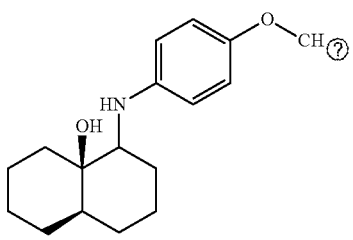 [SMILES: COc1ccc(NC2CCC[C@H]3CCCC[C@]23O)cc1] |
| (4aR,8aR)-4-[(3-methoxyphenyl)amino]octahydronaphthalen-4a(2H)-ol | 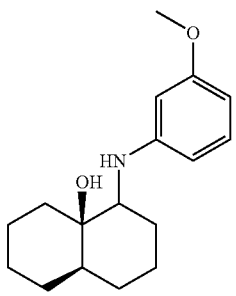 [SMILES: COc1cccc(NC2CCC[C@H]3CCCC[C@]23O)c1] |
| (4aR,8aR)-4-[(2-methoxyphenyl)amino]octahydronaphthalen-4a(2H)-ol | 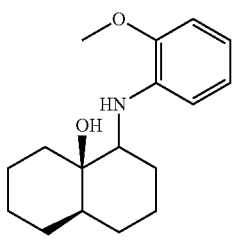 [SMILES: COc1ccccc1NC1CCC[C@H]2CCCC[C@]12O] |
| 4-{[(4aR,8aR)-8a-hydroxydecahydro-naphthalen-1-yl]amino}benzonitrile | 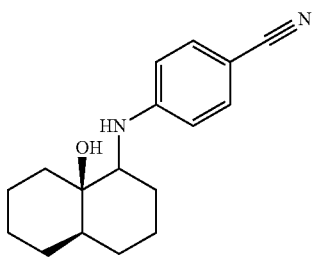 [SMILES: N#Cc1ccc(NC2CCC[C@H]3CCCC[C@]23O)cc1] |
| 3-{[(4aR,8aR)-8a-hydroxydecahydro-naphthalen-1-yl]amino}benzonitrile | 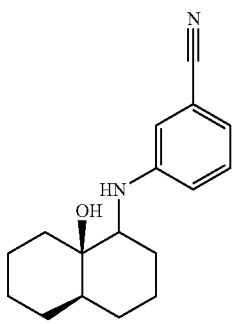 [SMILES: N#Cc1cccc(NC2CCC[C@H]3CCCC[C@]23O)c1] |

TABLE A-continued

| COMPOUND | |
|---|---|
| 2-{[(4aR,8aR)-8a-hydroxydecahydro-naphthalen-1-yl]amino}benzonitrile | 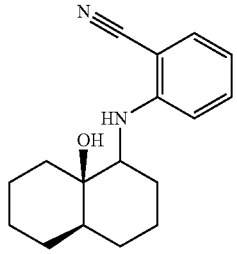 [SMILES: N#Cc1ccccc1NC1CCC[C@H]2CCCC[C@]12O] |
| 4-(phenylamino)-octahydronaphthalen-4a(2H)-ol | 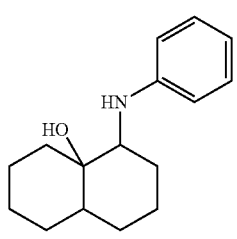 [SMILES: OC12CCCCC1CCCC2Nc1ccccc1] |
| (4aR,5S,8S,8aR)-5-[(4-fluorophenyl)-amino]-8-[(2-methoxyethoxy)methyl]hexahydro-2H-chromen-4a(5H)-ol | 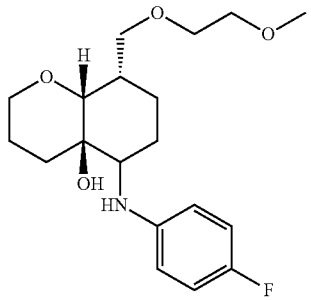 [SMILES: COCCOC[C@@H]1CCC(Nc2ccc(F)cc2)[C@]2(O)CCCO[C@H]12] | or a pharmaceutically acceptable salt thereof, or a solvate, hydrate, stereoisomer, enantiomer, oxidative metabolic or prodrug of the compound or its salt.

TABLE B

| COMPOUND | |
|---|---|
| (4aR,5S,8aR)-8-(1,3-dioxolan-2-yl)-5-[(4-fluorophenyl)amino]hexahydro-2H-chromen-4a(5H)-ol | 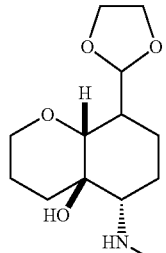 |
| (4aS,5R,8aR)-5-[(3,4-difluorophenyl)amino]hexahydro-2H-chromen-4a(5H)-ol | 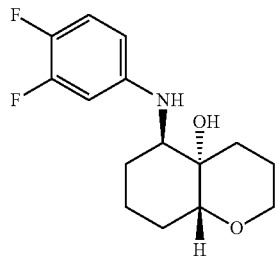 [SMILES: O[C@]12CCCO[C@@H]1CCC[C@H]2Nc1ccc(F)c(F)c1] |

TABLE B-continued

COMPOUND (4aR,5S,8aR)-5-[(4-fluorophenyl)(methyl)amino]hexahydro-2H-chromen-4a(5H)-ol (4aR,5S,8aR)-5-(phenylamino)hexahydro-2H-chromen-4a(5H)-ol (4aS,5R,8aS)-5-[(4-fluorophenyl)amino]hexahydro-2H-chromen-4a(5H)-ol (4aR,5S,8aR)-N-(4-fluorophenyl)-4a-methoxy-8-(methoxy-methyl)-N-methyl-octahydro-2H-chromen-5-amine (4aR,5S)-5-[(3,4-difluorophenyl)amino]-8-(methoxymethyl)hexahydro-2H-chromen-4a(5H)-ol (4aR,5S)-8-(methoxymethyl)-5-(phenylamino)hexahydro-2H-chromen-4a(5H)-ol (4aR,5S)-5-[(4-fluorophenyl)(methyl)amino]-8-(hydroxymethyl)-hexahydro-2H-chromen-4a(5H)-ol (4aR,5S)-8-(hydroxymethyl)-5-(phenylamino)hexahydro-2H-chromen-4a(5H)-ol (4aR,5S)-5-[(4-fluorophenyl)amino]-8-(methoxymethyl)hexahydro-2H-chromen-4a(5H)-ol

TABLE B-continued

| COMPOUND | |
|---|---|
| (4aR,5S)-8-({[tert-butyl(diphenyl)silyl]oxy}methyl)-5-[(3,4-difluorophenyl)amino]hexahydro-2H-chromen-4a(5H)-ol | |
| (4aR,5S)-5-[(4-fluorophenyl)amino]-8-(hydroxymethyl)hexahydro-2H-chromen-4a(5H)-ol | |
| (4R,4aR,8aR)-4-[(4-fluorophenyl)(methyl)amino]octahydro-4aH-isochromen-4a-ol | |
| (4aR,5R,8aS)-5-[(3,4-difluorophenyl)amino]octahydro-4aH-isochromen-4a-ol | |
| (4R,8aR,8aR)-4-[(3,4-difluorophenyl)amino]octahydro-4aH-isochromen-4a-ol | |
| (4R,4aR,8aR)-4-[(4-fluorophenyl)amino]octahydro-4aH-isochromen-4a-ol | |
| (4R,4aS,8aS)-4-[(3,4-difluorophenyl)amino]hexahydro-2H-chromen-4a(5H)-ol | |
| (4R,4aS,8aS)-4-[(4-fluorophenyl)amino]hexahydro-2H-chromen-4a(5)-ol | |
| (4aS,8R,8aR)-8-[(4-fluorophenyl)amino]hexahydro-1H-isochromen-8a(3H)-ol | |
| (4aS,8S,8aS)-8-[(4-fluorophenyl)amino]hexahydro-1H-isochromen-8a(3H)-ol | |
| benzyl ethyl({(4aR,5S,8S,8aR)-5-[(4-fluorophenyl)-amino]-4a-hydroxy-octahydro-2H-chromen-8-yl}methyl)carbamate | |

TABLE B-continued

| COMPOUND | |
|---|---|
| (4aS,5R,8S,8aR)-8-[(diethylamino)methyl]-5-[(4-fluorophenyl)amino]hexahydro-2H-chromen-4a(5H)-ol | 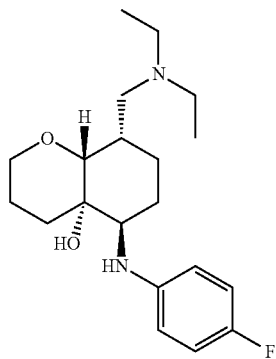 [SMILES: CCN(CC)C[C@@H]1CC[C@@H](Nc2ccc(F)cc2)[C@@]2(O)CCCO[C@H]12] |
| 1-ethyl-1-({(4aS,5R,8S,8aR)-5-[(4-fluorophenyl)amino]-4a-hydroxyoctahydro-2H-chromen-8-yl}methyl)-3,3-dimethylurea | 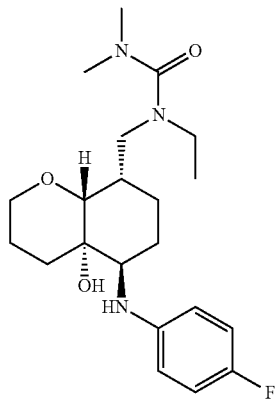 [SMILES: CCN(C[C@@H]1CC[C@@H](Nc2ccc(F)cc2)[C@@]2(O)CCCO[C@H]12)C(=O)N(C)C] |
| (4aS,5R,8aR)-5-[(4-fluorophenyl)(methyl)amino]hexahydro-2H-chromen-4a(5H)-ol | 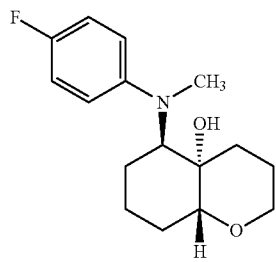 |
| (4aS,5R,8aR)-5-(phenylamino)hexahydro-2H-chromen-4a(5H)-ol | 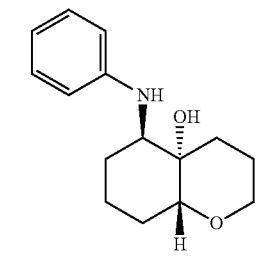 [SMILES: O[C@]12CCCO[C@@H]1CCC[C@H]2Nc1ccccc1] |
| (4aR,5S,8aR)-5-[(3,4-difluorophenyl)amino]hexahydro-2H-chromen-4a(5H)-ol | 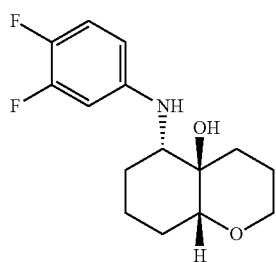 |
| (4aR,5R,8aR)-8-(dimethoxymethyl)-5-[(4-fluorophenyl)amino]hexahydro-2H-chromen-4a(5H)-ol | 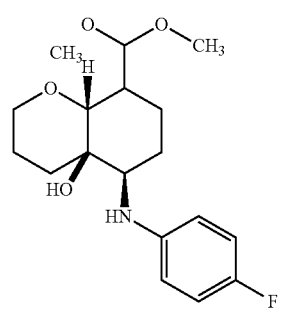 |
| (4aR,5S,8aS)-5-[(4-fluorophenyl)amino]hexahydro-2H-chromen-4a(5H)-ol | 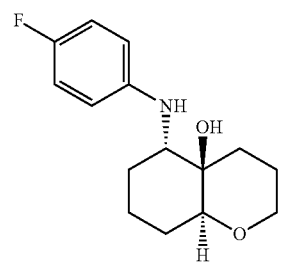 |
| (4aR,5S,8aR)-5-[(4-fluorophenyl)(methyl)amino]-8-(methoxymethyl)hexahydro-2H-chromen-4a(5H)-ol | 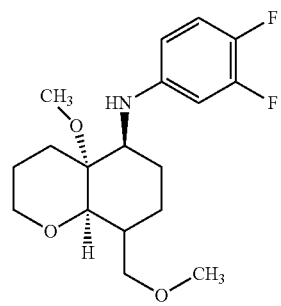 [SMILES: COCC1CC[C@H](Nc2ccc(F)c(F)c2)[C@]2(OC)CCCO[C@H]12] |
| (4aR,5S)-4a-methoxy-8-(methoxymethyl)-N-phenyloctahydro-2H-chromen-5-amine | 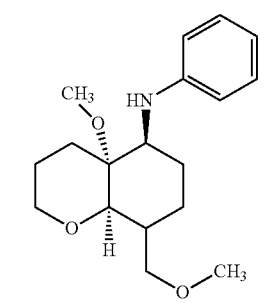 [SMILES: COCC1CC[C@H](Nc2ccccc2)[C@]2(OC)CCCO[C@H]12] |
| (4aR,5S)-N-(4-fluorophenyl)-4a-methoxy-8-(methoxymethyl)octahydro-2H-chromen-5-amine | 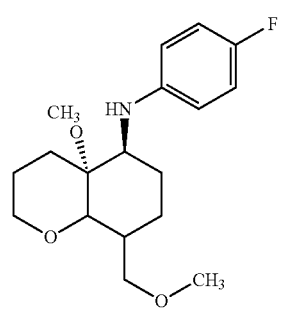 |

TABLE B-continued

| COMPOUND | |
|---|---|
| (4aR,5S)-5-[(3,4-difluorophenyl)amino]-8-(hydroxymethyl)-hexahydro-2H-chromen-4a(5H)-ol | 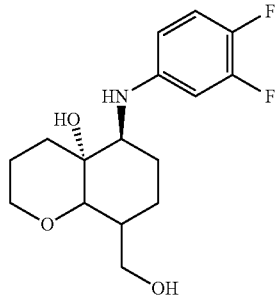 [SMILES: OCC1CC[C@H](Nc2ccc(F)c(F)c2)[C@]2(O)CCCOC12] |
| (4aR,5S)-8-({[tert-butyl-(diphenyl)silyl]oxy}methyl)-5-[(4-fluorophenyl-)amino]hexahydro-2H-chromen-4a(5H)-ol | 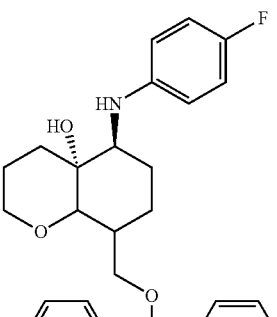 |
| (4aR,5S)-8-({[tert-butyl(diphenyl)silyl]oxy}methyl)-5-[(4-fluorophenyl)amino]hexahydro-2H-chromen-4a(5H)-ol | 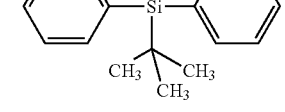 |
| (4aR,5S)-8-({[tert-butyl(diphenyl)silyl]oxy}methyl)-5-(phenylamino)hexahydro-2H-chromen-4a(5H)-ol | 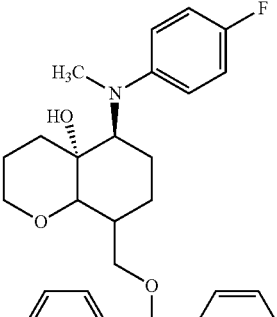 |
| (4aR,5S)-8-({[tert-butyl(diphenyl)silyl]oxy}methyl)-5-[(4-fluorophenyl)amino]hexahydro-2H-chromen-4a(5H)-ol | 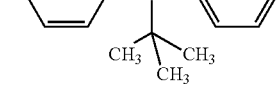 |
| (4aR,5R,8aS)-5-(phenylamino)octahydro-4aH-isochromen-4a-ol | 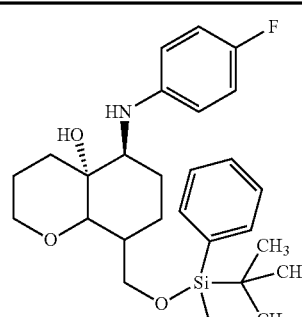 |
| (4aR,5R,8aS)-5-[(4-fluorophenyl)amino]octahydro-4aH-isochromen-4a-ol | 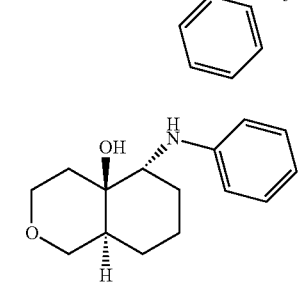 |
| (4R,4aR,8aR)-4-(phenylamino)octahydro-4aH-isochromen-4a-ol | 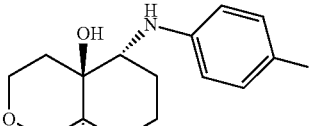 |
| (4R,4aS,8aS)-4-[(4-fluorophenyl)(methyl)amino]hexahydro-2H-chromen-4a(5H)-ol | 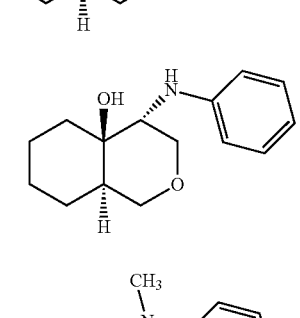 |
| (4R,4aS,8aS)-4-(phenylamino)hexahydro-2H-chromen-4a(5H)-ol | 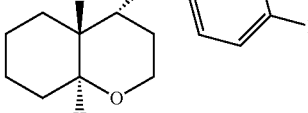 |
| (4S,4aR,8aS)-4-(4-fluorobenzyl)hexahydro-2H-chromen-4a(5H)-ol | 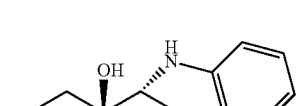 |

TABLE B-continued

| COMPOUND | |
|---|---|
| (4aS,8R,8aR)-8-[(3,4-difluorophenyl)amino]hexahydro-1H-isochromen-8a(3H)-ol | 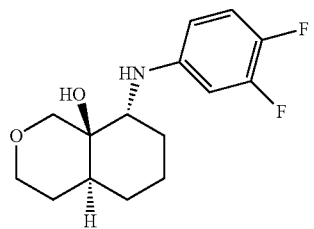 [SMILES: O[C@]12COCC[C@@H]1CCC[C@H]2Nc1ccc(F)c(F)c1] |
| (4aS,8S,8aS)-8-[(3,4-difluorophenyl)amino]hexahydro-1H-isochromen-8a(3H)-ol | 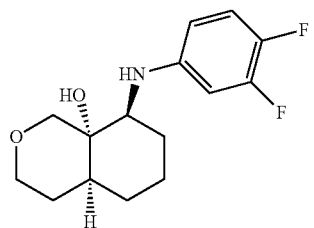 [SMILES: O[C@@]12COCC[C@@H]1CCC[C@@H]2Nc1ccc(F)c(F)c1] |
| (4aR,5S,8S,8aR)-8-[(ethylamino)methyl]-5-[(4-fluorophenyl)amino]hexahydro-2H-chromen-4a(5H)-ol | 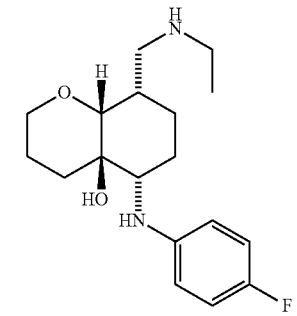 [SMILES: CCNC[C@@H]1CC[C@H](Nc2ccc(F)cc2)[C@]2(O)CCCO[C@H]12] |
| N-ethyl-N-({(4aS,5R,8S,8aR)-5-[(4-fluorophenyl)amino]-4a-hydroxyoctahydro-2H-chromen-8-yl}methyl)-2-methylpropanamide | 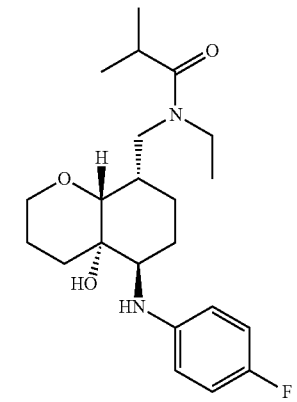 [SMILES: CCN(C[C@@H]1CC[C@@H](Nc2ccc(F)cc2)[C@@]2(O)CCCO[C@H]12)C(=O)C(C)C] |
| (4aR,5S,8S,8aR)-8-[(benzyloxy)methyl]-5-[(4-fluorophenyl)amino]hexahydro-2H-chromen-4a(5H)-ol | 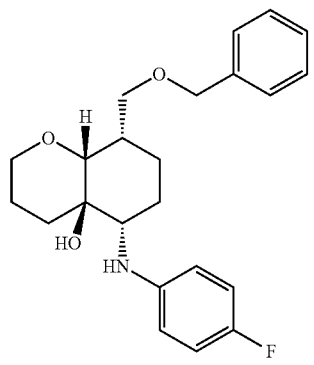 [SMILES: O[C@@]12CCCO[C@@H]1[C@H](COCc1ccccc1)CC[C@@H]2Nc1ccc(F)cc1] | or a pharmaceutically acceptable salt thereof, or a solvate, hydrate, stereoisomer, enantiomer, oxidative metabolite or prodrug of the compound or its salt.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190).

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When any variable (e.g. aryl, heterocycle, $R^{1a}$, $R^6$ etc.) occurs more than one time in any constituent, its definition on each occurrence is independent at every other occurrence. Also, combinations of substituents and/or variables are permissible only if such combinations result in stable compounds.

In addition, the compounds disclosed herein may exist as tautomers and both tautomeric folios are intended to be encompassed by the scope of the invention, even though only one tautomeric structure is depicted. For example, any claim to compound A below is understood to include tautomeric structure B, and vice versa, as well as mixtures thereof.

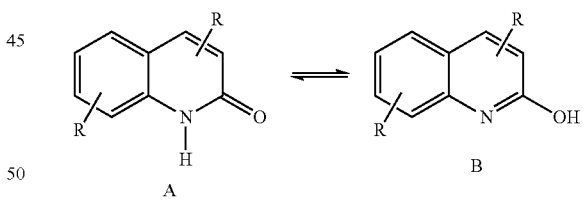

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is $C_2$-$C_6$ alkenyl.
Preferably, alkynyl is $C_2$-$C_6$ alkynyl.

As used herein, "cycloalkyl" is intended to include cyclic saturated aliphatic hydrocarbon groups having the specified number of carbon atoms. Preferably, cycloalkyl is $C_3$-$C_{10}$ cycloalkyl. Examples of such cycloalkyl elements include, but are not limited to, cyclopropyl, cyclobutyl, cyclopentyl, cyclohexyl and cycloheptyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl), benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

Preferably, heterocycle is selected from 2-azepinonyl, benzimidazolyl, 2-diazapinonyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroaryl-sulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1$-$C_6$ alkyl$)_2$, $NO_2$, CN, $(C_1$-$C_6$ alkyl$)$O—, (aryl)O—, —OH, $(C_1$-$C_6$ alkyl$)S(O)_m$—, $(C_1$-$C_6$ alkyl$)C(O)$NH—, $H_2N$—C(NH)—, $(C_1$-$C_6$ alkyl$)C(O)$—, $(C_1$-$C_6$ alkyl$)$ OC(O)—, $(C_1$-$C_6$ alkyl$)$OC(O)NH—, phenyl, pyridyl, imidazolyl, oxazolyl, isoxazolyl, thiazolyl, thienyl, furyl, isothiazolyl and $C_1$-$C_{20}$ alkyl.

As used herein "low enough pyrogen activity" with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

As used herein "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

A used herein "effective amount" of, e.g., a TRPAI antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPAI antagonist for use in the methods of the present invention, includes an amount of a TRPAI antagonist effective to decrease one or more in vitro or in vivo function of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPAI mediated ion flux.

As used herein "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to-an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

As used herein "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, trifluoro acetic, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm, Sci.*, 1977:66:1-19.

This invention further relates to a pharmaceutical composition formulated for administration in a human patient, or for veterinary use, comprising an effective amount of at least one compound of formula I or a salt thereof, or a solvate, hydrate, stereoisomer, enantiomer, oxidative metabolite or prodrug of the compound or its salt, and one or more pharmaceutically acceptable carriers. It certain aspects the compound included in the pharmaceutical composition may be active itself, or may be a prodrug, e.g., capable of being converted to an active compound in a physiological setting.

The composition may comprise, but is not limited to, one or more buffering agents, wetting agents, emulsifiers, suspending agents, lubricants, adsorbents, surfactants, preservatives and the like. The composition may be formulated as a solid, liquid, gel, ointment, or suspension for oral administration (e.g., drench, bolus, tablet, powder, capsule, mouth spray, emulsion); parenteral administration (e.g., subcutaneous, intramuscular, intraarterially, intrathecally, intracapsularly, intraorbitally, intracardiacly, intradermally, intraperitoneally, intraspinally, intravenous, epidural injection); topical application (e.g., cream, ointment, controlled-released patch, spray); intravaginal, intrarectal, transdermal, ocular, or nasal administration, or by inhalation. Thus, an aspect of this invention is a TRPA1 antagonist that is administered topically. Another aspect of this invention is a TRPA1 antagonist that is administered orally. Another aspect of this invention is a TRPA1 antagonist that is administered parentally.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately, at appropriate intervals throughout the day, optionally, in unit dosage forms.

In certain embodiments, the pharmaceutical compositions may be for use in treating or preventing a condition involving activation of TRPA1 or for which reduced TRPA1 activity can reduce the severity. In certain embodiments, the pharmaceutical compositions have a low enough pyrogen activity to be suitable for use in a human patient, or for veterinary use.

In certain aspects, a compound of the invention is combined with one or more of an analgesic, which includes, but is not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorphamol, morphine, oxycodone, oxymorphone, butorphanol, dezocine, nalbuphine, pentazocine, etodolac, indomethacin, sulindae, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid; mefanamic acid, prednisolone, and dexamethasone. Preferred analgesics are non-steroidal anti-inflammatories and opioids (preferably morphine).

In certain aspects, a compound of the invention is combined with one or more of a non-steroidal anti inflammatory, which includes, but is not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindae, apazone, phenylbutazone, aspirin, celecoxib and rofecoxib.

In certain aspects, a compound of the invention is combined with one or more of an antiviral agent which includes, but is not limited to amantadine, acyclovir, cidofovir, desciclovir, deoxyacyclovir, famciclovir, foscamet, ganciclovir, penciclovir, azidouridine, anasmycin, amantadine, bromovinyldeoxusidine, chlorovinyldeoxusidine, eytarbine, didanosine, deoxynojirimycin, dideoxycitidine, dideoxyinosine, dideoxynucleoside, edoxuidine, enviroxime, f acitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine 3-azido-3-deoxythymidine, 2',3'-dideoxyadenosine (ddA), 2',3'-dideoxyguanosine (ddG), 2',3'-dideoxycytidine (ddC), 2',3'-dideoxythymidine (ddT), 2'3'-dideoxy-dideoxythymidine (d4T), 2'-deoxy-3'-thia-cytosine (3TC or lamivudime), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2'3'-dideoxy-2',3'-didehydro-2'-fluorothymidine (Fd4T), 2'3'dideoxy-2'-beta-fluoroadenosine (F-ddA), 2'3'-dideoxy-2'-beta-fluoro-inosine (Fddl), and 2',3'-dideoxy-2'-beta-fluorocytosine (F-ddC), trisodium phosphomonoformate, trifluorothymidine, 3'azido-3'thymidine (AZT), dideoxyinosine (ddI), and idoxuridine.

In certain aspects, a compound of the invention is combined with one or more of an antibacterial agent which includes, but is not limited to, amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, framesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineonycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafeillin, neomycin, neomycin sulfate, netimicin, netilmicin sulfate, nitrofarazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, and yrothricin.

In certain aspects, a compound of the invention is combined with one or more of a cough suppressant, decongestant, or expectorant.

In certain aspects, a TRPA1 inhibitor of formula I can be used to reduce the pain and/or inflammatory effect of a retinoid by combining a retinoid with the subject TRPAI inhibitor. Retinoids include, but are not limited to, compounds such as retinoic acid (both cis and trans), retinol, adapalene, vitamin A and tazarotene. Retinoids are useful in treating acne, psoriasis, rosacea, wrinkles and skin cancers and cancer precursors such as melanoma and actinic keratosis.

In other aspects, the TRPAI inhibitors of formula I can be combined with keratolytic agents, which include benzoyl peroxide, alpha hydroxyacids, fruit acids, glycolic acid, salicylic acid, azelaic acid, trichloroacetic acid, lactic acid and piroctone.

The TRPA1 inhibitors of formula I can also be combined with depilatory agents (hair loss), anti-acne agents, anti-eczema agents and anti-psoratic agents. Compounds particularly useful in treating acne include azelaic acid (an aliphatic diacid with antiacne properties), anthralin (a diphenolic compound with antifungal and antipsoriatic properties), and inasoprocol (nordihydroguaiaretic acid, a tetraphenolic compound with antioxidant properties, also useful in the treatment of actinic keratosis) and analogs thereof (such as austrobailignan 6, oxoaustrobailignan 6, 4'-O-methyl-7,7'-dioxoaustrobailignan 6, macelignan, demethyldihydroguaiaretie acid, 3,3',4-trihydroxy-4'-methoxylignan. Saururenin, 4-hydroxy-3,3',4'-trimethoxylignan, and isoanwulignan). Anti-eczema agents include, pimecrolimus and tacrolimus. Anti-psoriatic active agents suitable for use in the present invention include retinoids (including isomers and derivatives of retinoic acid, as well as other compounds that bind to the retinoic acid receptor, such as retinoic acid, acitretin, 13-cis-retinoic acid (isotretinoin), 9-cis-retinoic acid, tocopheryl-retinoate (tocopheirol ester of retinoic acid (trans- or cis-)), etretinate, motretinide, 1-(13-cis-retinoyloxy)-2-propanone, 1-(13-cis-retinoyloxy)-3decanoyloxy-2-propanone, 1,3-bis-(13-cis-retinoyloxy)-2-propanone, 2-(13-cisretinoyloxy)-acetophenone, 13-cis-retinoyloxymethyl-2,2-dimethyl propanoate, 2(13-cis-retinoyloxy)-n-methyl-acetamide, 1-(13-cis-retinoyloxy)-3-hydroxy-2propanone, 1-(13-cis-retinoyloxy)-2,3-dioleoylpropanone, succinimdyl 13-cis retinoate, adapalene, and tazarotene), salicylic acid (monoammonium salt), anthralin, 6-azauridine, vitamin D derivatives (including but not limited to Rocaltrol (Roche Laboratories), EB 1089 (24a,26a,27a-trihomo-22,24-diene-1a,25-(OH)2 D3), KH 1060 (20-epi-22-oxa-24a,26a,27a-trihomo-1a,25-(OH)-2-D3), MC 1288, GS1558, CB 1093, 1,25-(OH)2-16-ene-D3, 1,25-(OH)2-16-ene-23-yne-D3, and 25(OH)2-16-ene-23-yne-D3, 22-oxacalcitriol; Ia-(OH)D5 (University of Illinois), ZK 161422 and ZK 157202 (Institute of Medical Chemistry-Schering AG), alfacalcidol, calcifediol, calcipotriol (calcipotriene), maxacalcitriol, colecalciferol, doxercalciferol, ergocalciferol, falecalcitriol, lexacalcitol, maxacalcitol, paricalcitol, secalciferol, seocalcitol, tacalcitol, calcipotriene, calcitriol, and other analogs as disclosed in U.S. Pat. No. 5,994,332), pyrogallol, and tacalcitol.

The compounds of formula I can also be combined with vitamins and derivatives thereof including Vitamin A, ascorbic acid (Vitamin C), alphatocopherol (Vitamin E), 7-dehydrocholesterol (Vitamin D), Vitamin K, alpha-lipoic acid, lipid soluble anti-oxidants, and the like. The subject TRPAI inhibitors can also be used with skin protectants, such allantoin and esculin.

When two or more compounds of the invention are combined the two or more compounds may have a similar selectivity profile and functional activity, or they may have a different selectivity profile and functional activity. By way of example, the two or more compounds may both be approximately 10, 100, or 1000, fold selective for antagonizing a function of TRPA1 over TRPV1, TRPV5, and TRPV6 (e.g., the two or more compounds have a similar selectivity profile), and further may inhibit a function of TRPA1 with a similar IC50 (e.g., a similar functional activity). Alternatively, the one of the two or more compounds may selectively inhibit TRPAI while the other of the two or more compounds inhibits both TRPAI and TRPV 1 (e.g., the two or more compounds have differing selectivity profiles). Administration of combinations of two or more compounds of the invention having similar or differing properties are included within this invention.

In certain aspects, a compound of formula I is combined with one or more additional compounds that antagonize the function of a different channel. For example, a compound of formula I may be combined with one or more additional compounds that that antagonize TRPV 1, TPRM8, and/or TRPV3. The additional compounds that antagonize TRPV1 or TRPV3 may cross react with other TRP channels.

When the compounds of formula I are combined with other TRP agents and/or additional active agents such as antibacterials (e.g., penicillins, cephalosporins), antivirals, and the like, the combination includes simultaneous, sequential and separate administration of the active compounds in a way that the therapeutic effects of the first administered compound is still detectable when the subsequent therapy is administered.

TRPA1 antagonists of the subject invention can be used as part of a prophylaxis or treatment for a variety of disorders and conditions, including, but not limited to, acute and chronic pain, touch sensitivity, burns, inflammation, fibromyalgia, diabetic neuropathy, pain associated with a deiuiatological disease or disorder, e.g., psoriasis and basal cell and squamous cell eariconomas, eczema, dermatitis, post-herpetic neuralgia (shingles), migraine, incontinence, fever, hot flashes, osteoarthritis, oral mucositis, a neurodegenerative disease or disorder, e.g., Alzheimer's disease (AD), Parkinson's disease, Huntington's disease, amyotrophic lateral sclerosis (ALS), and other brain disorders caused by trauma or other insults including aging, an inflammatory disease (e.g., asthma, chronic obstructive pulmonary disease, rheumatoid arthritis, osteoarthritis, inflammatory bowel disease, glomerulonephritis, neuroinflammatory diseases, multiple sclerosis, and disorders of the immune system), cancer pain (e.g. liposarcoma) or other proliferative disease, kidney disease and liver disease, a metabolic disorder such as diabetes; bladder cystits, oral pain (e.g. canker sores, aphthous ulcers, gingivostomatitis, etc.), pancreatic pain, pain associated with Crohn's disease and Irritable Bowel Syndrome (IRS), rheumatoid arthritis, Grierson-Gopalan syndrome (better known as burning feet syndrome), burning mouth syndrome (BMS), Complex Regional Pain Syndrome (CRPS; also known as chronic regional pain syndrome), and cough, or is used as a depilatory to promote loss of or inhibit the growth of hair on a patient. Further diseases and conditions include post-surgical pain, post herpetic neuraligia, incontinence; and shingles.

Blockers of voltage-gated calcium channels belong to a class of medications originally developed to treat hypertension. Such blockers inhibit the movement of calcium into the muscle cells of the heart and arteries. Because-calcium is needed for these muscles to contract, such blockers lower blood pressure-by decreasing the force of cardiac contractile response and relaxing the muscle walls of the arteries. Although TRPAI is not a voltage-gated calcium channel, it is still instrumental in regulating calcium homeostasis, as well as the balance of other ions, in cells and tissues. Accordingly, TRPA I antagonists of the invention may be used to treat hypertension. Additional uses of the subject compounds include other conditions that may be ameliorated, in whole or in part, by relaxing the muscle walls of blood vessels. Exemplary conditions include headaches and migraine attacks.

Other exemplary diseases or conditions that can be treated using a TRPA1 antagonist of the present invention are detailed throughout the specification. Thus, the present invention relates to the use of the compounds of formula I in the treatment of or to reduce the symptoms of any of the diseases or conditions disclosed in the application. The invention further contemplates the use of the compounds of formula I in the manufacture of a medicament or pharmaceutical preparation to treat or reduce the symptoms of any of the diseases or conditions provided herein. Compounds for use in treating a particular disease or condition can be formulated for administration via a route appropriate for the particular disease or condition.

TRPA1 antagonists can be administered alone or in combination with other therapeutic agents. For instance, the TRPA1 antagonists of the claimed invention can be combined with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

Another aspect of the present invention relates to a method for treating or preventing a condition involving activation of TRPA1 or for which reduced TRPA1 activity can reduce the severity by administering a TRPA1 antagonist that inhibits TRPA1-mediated current and/or TRPA1-mediated ion flux.

Another aspect of the present invention relates to a TRPA1 inhibitor that is used to treat or ameliorate pain. Exemplary classes of pain that can be treated using a TRPA1 inhibitor include, but are not limited to nociceptive pain, inflammatory pain, and neuropathic pain. Pain that can be treated with a TRPA1 inhibitor can be chronic or acute. Thus, in another aspect of the invention the TRPA1 antagonist of formula I is administered to prevent, treat or alleviate signs and symptoms of acute pain, chronic pain, touch sensitivity, itching sensitivity, or as part of treating a burn, such as, for example, post-surgical pain, cancer pain, or neuropathic pain. Still in another aspect of the invention a compound of formula I is administered to prevent, treat or alleviate signs and symptoms of migraine.

In another aspect of the invention a compound of formula I is administered to prevent, treat or alleviate signs and symptoms of a disorder or condition selected from the group consisting of diabetic neuropathy, inflammation, psoriasis, eczema, dermatitis, post-herpetic neuralgia (shingles), incontinence, bladder incontinence, fever, hot flashes, pancreatitis, chronic regional pain syndrome, Fabray's disease, and cough. In another aspect of the invention a compound of formula I is administered to prevent, treat or alleviate signs and symptoms of osteoarthritis. In another aspect of the invention a compound of formula I is administered to prevent, treat or alleviate signs and symptoms of rheumatoid arthritis. In another aspect of the invention a compound of formula I is administered to prevent, treat or alleviate signs and symptoms of oral mucositis. In another aspect of the invention a compound of formula I is administered to promote loss of or inhibit the growth of hair on a patient. In another aspect of the invention a compound of formula I is used to treat or ameliorate the symptoms of incontinence.

Because of the important role that calcium regulation plays in many cellular processes including cellular activation, gene expression, cellular trafficking and apoptotic cell death, calcium dyshomeostasis is implicated in the many diseases and disorders involving such cellular activities. These diseases and disorders include dermatological diseases and disorders; neurological and neurodegenerative diseases and disorders; fever associated with various diseases, disorders or conditions; incontinence; inflammatory diseases and disorders such as inflammatory bowel disease and Crohn's disease; respiratory diseases and disorders such as chronic cough, asthma and chronic obstructive pulmonary disease (COPD); digestive disorders such as ulcers and acid reflux; metabolic diseases and disorders including obesity and diabetes; liver and kidney diseases and disorders; malignancies including cancers; aging-related disorders; and sensitivity to pain and touch.

Additional diseases or conditions that can be treated include ATP-related diseases or disorders including epilepsy, cognition, emesis, pain (e.g., migraine), asthma, peripheral vascular disease, hypertension, immune and inflammatory conditions, irritable bowel syndrome, cystitis, depression, aging-associated degenerative diseases, urinary incontinence, premature ejaculation, cystic fibrosis, diabetes, contraception and sterility, and wound healing (see, for example, Foresta et al. (1992) T. Biol. Chem. 257:19443-19447; Wang et al. (1990) Bioehirn. Biophys. Res. Commun. 166:251-258; Burnstock and Williams, (2000) J. Pharmacol. Exp. Ther. 295: 862-869; and Burnstock, Pharmacol Rev (2006) 58; 58-86).

In still another aspect of the invention the TRPA 1 inhibitor is non-narcotic and has little or no narcotic side-effects. Thus, the TRPA1 inhibitor can be used to treat or ameliorate pain with fewer side-effects than narcotic pain relievers. Exemplary side-effects that may be substantially absent at effective dosages of TRPV3 inhibitors include one or more of exopthalmos, catalepsy, disruption of gut motility, and inhibition of sensation in non-injured areas of the body.

In other aspects of the invention, a TRPA1 inhibitor used in the treatment of any of the diseases or indications disclosed herein has one or more of the structural or functional characteristics disclosed herein. TRPA1 inhibitors described herein can be used in the treatment of any of the foregoing or following diseases or conditions, including in the treatment of pain associated with any of the foregoing or following diseases or conditions. When used in a method of treatment, an inhibitor can be selected and formulated based on the intended route of administration. Inhibitors can be used to treat the underlying disease or condition, or to relieve a symptom of the disease or condition. Exemplary symptoms include pain associated with a disease or condition.

The present invention provides methods for treating pain that include administration of (i) antagonists of a TRPA1 function; (ii) combinations of selective antagonists of a TRPA1 function and selective antagonists of TRPV1 and/or TRPV3 function; or (iii) a pan-TRP inhibitor that inhibits a function of two or more of TRPA1, TRPV1, and TRPV3.

In addition to TRPV family members, other TRP channels have been implicated in pain reception and/or sensation. For example, certain TRPM channels including TRPMB have been implicated in the reception and/or sensation of pain. Accordingly, in certain embodiments, the methods of the present invention include treating pain by administering (i) a combination of a selective TRPAI antagonist and a selective TRPMB antagonist; (ii) a combination of a selective TRPA1 antagonist, a selective TRPMB antagonist, and one or more of a selective TRPV I, and/or TRPV3 antagonist; (iii) a cross-TRP inhibitor that antagonizes a function of TRPAI and TRPM8; or (iv) a pan inhibitor that antagonizes a function of TRPA1, TRPM8, and one or more of TRPV1 and TRPV3.

In another aspect of the present invention there is provided the use of a TRPA1 inhibitor in the manufacture of a medicament for treating or preventing a condition involving activation of TRPA1 or for which reduced TRPAI activity can reduce the severity, wherein the TRPAI inhibitor is represented by the compound of formula I, or a pharmaceutically acceptable salt thereof, or a solvate, hydrate, oxidative metabolite or prodrug of the compound or its salt).

In some aspects of the invention, the compounds can be used to inhibit a TRPA1 mediated current and/or TRPA1-mediated ion flux in vitro, for example in cells in culture. In some embodiments, the compounds can be used to inhibit a TRPA1 mediated current in vivo. In certain embodiments, the compounds inhibit both an inward and an outward TRPA1-mediated current. In certain embodiments, the compounds inhibit a TRPA1 mediated ion flux in vitro, for example in cells in culture. In certain other embodiments, the compounds inhibit a TRPA1 mediated influx in vivo.

The invention contemplates pharmaceutical compositions and uses of TRPA1 antagonists having any combination of the foregoing or following characteristics, as well as any combination of the structural or functional characteristics of the TRPA1 antagonists described herein. Any such antagonists or preparations can be used in the treatment of any of the diseases or conditions described herein. Any such antagonists or preparations can be used to inhibit a function of TRPA1, for example a TRPA1-mediated current and/or a TRPA1-mediated ion flux.

Abbreviations used in the description of the chemistry and in the Examples that follow are:
$CH_2Cl_2$ dichloromethane
Boc tert-butoxycarbonyl
DIEA diisopropylethylamine
PMB 4-methoxy-benzyl
PMBBr 4-methoxy-benzyl bromide
THF tetrahydrofuran
TFA trifluoroacteic acid.
MeOH methanol
PS-PPh$_3$ polystyrene triphenyphosphine
DMF N,N-dimethylformamide
DMA N,N-dimethylacetamide
EtOAc ethyl acetate
RT/ml room temperature
AD Alzheimer's Disease
NMR Nuclear Magnetic Resonance
DMSO dimethyl sulfoxide Several methods for preparing the compounds of this invention are illustrated in the following Schemes and Examples. Starting materials and the requisite intermediates are in some cases commercially available, or can be prepared according to literature procedures or as illustrated herein.

The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. The compounds of this invention may be purified by the standard purification methods such as normal phase chromatography, HPLC, Chiral HPLC, SFC and other methods that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Synopsis of Reaction Schemes

General Reaction Scheme I

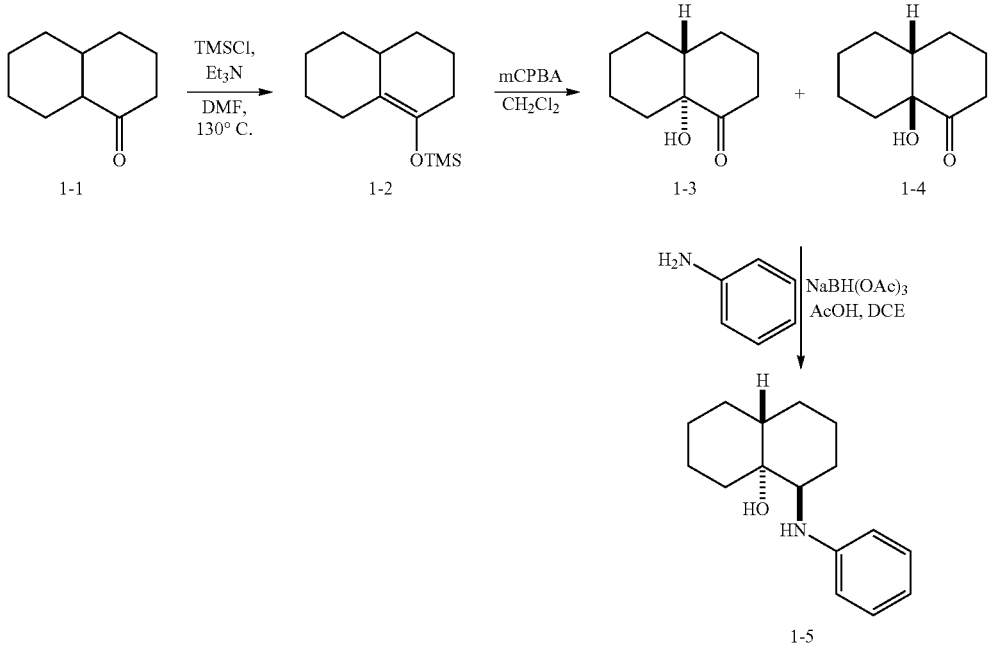

Reaction Scheme I illustrates the preparation of the compounds of the instant invention, starting with a commercially available decalone I-1. This material can be converted to the corresponding TMS enolether I-2. Intermediate I-2 reacts with in CPBA followed by aqueous work up to produce ketone alcohols I-3 and I-4. I-3 and I-4 can then undergo reductive amination, in parallel, with a diverse array of amines to provide I-5 and I-6.

General Reaction Scheme II

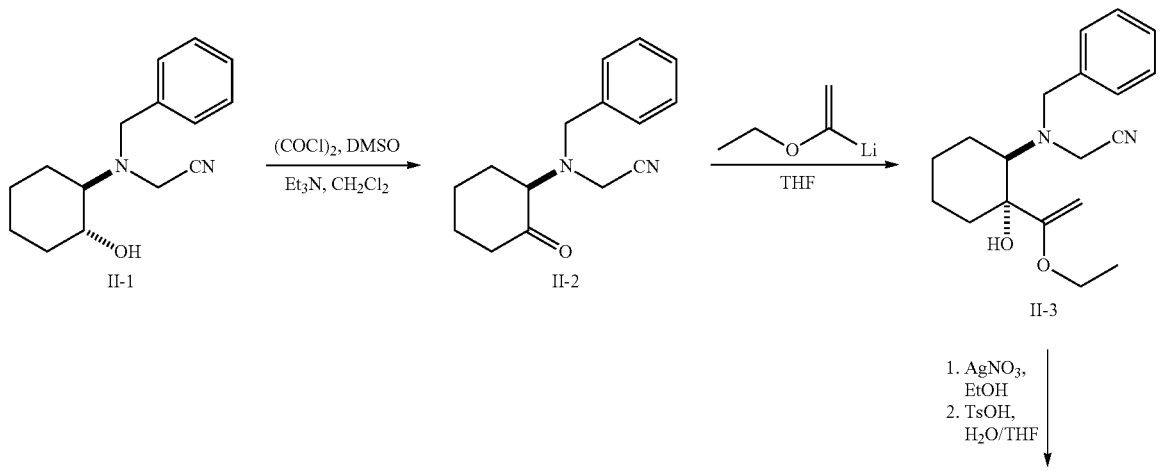

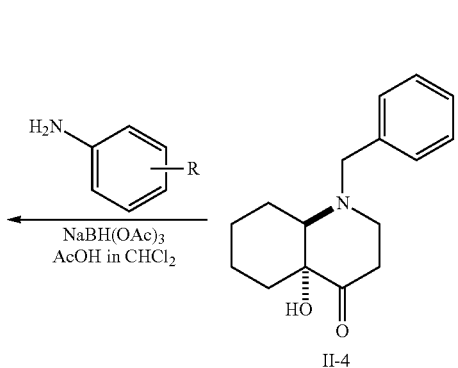
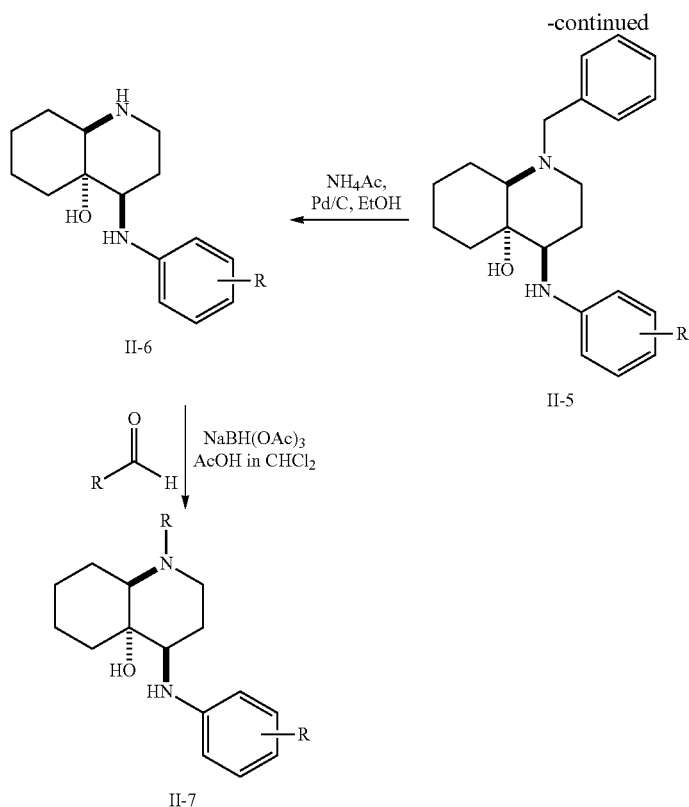

Reaction Scheme II depicts the synthesis of the compounds of the instant invention, starting with aminoalcohol II-1 which is prepared according to literature (Jacobsen, E.; Levin, J.; Overman, L. *J. Am. Chem. Soc.* 1988, 110, 4329). II-1 was subjected to Swern oxidation condition to give ketone II-2 which was treated with lithiated ethylvinylether in THF to afford tertial alcohol II-3. Treatment of AgNO$_3$ in Ethanol followed by acidic hydrolysis produces oxocyclohexapiperidine product II-4. Reductive amination with various anilines affords aminopiperidine II-5 which, upon hydrogenation, affords piperidine II-6. II-6 can then undergo reductive amination, in parallel, with a diverse array of amines to provide II-7.

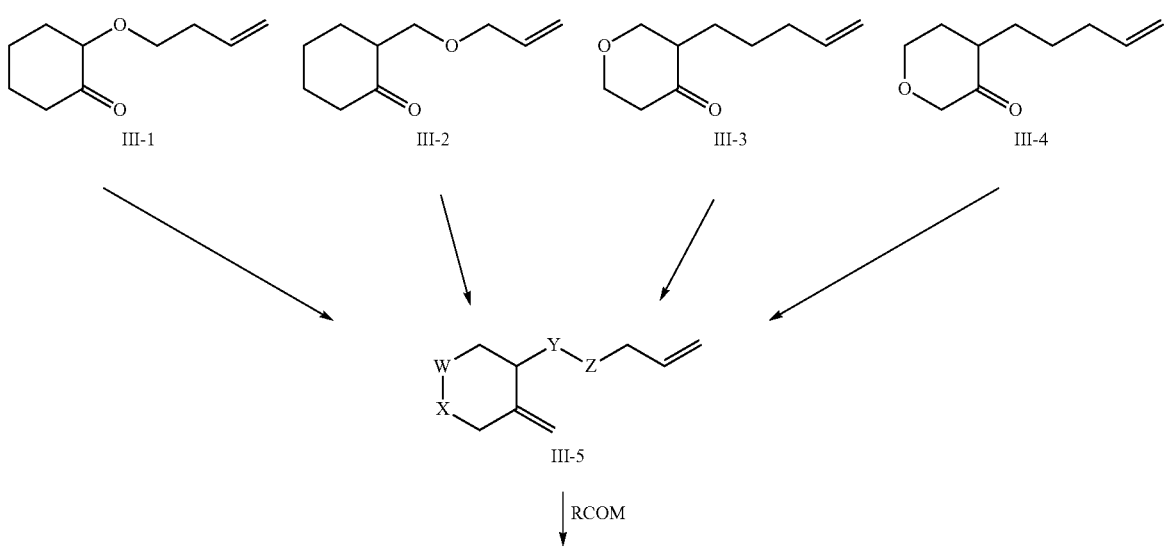

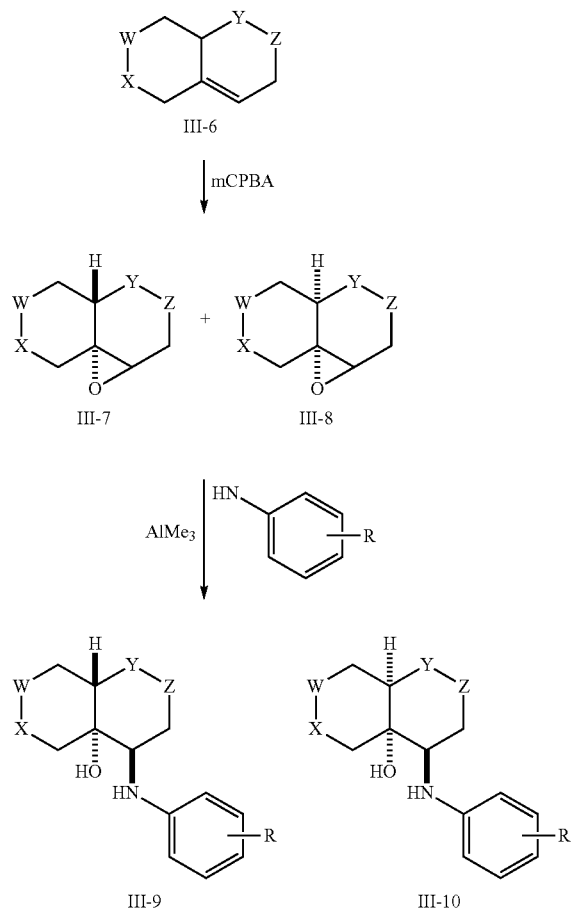

Reaction Scheme III depicts the synthesis of compounds of the instant invention, starting with cyclohexanone (III-1 and III-2) or pyranone (III-3 and III-4), all of which requires multiple step synthesis from commercially available starting material (their synthesis are detailed in the example section). Olefination via Wittig reaction provides dialkene III-5 (W, X, Y, Z represents oxygen in each individual substrate) which undergoes a standard ring-closure-olefine-metathesis to provide III-6. III-6 is then treated with mCPBA to give epoxides III-7 and III-8. III-6 and III-7 can then undergo epoxide opening reaction, in parallel, with a diverse array of amines in the presence of $AlMe_3$ to provide III-8 and III-9 respectively.

General Reaction Scheme IV

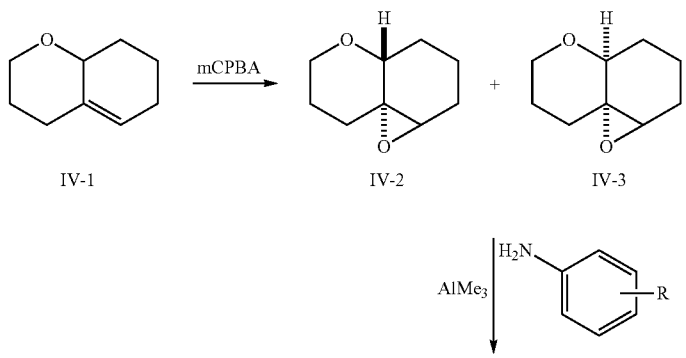

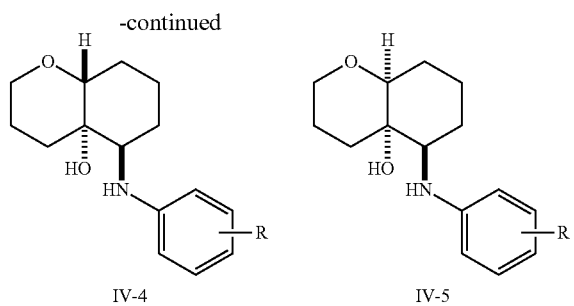

Reaction Scheme IV depicts the synthesis of the compounds of the instant invention, starting with hexahydrochromene IV-1 which is prepared according to literature (Yeh, P. M.; Lee, Y-C; Young, T-C. *Synthesis* 2006, 21, 3621). IV-1 is treated with mCPBA to give epoxides IV-2 and IV-3. IV-2 and IV-3 can then undergo epoxide opening reaction, in parallel, with a diverse array of amines in the presence of AlMe$_3$ to provide IV-4 and IV-5 respectively.

General Reaction Scheme V

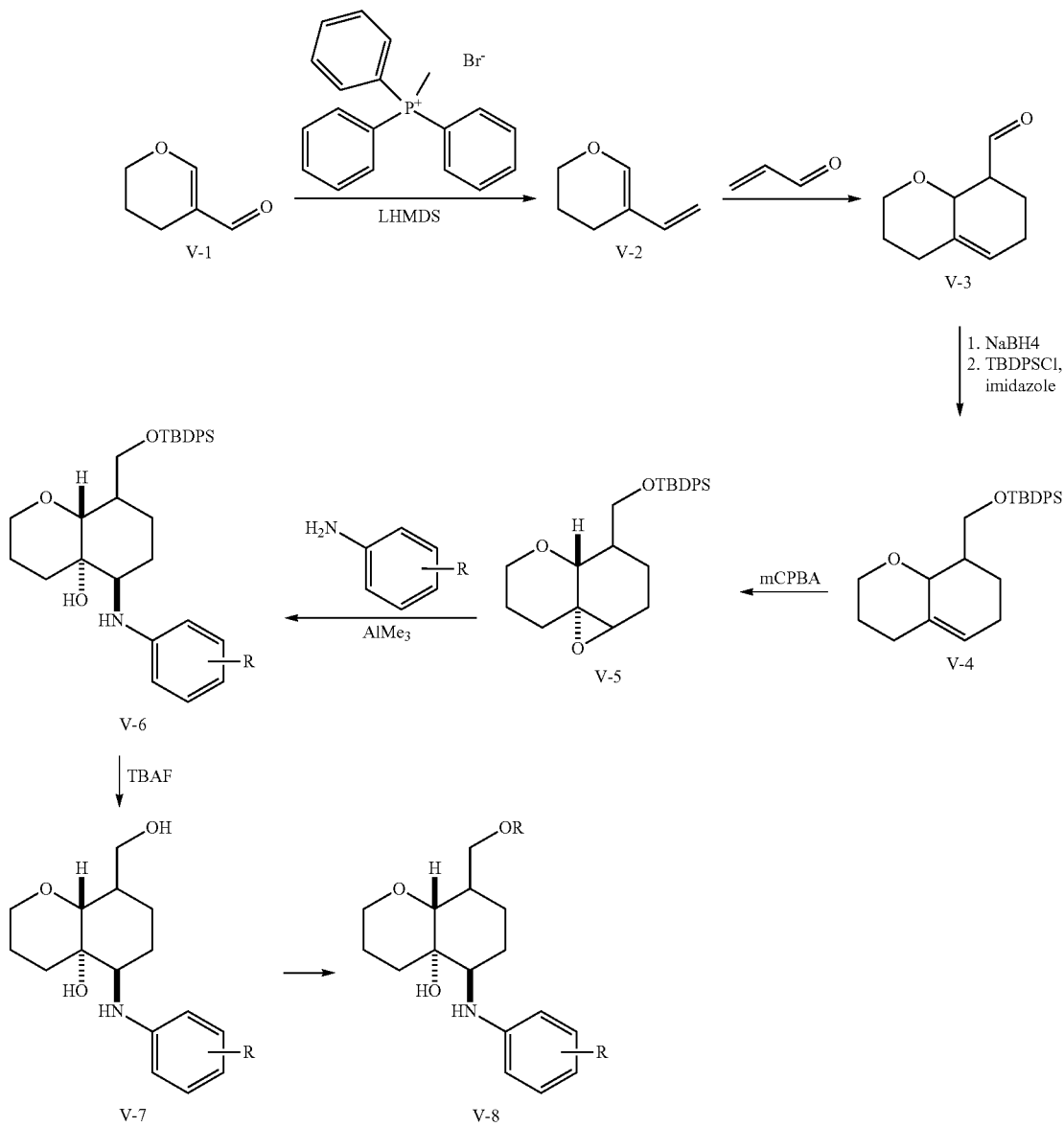

Reaction Scheme V illustrates the preparation of the compounds of the instant invention, starting with a commercially available pyran-5-carbaldehyde V-1. This material can be converted to the corresponding olefin V-2 via a Wittig reaction. Diels-alder reaction between V-2 and acrolein provides aldehyde V-3 which was reduced by sodium borohydride and the ensuing alcohol is protected as its tert-butyldiphenylsilyl ether V-4. V-4 is treated with mCPBA to give epoxides V-5 which then undergo epoxide opening reaction, in parallel, with a diverse array of amines in the presence of AlMe₃ to provide V-6. TBAF treatment to remove the silyl protecting group provides alcohol V-7 which is then converted via alkylation, in parallel, with a diverse array of alkylating reagents to provide V-8.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the compounds depicted in the following Tables are either commercially or are readily prepared by one of ordinary skill in the art.

Example 1

(4R,4aR,8aR)-4-(phenylamino)octahydronaphthalen-4a(2H)-ol

Trimethyl(2,3,4,4a,5,6,7,8-octahydronaphthalen-1-yloxy)silane (1-2)

To Decalone (2500 mg, 16.42 mmol) and triethylamine (5.49 ml, 39.4 mmol) in DMF (6.569 ml) at room temperature was added TMS-Cl (2.52 ml, 19.71 mmol) and the reaction mixture was heated to 130° C. and stirred for 3 days. The mixture was cooled, diluted with ether (50 mL) and washed with aqueous sodium hydrogen carbonate. The aqueous layer was extracted with diethyl ether. The combined organic fractions were washed with brine, dried, filtered and the solvent was evaporated under reduced pressure. The residue was purified by column chromatography on silica gel to give the title compound as a colorless liquid.

(4aR,8aR)-8a-hydroxyoctahydronaphthalen-1(2H)-one (1-3) and (4aR,8aS)-8a-hydroxyoctahydronaphthalen-1(2H)-one (1-4)

To trimethyl(2,3,4,4a,5,6,7,8-octahydronaphthalen-1-yloxy)silane (1310 mg, 5.84 mmol) in dichloromethane (18.700 ml) was added mCPBA (1209 mg, 7.00 mmol) portion-wise at 0° C. The reaction mixture was then allowed to warm up to RT and stirred for 1 hr. The mixture was cooled and quenched with saturated aqueous Na₂SO₃. The mixture was then diluted with CH₂Cl₂ (50 mL) and washed with aqueous sodium hydrogen carbonate (saturated, 20 mL) The aqueous layer was extracted with dichloromethane (3×30 mL). The combined organic fractions were washed with brine (saturated, 20 mL), dried, filtered and the solvent was evaporated under reduced pressure. The residue was purified by column chromatography on silica gel to give the title compound 1-3 and the title compound 1-4 as colorless liquids. ¹H-NMR (500 MHz, CDCl₃) 1-3: δ 3.02 (m, 1H), 2.22 (m, 1H), 2.03 (m, 1H), 1.38-1.80 (m, 12H), 1.22 (m, 1H); 1-4: δ 3.76 (bs, 1H), 2.58 (m, 1H), 2.45 (m, 1H), 2.10 (m, 1H), 1.90-2.02 (m, 3H), 1.45-1.85 (m, 8H), 1.30 (m, 1H);

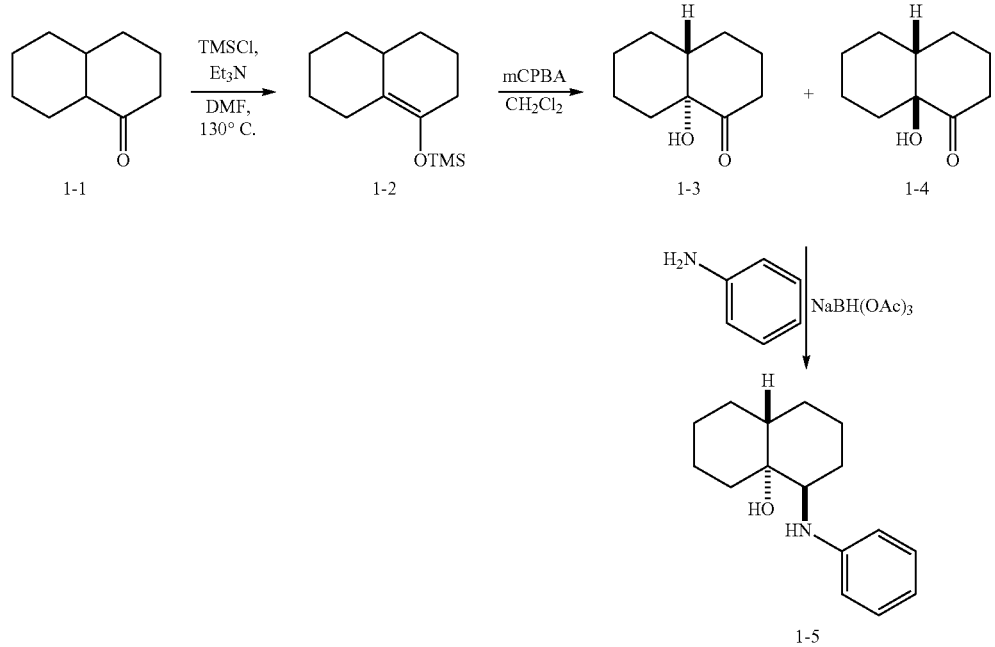

Scheme I

(4R,4aR,8aR)-4-(phenylamino)octahydronaphthalen-4a(2H)-ol (1-5)

A mixture of (4aR,8aR)-8a-hydroxyoctahydronaphthalen-1(2H)-one (0.339 g, 2.015 mmol) and aniline (0.552 mL, 6.05 mmol) in 2% $CH_3COOH$ in ACE (20 mL) was stirred for 1 hr at rt. Sodium triacetoxyborohydride (1.37 g, 6.45 mmol) was then added and the mixture was stirred for several hours. The mixture was then quenched with sat'd. aq. $NaHCO_3$ and extracted 3× with $CH_2Cl_2$. The combined organics were dried, filtered, and concentrated. The residue was purified by column chromatography on silica gel to give the title compound. $^1$H NMR (500 MHz, $CDCl_3$) δ 7.12-7.18 (m, 2H), 6.60-6.69 (m, 3H), 1.96-2.04 (m, 1H), 1.73-1.81 (m, 1H), 1.64-1.70 (m, 2H), 1.18-1.60 (m, 12H). HRMS (ES) m/z M+H calc'd: 246.1852. found: 246.1850.

TABLE 1

| # | Structure | MS M + 1 |
|---|-----------|----------|
| 1-6 | | 264.1747 |
| 1-7 | | 282.1665 |
| 1-8 | | 322.2162 |
| 1-9 | 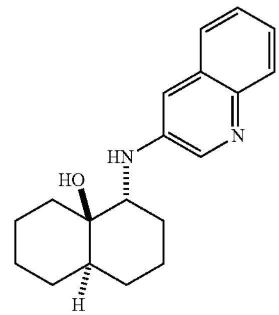 [SMILES: O[C@]12CCCC[C@@H]1CCC[C@H]2Nc1cnc2ccccc2c1] | 297.1958 |
| 1-10 | 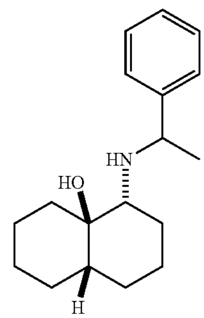 [SMILES: CC(N[C@@H]1CCC[C@@H]2CCCC[C@@]21O)c1ccccc1] | 274.2165 |
| 1-11 | 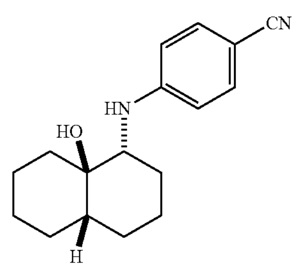 [SMILES: N#Cc1ccc(N[C@@H]2CCC[C@@H]3CCCC[C@@]32O)cc1] | 271.2 |
| 1-12 | 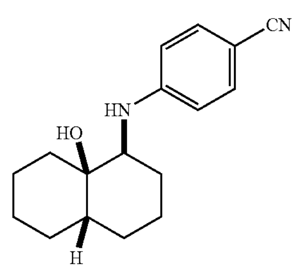 [SMILES: N#Cc1ccc(N[C@H]2CCC[C@@H]3CCCC[C@@]32O)cc1] | 271.2 |

Example 2

(4R,4aS,8aR)-1-ethyl-4-(phenylamino)octahydro-quinolin-4a(2H)-ol

Example Scheme 2

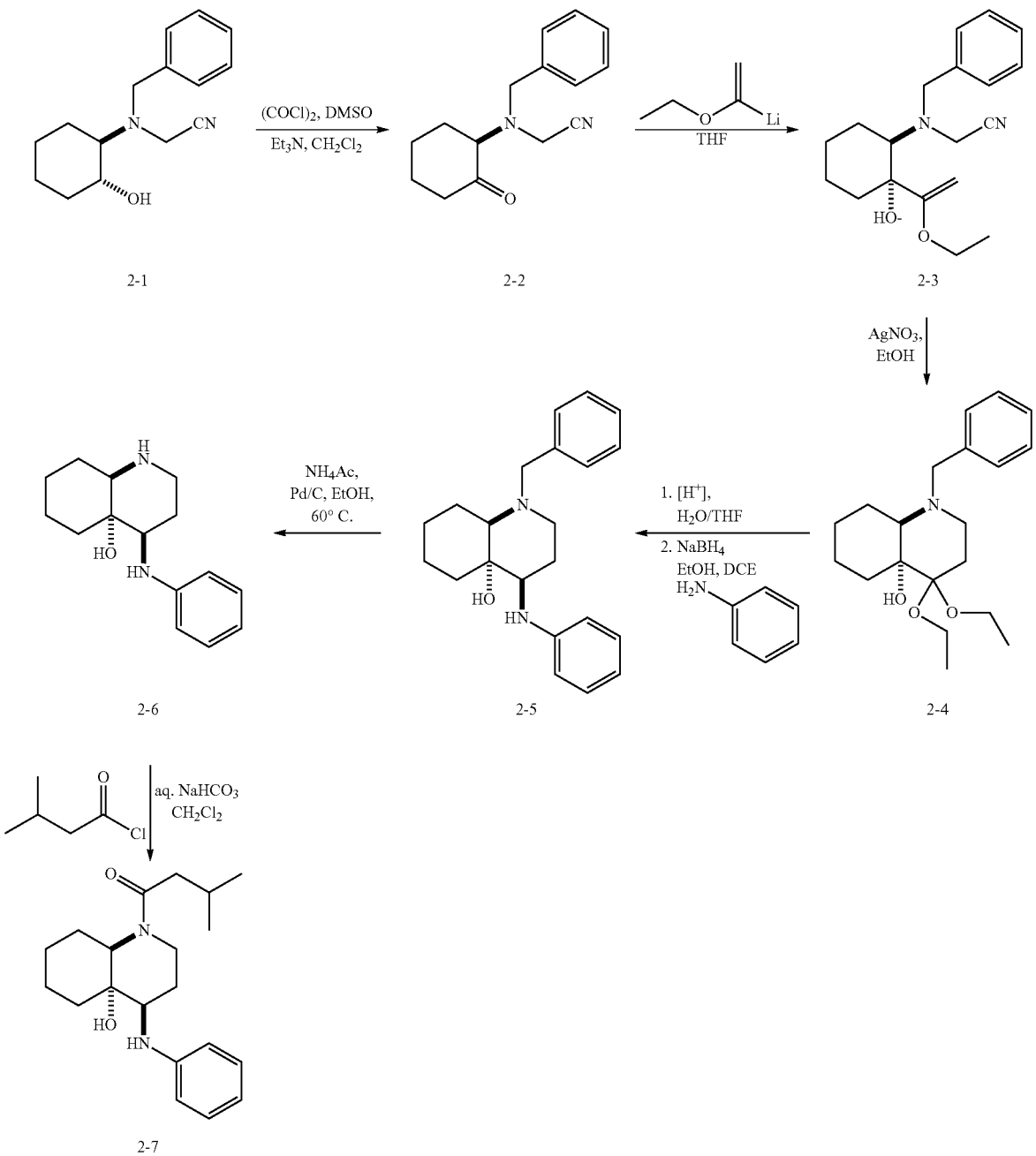

{Benzyl[(1R)-2-oxocyclohexyl]amino}acetonitrile (2-2)

To oxalyl chloride (1,842 ml, 3.68 mmol) in $CH_2Cl_2$ (12.300 ml) at −78° C. was added DMSO (0.523 ml, 7.37 mmol). The reaction mixture was stirred for 10 min and then {benzyl[(1R,2R)-2-hydroxycyclohexyl]amino}acetonitrile (2-1) (300 mg, 1.228 mmol) in 2 ml of CH2Cl2 was added. The reaction mixture was stirred at −78° C. for 1 hr before triethylamine (2.054 ml, 14.73 mmol) was added. The reaction mixture was stirred at −78° C. for 30 min and then warm gradually to 0° C. After another 30 min the reaction was quenched by H2O. The reaction mixture was diluted with aqueous potassium carbonate (saturated, 20 mL) and extracted with dichloromethane (3×30 mL). The combined organic fractions were washed with brine (saturated, 30 mL), dried, filtered. The organic phase was concentrated and the residue was diluted with dry THF, filtered with 0.25 uM filter and concentrated to give the title compound. LRMS m/z (M+H) Calcd:243.1. found: 243.3.

{Benzyl[(1R,2R)-2-(1-ethoxyethenyl)-2-hydroxycyclohexyl]amino}acetonitrile (2-3)

To {benzyl[(1R)-2-oxocyclohexyl]amino}acetonitrile (298 mg, 1.230 mmol) in THF (9 ml) at −78° C. was added ethylvinyl ether lithium (7.38 ml, 3.69 mmol) in THF via a cannula dropwise over 25 min. The reaction mixture was stirred for an addition 40 min at −78° C. before wet THF (THF/Water 10/1, 10 ml) was added. The reaction was allowed to warm to room temperature. The mixture was cooled, aqueous potassium carbonate (saturated, 10 mL) was added and the mixture was extracted with ethyl acetate (3×20 mL). The combined organic fractions were washed with brine (saturated, 30 mL), dried, filtered and the solvent was evaporated under reduced pressure to give the title compound. The crude product was used directly without further purification in the next step.

(4aR,8aR)-1-benzyl-4,4-diethoxyoctahydroquinolin-4a(2H)-ol (2-4)

To silver nitrate (125 mg, 0.735 mmol) in Ethanol (27.00 ml) at room temperature was added {Benzyl[(1R,2R)-2-(1-ethoxyethenyl)-2-hydroxycyclohexyl]amino}acetonitrile (220 mg, 0.700 mmol) in 10 ml of absolute ethanol. The reaction mixture was stirred for an addition 1 hr. Another 125 mg of Silver Nitrate was added and the reaction was stirred overnight. The reaction mixture was filtered through a pad of celite, concentrated. The residue was purified by column chromatography (dry load) on silica gel, eluting with $CH_2Cl_2$/MeOH/$NH_3$(Aq.) to give the title compound. $^1$H-NMR (500 MHz, $CDCl_3$) 2-4: δ 7.20-7.36 (m, 5H), 4.07 (d, 1H), 3.74 (dt, 1H), 3.62 (dt, 1H), 3.52 (dt, 1H), 3.41 (dt, 1H), 3.28 (bs, 1H), 3.06 (d, 1H), 2.61 (m, 1H), 2.00-2.14 (m, 2H), 1.88-1.98 (m, 2H), 1.70-1.80 (m, 2H), 1.54-1.62 (m, 2H), 1.22-1.44 (m, 2H), 1.18 (t, 6H). LRMS m/z (M+H) Calcd:334.5. found: 334.5.

(4R,4aS,8aR)-1-benzyl-4-(phenylamino)octahydroquinolin-4a(2H)-ol (2-5)

To (4aR,8aR)-1-benzyl-4,4-diethoxyoctahydroquinolin-4a(2H)-ol (200 mg, 0.600 mmol) in toluene (12.000 ml) at room temperature was added water (0.162 ml, 9.00 mmol) followed by camphorsulfonic acid (153 mg, 0.660 mmol). The reaction mixture was heated to reflux for 3 hrs. The reaction mixture was diluted with aqueous potassium carbonate (saturated, 30 mL). The aqueous layer was extracted with ethyl acetate (3×20 mL). The combined organic fractions were washed with brine (saturated, 30 mL), dried, filtered and the solvent was evaporated under reduced pressure. A mixture of (4aR,8aS)-1-benzyl-4a-hydroxyoctahydroquinolin-4(1H)-one (0.500 g, 1.93 mmol) and aniline (0.528 mL, 5.78 mmol) in 4% $CH_3COOH$ in DCE (10 mL) was stirred for 4 hr at 80° C. The reaction was then cooled to rt and $NaBH_4$ (0.438 g, 11.6 mmol) was then added followed by the addition of EtOH (10 mL). The mixture was then stirred overnight at rt. The mixture was then quenched with sat'd. aq. $NH_4Cl$. It was then basified with 2M $Na_2CO_3$ and extracted 3× with EtOAc. The combined organics were dried, filtered and concentrated. The residue was purified by column chromatography to give the title compound. $^1$H-NMR (500 MHz, $CDCl_3$) δ 7.29-7.35 (m, 4H), 7.23-7.30 (m, 1H), 7.17 (t, 2H, J=8.3 Hz), 6.76-6.84 (m, 3H), 4.10 (d, 1H, J=8.0 Hz), 3.96 (d, 1H, J=13.2 Hz), 3.03 (d, 1H, J=13.2 Hz), 2.97 (s, 1H), 2.86 (t, 1H, J=7.8 Hz), 2.37 (d, 1H, J=6.8 Hz), 1.41-2.24 (m, 10H). HRMS (ES) m/z M±H calc'd: 337.2274. found: 337.2275.

(4aR,8aS)-4-(phenylamino)octahydroquinolin-4a(2H)-ol (2-6)

To a mixture of (4aS,8aS)-1-benzyl-4-(phenylamino)octahydroquinolin-4a(2H)-ol (0.280 g, 0.832 mmol) in MeOH (5 mL) was added $NH_4COOH$ (0.840 g, 13.3 mmol) and 10% Pd/C (0.280 g). The resulting mixture was heated at 60° C. for several hours. The reaction was cooled to rt, filtered through a syringe filter, washed with EtOH, and concentrated to give the title compound. LRMS M+H calc'd: 247.34. found 247.34

1-[(4aS,8aS)-4a-hydroxy-4-(phenylamino)octahydroquinolin-1(2H)-yl]-3-methylbutan-1-one (2-7)

To a mixture of (4aR,8aS)-4-(phenylamino)octahydroquinolin-4a(2H)-ol (20 mg, 0.081 mmol) in 1:1 $CH_2Cl_2$:sat'd. aq. $NaHCO_3$ (3 mL) was added 3-methylbutanoyl chloride (0.049 g, 0.406 mmol). The mixture was stirred at rt for 1 hr. The mixture was diluted with sat'd. aq. $NaHCO_3$ and $CH_2Cl_2$ and extracted 3× with $CH_2Cl_2$. The combined organics were dried (anted. $Na_2SO_4$), filtered, and concentrated. The residue was purified by column chromatography to give the title compound. $^1$H NMR (400 MHz, $CDCl_3$) δ 7.22-7.40 (m, 5H), 4.38 (d, 1H, J=10.4 Hz), 3.96 (d, 1H, J=10.2 Hz), 3.35 (t, 1H, J=9.4 Hz), 2.62-2.85 (m, 2H), 1.15-2.40 (m, 12H), 0.81-0.99 (m, 6H). HRMS (ES) m/z M+H calc'd: 331.2380. found: 331.2379.

TABLE 2

| # | Structure | MS M + 1 |
|---|---|---|
| 2-8 | 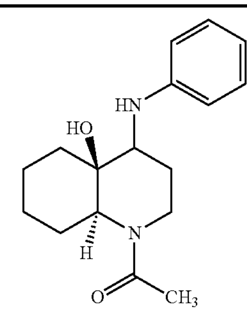 | 289.1911 |
| 2-9 | 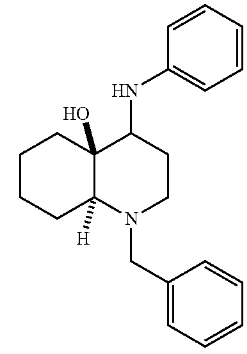 [SMILES: O[C@]12CCCC[C@@H]1N(Cc1ccccc1)CCC2Nc1ccccc1] | 337.2275 |

TABLE 2-continued
| # | Structure | MS M + 1 |
|---|---|---|
| 2-10 | 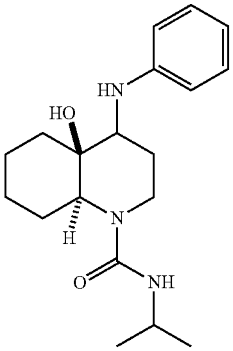 [SMILES: CC(C)NC(=O)N1CCC(Nc2ccccc2)[C@@]2(O)CCCC[C@H]12] | 332.2333 |
| 2-11 | 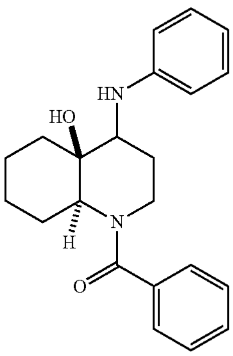 [SMILES: O=C(c1ccccc1)N1CCC(Nc2ccccc2)[C@@]2(O)CCCC[C@H]12] | 351.2065 |
| 2-12 | 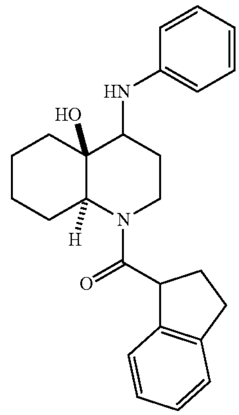 [SMILES: O=C(C1CCc2ccccc21)N1CCC(Nc2ccccc2)[C@@]2(O)CCCC[C@H]12] | 391.2378 |
Example 3
(4R,4aS,8aS)-4-[(4-fluorophenyl)amino]hexahydro-2H-chromen-4a(5H)-ol
Example Scheme 3
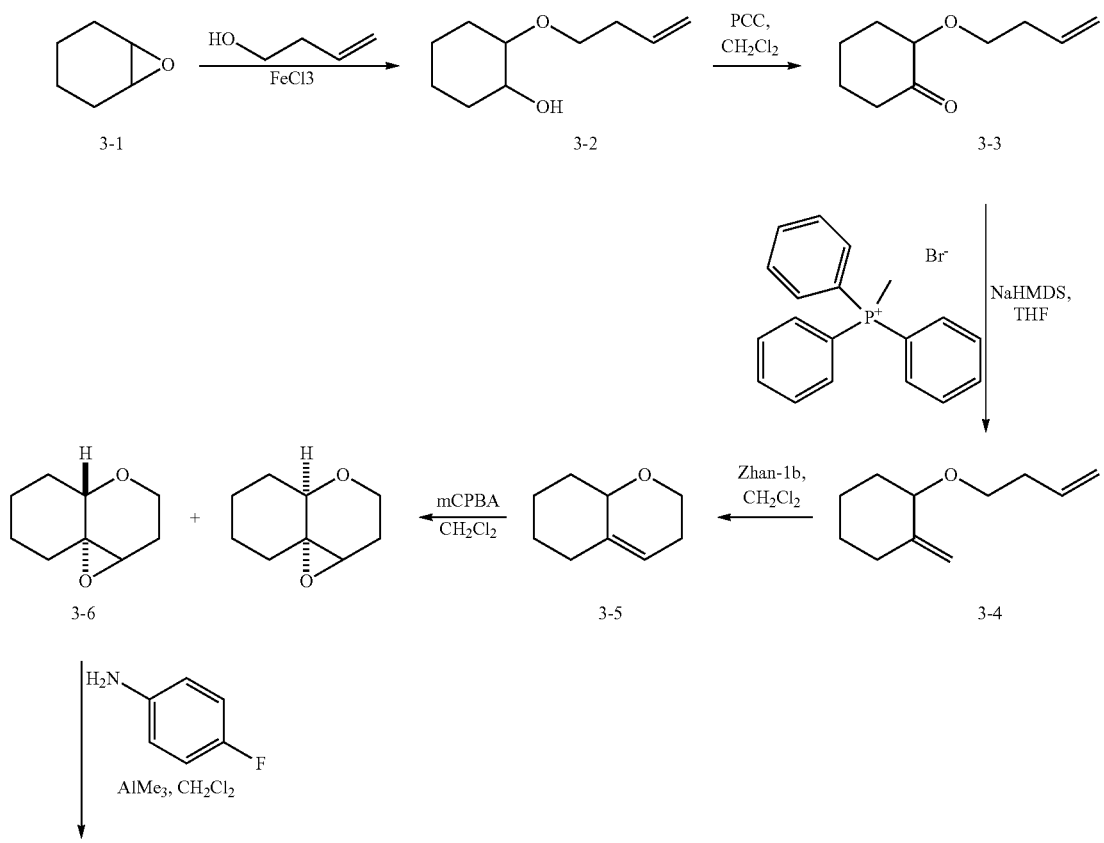

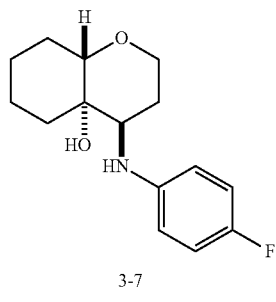

3-7

2-(but-3-en-1-yloxy)cyclohexanol (3-2)

To a mixture of cyclohexene oxide (3-1) (10.0 g, 102 mmol) in 3-buten-1-ol (17.4 mL, 204 mmol) cooled to 0° C. was added $FeCl_3$ (1.65 g, 10.2 mol) The mixture was removed from the ice bath and stirred at rt for 1 hr. The reaction was quenched with water and extracted ether. The combined organics were washed with brine, dried, filtered, and concentrated. The residue was purified by column chromatography to give the title compound. $^1$H NMR (400 MHz, $CDCl_3$) δ 5.77-5.88 (m, 1H), 5.00-5.15 (m, 2H), 3.69-3.76 (m, 1H), 3.39-3.44 (m, 2H), 2.98-3.05 (m, 1H), 2.74 (s, 1H), 2.30-2.39 (m, 2H), 1.94-2.11 (m, 3H), 1.61-1.79 (m, 3H), 1.06-1.37 (m, 2H).

2-(but-3-en-1-yloxy)cyclohexanone (3-3)

To a suspension of PCC (26.6 g, 123 mmol) in $CH_2Cl_2$ (160 mL) was added 2-(but-3-en-1-yloxy)cyclohexanol (7 g, 41 mmol) in $CH_2Cl_2$ (10 mL). The reaction was stirred at rt overnight. The mixture was filtered through a pad of celite and washed with $CH_2Cl_2$. The residue was purified by column chromatography to give the title compound. $^1$H NMR (500 MHz, $CDCl_3$) δ 5.75-5.90 (m, 1H), 4.95-5.15 (m, 2H), 3.78 (dd, 1H, J=5.37 Hz, 9.76 Hz), 3.65-3.70 (m, 1H), 3.39-3.45 (m, 1H), 1.05-2.58 (m, 10H).

1-(But-3-en-1-yloxy)-2-methylidenecyclohexane (3-4)

To a mixture of methyltriphenylphosphonium bromide (22.30 g, 62.4 mmol) in THF (125 mL) at rt was added sodium hexamethyldisilylazide (2M in THF, 31.2 mL, 62.4 mmol) dropwise. The mixture was heated to 60° C. for 1 hr. 2-(but-3-en-1-yloxy)cyclohexanone (7.0 g, 41.6 mmol.) was then added and the mixture was stirred at 60° C. for 3 hr. The reaction was cooled to rt, quenched with sat'd. aq.$NH_4Cl$, and extracted with $Et_2O$. The combined organics were dried filtered, and concentrated. The residue was purified by column chromatography to give the title compound. $^1$H NMR (500 MHz, $CDCl_3$) δ 5.78-5.90 (m, 1H), 5.00-5.13 (m, 2H), 4.82 (s, 1H), 4.78 (s, 1H), 3.74 (dd, 1H, J=3.9 Hz, 6.3 Hz), 3.35-3.49 (m, 2H), 1.12-2.38 (m, 10H).

3,5,6,7,8,8a-hexahydro-2H-chromene (3-5)

A mixture of 1-(but-3-en-1-yloxy)-2-methylidenecyclohexane (5.21 g, 31.3 mmol) in DCE (313 mL) was degassed 3×N2/pump. Zhan-1b (1.15 g, 1.57 mmol) was then added and the reaction was degassed again. The reaction was stirred at rt for 2 hr. The reaction mixture was concentrated and the residue was purified by column chromatography to give the title compound. $^1$H NMR (500 MHz, $CDCl_3$) δ 5.48 (d, 1H, J=2.7 Hz), 3.90-3.96 (m, 2H), 3.50-3.60 (m, 1H), 2.18-2.34 (m, 2H), 2.02-2.08 (m, 1H), 1.84-1.99 (m, 2H), 1.76-1.83 (m, 1H), 1.66-1.74 (m, 1H), 1.15-1.43 (m, 3H).

(1aS,8aS)-hexahydro-1aH,4aH-oxireno[d]chromene (3-6)

To a mixture of 3,5,6,7,8,8a-hexahydro-2H-chromene (3.27 g, 23.66 mmol) in $CH_2Cl_2$ (75 mL) at 0° C. was added MCPBA (~77%, 6.53 g, 28.4 mmol). The mixture was warmed to rt and stirred for 1 hr. The mixture was quenched with sat'd. aq. $Na_2SO_3$. The mixture was then partitioned between $CH_2Cl_2$ and sat'd. aq. $NaHCO_3$. Extracted with $CH_2Cl_2$. The combined organics were dried, filtered, and concentrated. The residue was purified by column chromatography to give the title compound. $^1$H NMR (500 MHz, $CDCl_3$) δ 3.85 (dd, 1H, J=7.8 Hz, 11.7 Hz), 3.54 (dd, 1H, J=4.6 Hz, 11.7 Hz), 3.31-3.38 (m, 1H), 3.19 (d, 1H, J=5.13 Hz), 2.15-2.24 (m, 1H), 1.75-1.97 (m, 4H), 1.52-1.72 (iii, 3H), 1.37-1.49 (m, 1H), 1.30-1.38 (m, 1H).

(4R,4aS,8aS)-4-[(4-fluorophenyl)amino]hexahydro-2H-chromen-4a(5H)-ol (3-7)

To a mixture of 4-Fluoroaniline (0.173 g, 1.56 mmol) in $CH_2Cl_2$ (3 mL) at 0° C. was added trimethylaluminum (2M in toluene, 0.778 mL) dropwise. The mixture was warmed to rt and stirred for 30 min. Trans hexahydro-1aH,4aH-oxireno[d] chromene (0.200 g, 1.30 mmol) in $CH_2Cl_2$ (2 mL) was then added and the mixture was stirred at rt overnight. The reaction was cooled to 0° C. and treated with 50% NaOH (1 mL) then water (1 mL). The reaction mixture was extracted 3× with $CH_2Cl_2$. The combined organics were dried, filtered, and concentrated. The residue was purified by column chromatography to give the title compound. $^1$H NMR (500 MHz, $CDCl_3$) δ 6.90 (t, 2H, J=8.8 Hz), 6.60 (dd, 2H, J=4.2 Hz, 8.8 Hz), 3.88 (dd, 1H, J=5.4 Hz, 12.0 Hz), 3.68-3.74 (m, 1H), 3.47 (dd, 1H, J=4.8 Hz, 11.5 Hz), 3.40 (t, 1H, J=3.2 Hz), 2.30-2.40 (m, 1H), 1.69-1.78 (m, 2H), 1.54-1.68 (m, 5H), 1.45-1.48 (m, 1H), 1.20-1.30 (m, 1H), HRMS (ES) m/z M+H calc'd.: 266.1551. found: 266.1556

TABLE 3
| # | Structure | MS M + 1 |
|---|---|---|
| 3-8 | 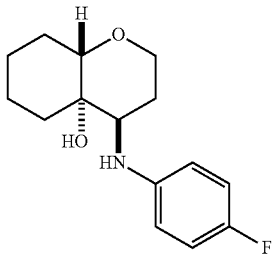 [SMILES: O[C@]12CCCC[C@@H]1OCC[C@H]2Nc1ccc(F)cc1] | 266.1556 |
| 3-9 | 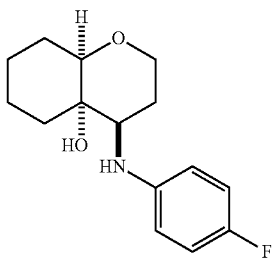 [SMILES: O[C@]12CCCC[C@H]1OCC[C@H]2Nc1ccc(F)cc1] | 266.1553 |
| 3-10 | 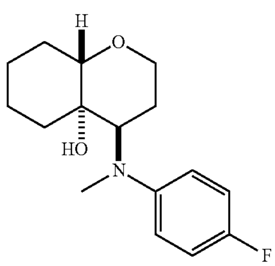 [SMILES: CN(c1ccc(F)cc1)[C@@H]1CCO[C@H]2CCCC[C@@]21O] | 280.1711 |
TABLE 3-continued
| # | Structure | MS M + 1 |
|---|---|---|
| 3-11 | 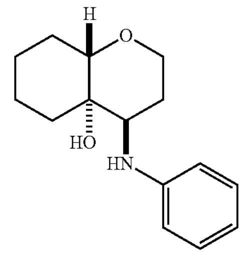 [SMILES: O[C@]12CCCC[C@@H]1OCC[C@H]2Nc1ccccc1] | 248.1653 |
| 3-12 | 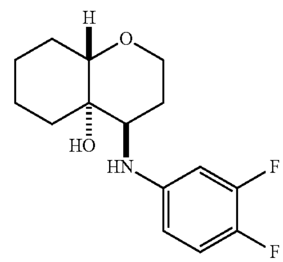 [SMILES: O[C@]12CCCC[C@@H]1OCC[C@H]2Nc1ccc(F)c(F)c1] | 284.1467 |
Example 4
(4R,4aR,8aR)-4-[(4-fluorophenyl)amino]octahydro-4-aH-isochromen-4a-ol
Example Scheme 4
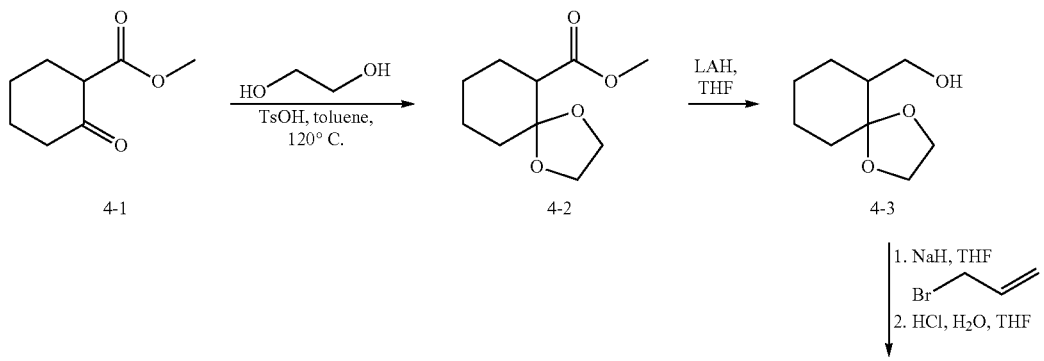

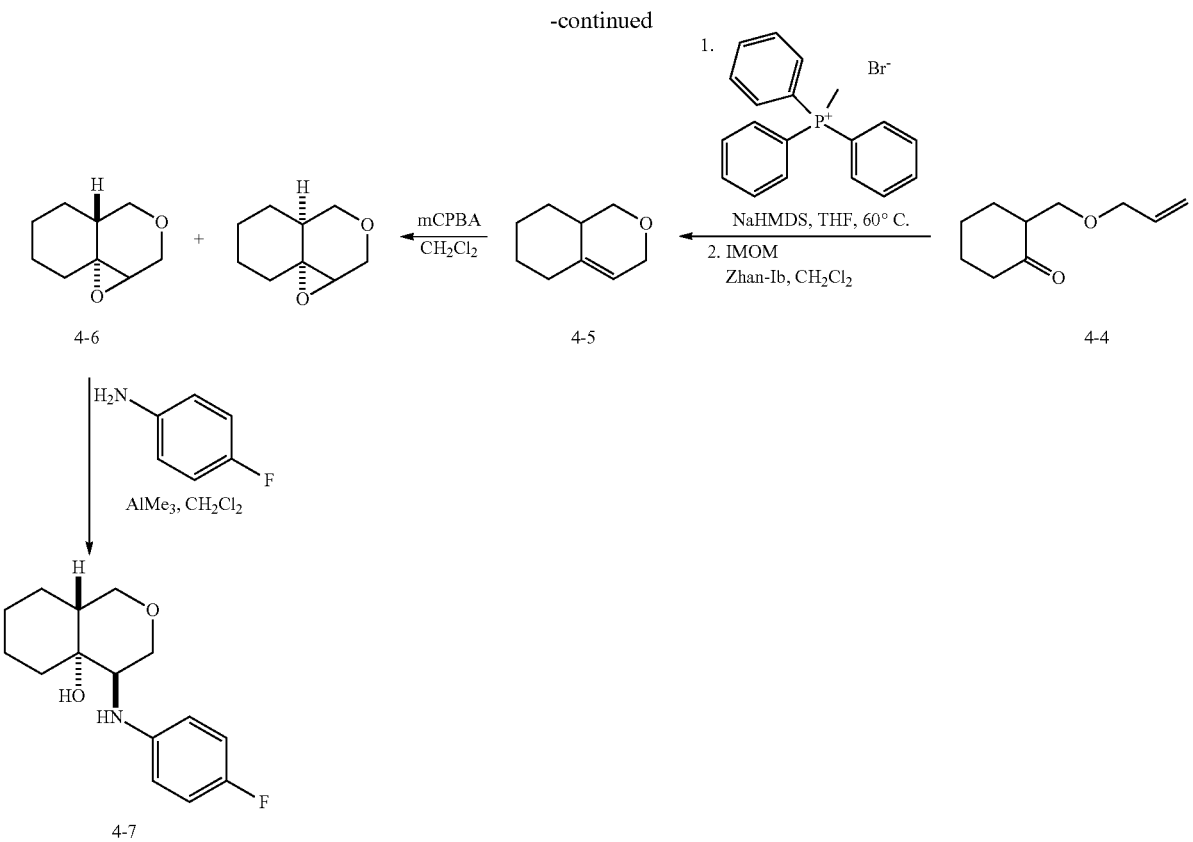

Methyl 1,4-dioxaspiro[4.5]decane-6-carboxylate (4-2)

A mixture of methyl-2-oxocyclohexanecarboxylate (4-1) (7.0 g, 44.8 mmol), ethylene glycol (3.00 mL, 53.8 mmol) and p-toluenesulfonic acid monohydrate (0.853 g, 4.48 mmol) in Benzene (45 mL) was heated to reflux overnight. The reaction was then cooled to rt and concentrated. The residue was purified by column chromatography to give the title compound. $^1$H NMR (500 MHz, CDCl$_3$) δ 3.86-3.99 (m, 4H), 3.69 (s, 3H), 2.69 (dd, 1H, J=4.9 Hz, 9.0 Hz), 1.82-1.97 (m, 3H), 1.58-1.73 (m, 3H), 1.45-1.53 (m, 1H), 1.26-1.37 (m, 1H).

1,4-dioxaspiro[4.5]dec-6-ylmethanol (4-3)

To a mixture of methyl 1,4-dioxaspiro[4.5]decane-6-carboxylate (3.00 g, 15.0 mmol) in THF (45 mL) at 0° C. was added LiAlH$_4$ (2M in THF (9.00 mL, 18.0 mmol) dropwise. The mixture was then allowed to warm to rt and stirred overnight. The mixture was then cooled to 0° C. and 1.36 mL of H$_2$O was added very slowly. The reaction mixture was basified by adding 0.682 mL of 15% NaOH and then 3.41 mL of H$_2$O. The resulting mixture was filtered through a pad of celite, washed with Et$_2$O, and concentrated. The residue was purified by column chromatography to give the title compound. $^1$H NMR (500 MHz, CDCl$_3$) δ 3.95-4.05 (m, 4H), 3.71-3.79 (m, 1H), 3.52-3.59 (m, 1H), 2.81 (dd, 1H, J=3.9 Hz, 7.1 Hz), 1.78-1.91 (m, 2H), 1.61-1.73 (m, 3H), 1.41-1.53 (m, 2H), 1.24-1.40 (m, 2H).

2-[(prop-2-en-1-yloxy)methyl]cyclohexanone (4-4)

To a mixture of NaH (1.14 g, 60% oil dispersion, 28.6 mmol) in dry THF (45 mL) at 0° C. was added 1,4-dioxaspiro[4.5]dec-6-ylmethanol (2.46 g, 14.3 mmol) in dry THF (5 mL). The mixture was allowed to warm to rt and stirred for 1 hr. The mixture was then cooled to 0° C. and allyl bromide (2.10 mL, 24.28 mmol) was added in one portion. The mixture was then allowed to warm to rt and stirred for 1 hr. The mixture was then heated to 60° C. overnight. It was cooled to 0° C. and quenched with 50 mL of 10% aq HCl. This mixture was stirred for 1 hr at rt. The resulting mixture was cooled to 0° C. and neutralized carefully with solid Na$_2$CO$_3$ and then extracted with Et$_2$O. The combined organics were dried, filtered, and concentrated. The residue was purified by column chromatography to give the title compound. $^1$H NMR (500 MHz, CDCl$_3$) δ 5.86-5.95 (m, 1H), 5.28 (d, 1H, J=1.7 Hz), 5.25 (d, 1H, J=1.5 Hz), 5.17 (d, 1H, J=10.5 Hz), 3.94-4.03 (m, 2H), 3.79 (dd, 1H, J=5.1 Hz, 9.8 Hz), 3.38 (dd, 1H, J=7.33 Hz, 9.53 Hz), 2.56-2.65 (m, 1H), 2.26-2.43 (m, 3H), 2.02-2.10 (m, 1H), 1.85-1.93 (m, 1H), 1.61-1.74 (m, 2H), 1.39-1.49 (m, 1H).

3,5,6,7,8,8a-hexahydro-1H-isochromene (4-5)

To a mixture of methyltriphenylphosphonium bromide (3.75 g, 10.51 mmol) in THF (31 mL) at rt was added sodium hexamethyldisilylazide (2M in THF, 5.25 mL, 10.51 mmol) dropwise. The mixture was heated to 60° C. for 1 hr. 2-[(prop-2-en-1-yloxy)methyl]cyclohexanone (0.884 g, 5.25 mmol) in THF (4 mL+2 mL rinse) was then added and the mixture was stirred at 60° C. for 3 hr. The reaction was then cooled to rt, quenched with sat'd. aq. NH$_4$Cl, and extracted with Et$_2$O. The combined organics were dried, filtered, concentrated, and purified via column chromatography.

A mixture of (2-methylidenecyclohexyl)methyl prop-2-en-1-yl ether (0.104 g, 0.626 mmol) in DCE (6.5 mL) was degassed 3×N₂/pump, then Zhan-1b (0.023 g, 0.031 mmol) was added and the reaction was degassed again The mixture was stirred at rt for 2 hr. It was concentrated and purified by silica gel chromatography to provide the title compound. ¹H NMR (500 MHz, CDCl₃) δ 5.39 (t, 1H, J=2.4 Hz), 4.04-4.10 (m, 2H), 3.92 (dd, 1H, J=5.7 Hz, 11.2 Hz), 3.24 (dd, 1H, J=8.2 Hz, 11.2 Hz), 2.15-2.27 (m, 2H), 1.92-2.02 (m, 1H), 1.74-1.83 (m, 2H), 1.64-1.72 (m, 1H), 1.18-1.45 (m, 2H), 0.93-1.06 (m, 1H).

Octahydrooxireno[d]isochromene (4-6)

To a mixture of 3,5,6,7,8,8a-hexahydro-1H-isochromene (0.410 g, 2.97 mmol) in CH₂Cl₂ (10 mL) at 0° C. was added MCPBA (~77%, 1.24 g, 445 mmol). The mixture was stirred at rt for 3 hr. It was quenched with sated aq. sodium sulfite. The mixture was diluted with CH₂Cl₂ and sat'd. aq. NaHCO₃ then extracted 3× with CH₂Cl₂. The combined organics were dried (anhd. Na₂SO₄), filtered, and concentrated. The residue was purified by column chromatography to give the title compound.

(4R,4aR,8aR)-4-[(4-fluorophenyl)amino]octahydro-4-aH-isochromen-4a-ol (4-7)

To a mixture of 4-fluoroaniline (0.721 g, 6.48 mmol) in CH₂Cl₂ (6 mL) at 0° C. was added trimethylaluminum (2M in toluene, 3.24 mL) dropwise. The mixture was warmed to rt for 30 min. A mixture of both cis and trans octahydrooxireno[d]isochromene (0.200 g, 1.30 mmol) in CH2Cl2 2 mL+0.5 mL rinse) was then added and the mixture was stirred at rt overnight. The reaction was cooled to 0° C. and treated with 50% NaOH (1 mL) then water (1 mL). The mixture was diluted with more water and extracted 3× with CH₂Cl₂. The combined organics were dried (anhd. Na₂SO₄), filtered, and concentrated. The residue was purified by column chromatography to give the title compound. ¹H NMR (500 MHz, CDCl₃) δ 6.94 (1, 2H, J=8.6 Hz), 6.78 (dd, 2H, J=4.2 Hz, 8.8 Hz), 4.14 (dd, 1H, J=1.5 Hz, 12.0 Hz), 3.64 (d, 1H, J=11.5 Hz), 3.56 (dd, 1H, J=4.6 Hz, 11.0), 3.48 (t, 1H, J=11.5 Hz), 3.10 (s, 1H), 1.17-2.00 (m, 9H). HRMS (ES) m/z M+H calc'd.: 266.1551. found: 266.1554

TABLE 4

| # | Structure | MS M + 1 |
|---|---|---|
| 4-8 | 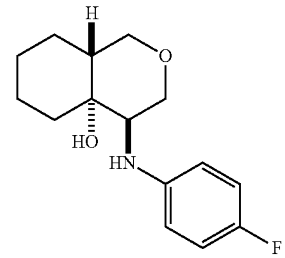 [SMILES: O[C@]12CCCC[C@@H]1COC[C@H]2Nc1ccc(F)cc1] | 266.1554 |
| 4-9 | 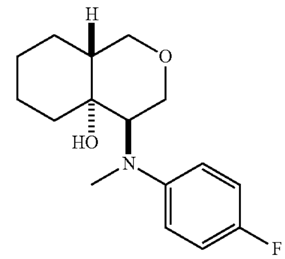 [SMILES: CN(c1ccc(F)cc1)[C@@H]1COC[C@H]2CCCC[C@@]21O] | 280.1706 |
| 4-10 | 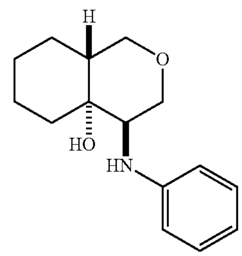 [SMILES: O[C@]12CCCC[C@@H]1COC[C@H]2Nc1ccccc1] | 248.1647 |
| 4-11 | 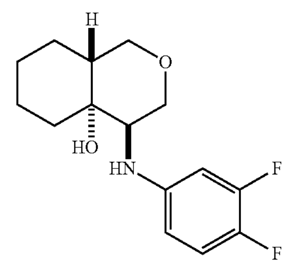 [SMILES: O[C@]12CCCC[C@@H]1COC[C@H]2Nc1ccc(F)c(F)c1] | 284.1460 |

Example 5
(4aS,8R,8aR)-8-[(4-fluorophenyl)amino]hexahydro-1H-isochromen-8a(3H)-ol Example Scheme 5

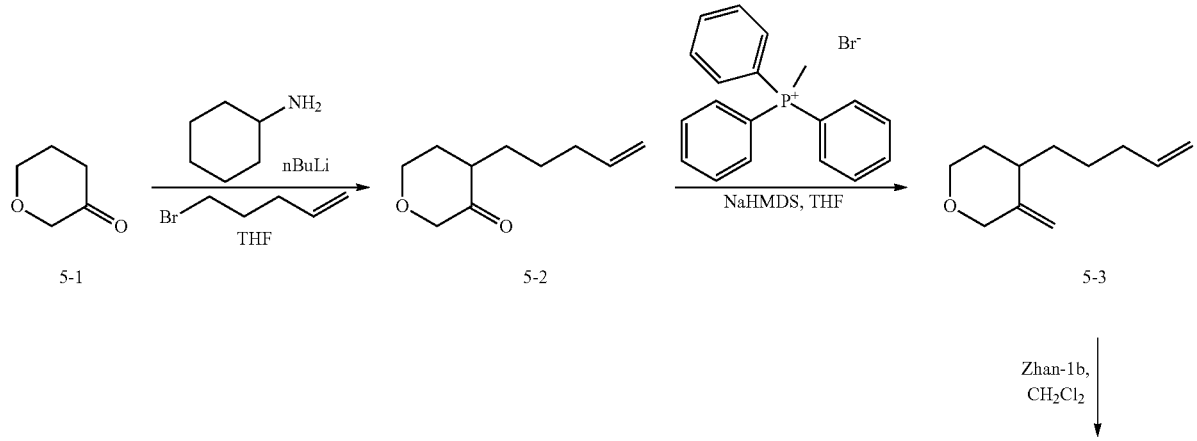

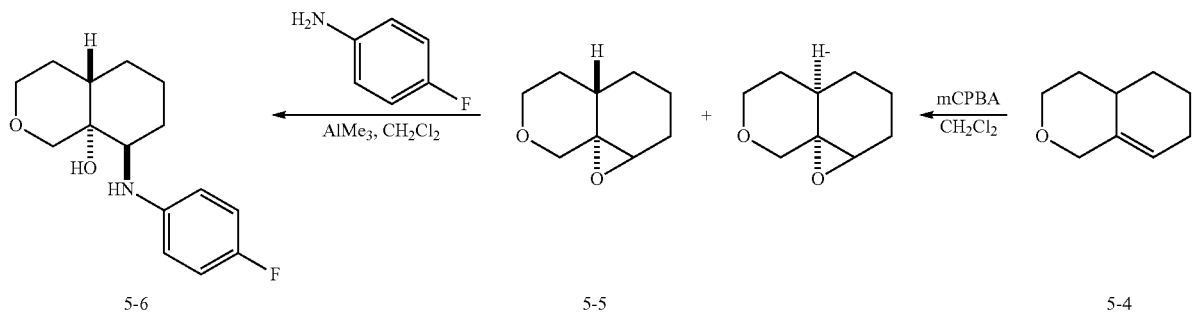

4-(pent-4-en-1-yl)dihydro-2H-pyran-3(4H)-one (5-2)

Cyclohexylamine (3.43 ml, 30.0 mmol) was added to pyran-3-one (3000 mg, 30.0 mmol) in benzene (20 mL). The reaction mixture was stirred at RT for 30 min and then refluxed for 2 hr with a dean-stark trap. The benzene was then distilled off and the residue was redissolved in THF (2 mL) and added to BuLi (13.18 ml, 33.0 mmol) in THF (Volume: 30.000 ml) at 0° C. The reaction mixture was stirred at 0° C. for 1 h before 5-bromo-1-pentene (5582 mg, 37.5 mmol) was added. The reaction mixture was stirred at 0° C. for 2 hr. The mixture was cooled and quenched with water. The reaction mixture was extracted with diethyl ether (3×20 mL). The combined organic fractions were washed with water and brine (saturated, 100 mL), dried, filtered and the solvent was evaporated under reduced pressure (400 mmhg). The residue was purified by column chromatography on silica gel to provide the title compound. $^1$H NMR (500 MHz, CDCl$_3$) δ 5.74-5.86 (m, 1H), 4.92-5.06 (m, 2H), 3.90-4.06 (m, 3H), 3.77-3.85 (m, 1H), 2.41-2.49 (m, 1H), 2.16-2.24 (m, 1H), 2.01-2.12 (m, 2H), 1.72-1.97 (m, 2H), 1.31-1.49 (m, 3H).

3-methylidene-4-(pent-4-en-1-yl)tetrahydro-2H-pyran (5-3)

NaHMDS (5.35 ml, 10.70 mmol) was added to methyltriphenylphosphonium bromide (3822 mg, 10.70 mmol) in THF (53.500 ml) at RT. The reaction was stirred at RT for 1 hr before 4-(pent-4-en-1-yl)dihydro-2H-pyran-3(4H)-one (900 mg, 5.35 mmol) in THF (2 mL) was added at 0° C. The reaction mixture was stirred at room temperature for 2 hr. The mixture was cooled and quenched with aqueous NH$_4$Cl. The reaction mixture was extracted with diethyl ether (3×20 mL). The combined organic fractions were washed with water and brine (saturated, 100 mL), dried, filtered and the solvent was evaporated under reduced pressure (400 mmhg). The residue was purified by column chromatography on silica gel to provide the title compound. $^1$H NMR (500 MHz, CDCl$_3$) δ 5.75-5.89 (m, 1H), 4.92-5.06 (m, 2H), 4.86 (s, 1H), 4.77 (t, 1H, J=1.5 Hz), 4.12 (d, 1H, J=12.1 Hz), 3.86-3.96 (m, 2H), 3.57-3.65 (m, 1H), 2.15-2.24 (m, 1H), 2.00-2.12 (m, 2H), 1.81-1.91 (m, 1H), 1.64-1.76 (m, 1H), 1.21-1.52 (m, 4H).

3,4,4a,5,6,7-hexahydro-1H-isochromene (5-4)

3-methylidene-4-(pent-4-en-1-yl)tetrahydro-2H-pyran (1320 mg, 7.94 mmol) was added to CH$_2$Cl$_2$ (159.00 ml) at RT. The reaction was degassed three times. Zhan-1b (58.3 mg, 0.079 mmol) was added at 0° C. The reaction mixture was degassed again and then stirred at room temperature for 1 h. The mixture was concentrated under reduced pressure (280 mmhg). The residue was purified by column chromatography on silica gel to provide the title compound. $^1$H NMR (500 MHz, CDCl$_3$) δ 5.54 (d, 1H, J=2.2 Hz), 4.06 (d, 1H, J=122 Hz), 3.97 (dd, 1H, J=4.4 Hz, 11.2 Hz), 3.84-3.91 (m, 1H), 3.46-3.53 (m, 1H), 2.21 (bs, 1H), 1.92-2.19 (m, 2H), 1.80-1.89 (m, 1H), 1.68-1.86 (m, 2H), 1.36-1.48 (m, 2H), 1.16-1.26 (m, 1H).

(1aS,5aS)-hexahydro-4H-oxireno[i]isochromene (5-5)

To a mixture of 3,4,4a,5,6,7-hexahydro-1H-isochromene (0.410 g, 2.97 mmol) in CH$_2$Cl$_2$ (10 mL) at 0° C. was added MCPBA (~77%, 1.24 g, 445 mmol). The mixture was stirred at rt for 3 hr. It was quenched with sat'd aq. sodium sulfite. The mixture was diluted with CH$_2$Cl$_2$ and sat'd. aq. NaHCO$_3$ then extracted 3× with CH$_2$Cl$_2$. The combined organics were dried (anhd. Na$_2$SO$_4$), filtered, and concentrated. The residue was purified by column chromatography to give the title compound. $^1$H NMR (500 MHz, CDCl$_3$) δ 4.03-4.10 (m, 1H), 3.86 (d, 1H, J=12.0 Hz), 3.54-3.62 (m, 1H), 3.34 (d, 1H, J=12.0 Hz), 3.03 (d, 1H, J=4.4 Hz), 1.70-1.98 (m, 3H), 1.52-1.65 (m, 3H), 1.17-1.34 (m, 3H).

(4aS,8R,8aR)-8-[(4-fluorophenyl)amino]hexahydro-1H-isochromen-8a(3H)-ol (5-6)

To a mixture of 4-fluoroaniline (0.721 g, 6.48 mmol) in CH$_2$Cl$_2$ (6 mL) at 0° C. was added trimethylaluminum (2M in toluene, 3.24 mL) dropwise. The mixture was warmed and stirred to rt for 30 min. (1aS,5aS)-hexahydro-4H-oxireno[i]isochromene (0.200 g, 1.30 mmol) in CH$_2$Cl$_2$ 2 mL+0.5 mL rinse) was then added and the mixture was stirred at rt overnight. The reaction was cooled to 0° C. and treated with 50% NaOH (1 mL) then water (1 mL) The mixture was diluted with more water and extracted 3× with CH$_2$Cl$_2$. The combined organics were dried (anhd. Na$_2$SO$_4$), filtered, and concentrated. The residue was purified by column chromatography to give the title compound. $^1$H NMR (500 MHz, CDCl$_3$) δ 6.84-6.90 (m, 2H), 6.51-6.57 (m, 2H), 3.90-3.97 (m, 1H), 3.50-3.64 (m, 3H), 3.35-3.45 (m, 2H), 2.61 (s, 1H), 1.95-2.04 (m, 1H), 1.32-1.75 (m, 8H). HRMS (ES) m/z M+H cal'd: 266.1551. found: 266.1548.

TABLE 5
| # | Structure | MS M + 1 |
|---|---|---|
| 507 | 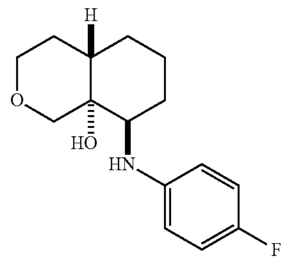 [SMILES: O[C@]12COCC[C@@H]1CCC[C@H]2Nc1ccc(F)cc1] | 266.1549 |
| 5-8 | 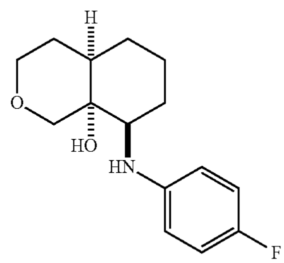 [SMILES: O[C@]12COCC[C@H]1CCC[C@H]2Nc1ccc(F)cc1] | 266.1548 |
TABLE 5-continued
| # | Structure | MS M + 1 |
|---|---|---|
| 5-9 | 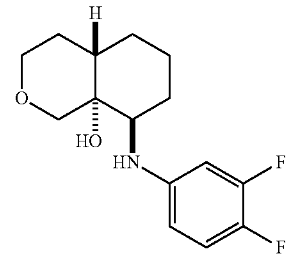 [SMILES: O[C@]12COCC[C@@H]1CCC[C@H]2Nc1ccc(F)c(F)c1] | 284.1458 |
| 5-10 | 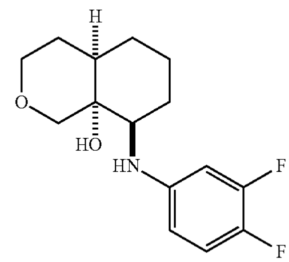 [SMILES: O[C@]12COCC[C@H]1CCC[C@H]2Nc1ccc(F)c(F)c1] | 284.1456 |
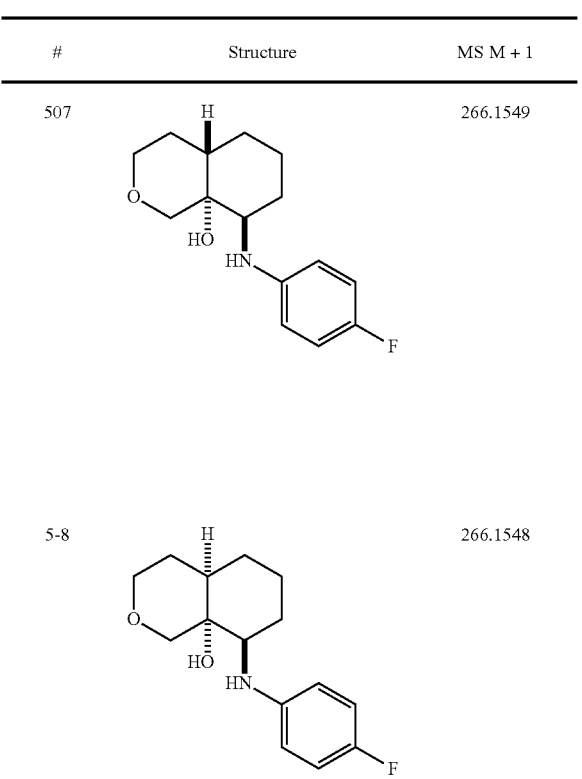
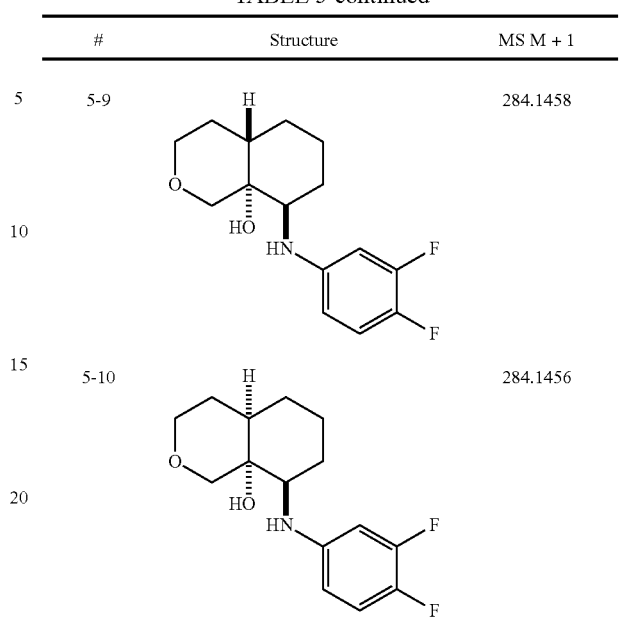
Example 6
(4aR,5R,8aS)-5-[(4-fluorophenyl)amino]octahydro-4-aH-isochromen-4a-ol
Example Scheme 6
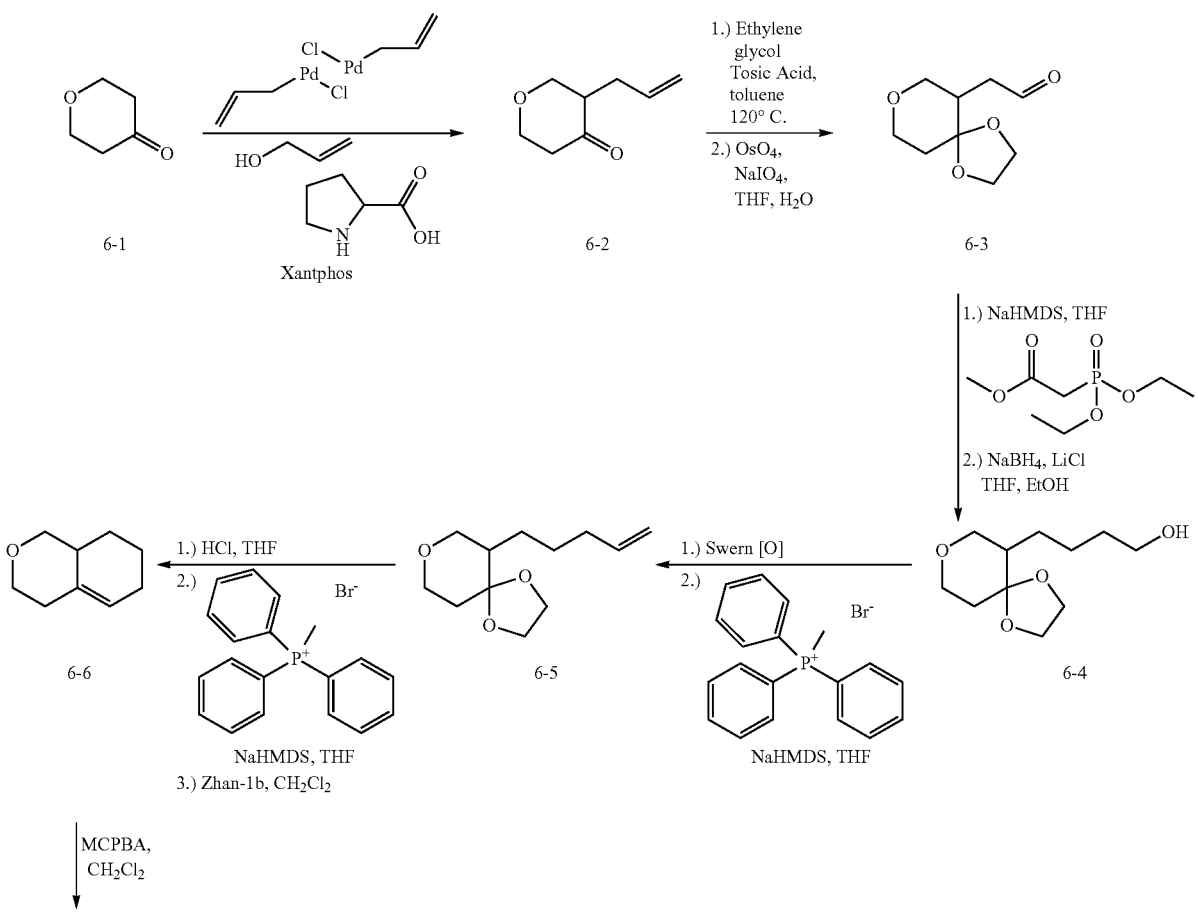

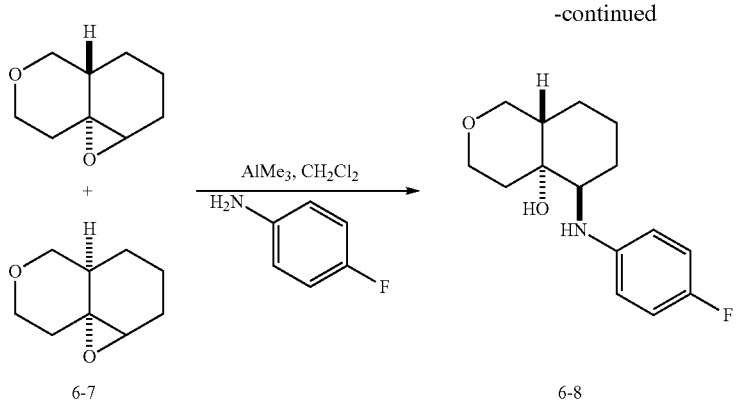

3-(prop-2-en-1-yl)tetrahydro-4H-pyran-4-one (6-2)

A mixture of tetrahydro-4H-pyran-4-one (6-1) (5.17 g, 51.7 mmol), prop-2-en-1-ol (1.00 g, 17.2 mmol), allylPalladium Chloride dimer (0.157 g, 0.430 mmol), Xantphos (0.498 g, 0.861 mmol), and DL-proline (0.595 g, 5.17 mmol) in DMSO (35 mL) was degassed (2×pump/N2) and heated to 70° C. overnight. The mixture was cooled to rt and partitioned between water and Et$_2$O. Extracted with Et$_2$O. The combined organics were washed with 1:1 brine:water, dried (anhd. Na$_2$SO$_4$), filtered, and concentrated. The residue was purified by column chromatography to give the title compound. $^1$H NMR (500 MHz, CDCl$_3$) δ 5.70-5.80 (m, 1H), 5.01-5.09 (m, 2H), 4.13-4.22 (m, 2H), 3.72-3.79 (m, 1H), 3.43 (t, 1H, J=11.2 Hz), 2.52-2.66 (m, 3H), 2.39-2.47 (m, 1H), 1.99-2.07 (m, 1H).

1,4,8-trioxaspiro[4.5]dec-6-ylacetaldehyde (6-3)

A mixture of 3-(prop-2-en-1-yl)tetrahydro-4H-pyran-4-one (1.00 g, 7.13 mmol), ethylene glycol (0.597 mL, 10.70 mmol) and p-toluenesulfonic acid monohydrate (0.136 g, 0.713 mmol) in toluene (30 mL) was heated to 120° C. overnight. The reaction was then cooled to rt and concentrated. The residue was purified via column chromatography and used in the next step. To a mixture of 6-(prop-2-en-1-yl)-1,4,8-trioxaspiro[4.5]decane (0.840 g, 4.56 mmol) and osmium tetraoxide (2.5 wt % in T-BuOH, 0.551 mL, 0.046 mmol) in THF (15 mL) and water (5 mL) at rt was added sodium periodate (2.15 g, 1.19 mmol) portionwise over 5 min. The mixture was stirred at rt for 2 hr. The reaction was then quenched with sat'd. aq. sodium sulfite. The mixture was extracted 3× with Et$_2$O. The combined organics were dried (anhd. Na$_2$SO$_4$), filtered, and concentrated. The residue was purified by column chromatography to give the title compound. $^1$H NMR (500 MHz, CDCl$_3$) δ 9.71 (s, 1H), 3.81-3.99 (m, 6H), 3.64-3.70 (m, 1H), 3.47 (dd, 1H, J=8.6 Hz, 11.5 Hz), 2.49-2.57 (m, 2H), 2.18-2.26 (m, 1H), 1.65-1.82 (m, 2H).

4-(1,4,8-trioxaspiro[4.5]dec-6-yl)butan-1-ol (6-4)

To a mixture of the methyl (diethoxyphosphoryl)acetate (0.938 g, 4.46 mmol) in dry THF (20 mL) under N$_2$ at 0° C. was added NaHMDS (2M in THF (1.98 mL, 3.96 mmol). The mixture was stirred for 30 minutes at 0° C. 1,4,8-trioxaspiro[4.5]dec-6-ylacetaldehyde (0.554 g, 2.98 mmol) in dry THF (5 mL) was then added and the mixture was allowed to warm to rt and stirred for 1.5 hr. It was quenched with sat'd. aq. NH$_4$Cl and extracted 3× with Et$_2$O. The combined organics were dried, filtered, and concentrated. The residue was purified via column chromatography and used in the next step.

To a mixture of methyl (2E)-4-(1,4,8-trioxaspiro[4.5]dec-6-yl)but-2-enoate (0.747 g, 3.08 mmol) in THF (9 mL) was added anhydrous LiCl (0.261 g, 6.71 mmol) and Sodium borohydride (0.233 g, 6.17 mmol). EtOH (12 mL) was then added slowly and the mixture was stirred at rt overnight. It was cooled to 0° C. and quenched with 10% aqueous citric acid. The organic layer was then concentrated and the mixture was diluted with water and CH$_2$Cl$_2$. Extracted 3× with CH$_2$Cl$_2$. The combined organics were dried (anhd. Na$_2$SO$_4$), filtered, and concentrated. The residue was purified by column chromatography to give the title compound. $^1$H NMR (500 MHz, CDCl$_3$) δ 3.91-4.05 (m, 4H), 3.77-3.90 (m, 2H), 3.60-3.70 (m, 3H), 3.44 (dd, 1H, J=8.8 Hz, 11.0 Hz), 1.14-1.82 (m, 9H).

6-(pent-4-en-1-yl)-1,4,8-trioxaspiro[4.5]decane (6-5)

To a mixture of oxalyl chloride (2M in CH$_2$Cl$_2$, 1.17 mL, 2.34 mmol) in CH$_2$Cl$_2$ (4 mL) at −78° C. was added a mixture of DMSO (0.221 mL, 3.12 mmol) in CH$_2$Cl$_2$ (1 mL) dropwise. The mixture was stirred for 10 min. 3-(4-hydroxybutyl)tetrahydro-4H-pyran-4-one (0.337 g, 1.56 mmol) in CH$_2$Cl$_2$ (3 mL+1 mL rinse) was then added. The mixture was stirred for another 15 min and TEA (1.1 mL, 7.79 mmol) was added. The reaction was stirred for 10 more min at −78° C. The resulting mixture was warmed to it and stirred for 30 minutes. It was quenched with water and sat'd aq. NaHCO$_3$. Extracted 3× with CH$_2$Cl$_2$. The combined organics were dried (anhd. Na$_2$SO$_4$), filtered, and concentrated. The residue was purified by column chromatography and used in the next step.

To a mixture of methyltriphenylphosphonium bromide (0.920 g, 2.58 mmol) in TI IF (10 mL) under N$_2$ at it was added NaHMDS (2M in THF, 1.30 mL, 2.58 mmol). The mixture was stirred at rt for 1 hr. 4-(1,4,8-trioxaspiro[4.5]dec-6-yl)butanal (0.276 g, 1.29 mmol) was then added and the reaction was stirred at it for 1 hr. It was quenched with sat'd. aq. NH$_4$Cl and extracted 3× with Et$_2$O. The combined organics were dried (anhd. Na$_2$SO$_4$), filtered, and concentrated. The residue was purified by column chromatography to give the title compound. $^1$H NMR (500 MHz, CDCl$_3$) δ 5.75-5.86 (m, 1H), 4.91-5.03 (m, 2H), 3.91-4.05 (m, 4H), 3.78-3.90 (m, 2H), 3.62-3.71 (m, 1H), 3.43 (dd, 1H, J=9.0 Hz, 11.2 Hz), 1.98-2.12 (m, 2H), 1.11-1.81 (m, 7H).

3,4,6,7,8,8a-hexahydro-1H-isochromene (6-6)

To a mixture of 6-(pent-4-en-1-yl)-1,4,8-trioxaspiro[4.5]decane (0.242 g, 1.14 mmol) in THF (3 mL) was added 10%

HCl (3 mL) and stirred for 1 hr at rt. It was diluted with water and extracted 3× with ether. The combined organics were washed with brine, dried, filtered and concentrated. The residue was used directly in the next step.

To a mixture of methyltriphenylphosphonium bromide (0.849 g, 2.38 mmol) in THF (8 mL) under $N_2$ at rt was added NaHMDS (2M in THF, 1.19 mL, 2.38 mmol). The mixture was stirred at rt for 1 hr. 3-(pent-4-en-1-yl)tetrahydro-4H-pyran-4-one (0.200 g, 1.19 mmol) in THF (2 mL+1 mL rinse) was then added and the reaction was stirred at rt for 1 hr. It was quenched with sat'd. aq. $NH_4Cl$ and extracted with Ether. The combined organics were dried (anhd. $Na_2SO_4$), filtered, and concentrated. The residue was further purified via column chromatography.

A mixture of 4-methylidene-3-(pent-4-en-1-yl)tetrahydro-2H-pyran (0.198 g, 1.19 mmol) in $CH_2Cl_2$ (20 mL) was degassed (3×$N_2$/pump). Zhan-Ib (0.044 g, 0.060 mmol) was added, the reaction was degassed again, and stirred at rt for 1 hr. The resulting mixture was concentrated and purified by silica gel chromatography to provide the title compound. $^1$H NMR (500 MHz, $CDCl_3$) δ 5.47 (s, 1H), 3.90-4.10 (m, 2H), 3.26-3.35 (m, 1H), 2.94 (t, 1H, J=11.0 Hz), 2.24-2.40 (m, 2H), 1.74-2.07 (m, 3H), 1.65-1.76 (m, 2H), 1.38-1.49 (m, 1H), 0.96-1.07 (m, 1H).

Octahydrooxireno[e]isochromene (6-7)

To a mixture of 3,4,6,7,8,8a-hexahydro-1H-isochromene (0.120 g, 0.868 mmol) in $CH_2Cl_2$ (6 mL) at 0° C. was added MCPBA (~77%, 0.300 g, 1.30 mmol). The mixture was stirred at rt for 1 hr. It was quenched with sat'd. aq. sodium sulfite. The mixture was diluted with $CH_2Cl_2$ and said. aq. $NaHCO_3$ then extracted with $CH_2Cl_2$. The combined organics were dried (anhd. $Na_2$—$SO_4$), filtered, and concentrated. The residue was purified by column chromatography to give the title compound.

(4aR,5R,8aS)-5-[(4-fluorophenyl)amino]octahydro-4-aH-isochromen-4a-ol (6-8)

To a mixture of 4-fluoroaniline (0.119 g, 1.07 mmol) in $CH_2Cl_2$ (1 mL) at 0° C. was added trimethylaluminum (2M in toluene, 0.535 mL) dropwise. The mixture was warmed to rt and stirred for 30 min. A mixture of cis and trans octahydrooxireno[e]isochromene (0.033 g, 0.214 mmol) in CH2Cl2 (1 mL) was then added and the mixture was stirred at rt overnight. The reaction mixture was cooled to 0° C. and treated with 50% NaOH (1 mL) then water (1 mL). It was diluted with more water and extracted 3× with $CH_2Cl_2$. The combined organics were dried, filtered and concentrated. The residue was purified by column chromatography to give the title compound. $^1$H NMR (500 MHz, $CDCl_3$) δ 6.92 (t, 2H, J=8.8 Hz), 6.71 (dd, 2H, J=4.2 Hz, 8.8 Hz), 3.81-3.87 (m, 1H), 3.61 (dd, 1H, J=4.6 Hz, 11.2 Hz), 3.50 (t, 1H, J=11.0 Hz), 3.32 (s, 1H), 2.15-2.26 (m, 1H), 1.89-2.07 (m, 2H), 1.59-1.69 (m, 2H), 1.45-1.58 (m, 1H), 1.20-1.37 (m, 4H). HRMS (ES) m/z M+H calc'd.: 266.1551. found: 266.1549

TABLE 6

| # | Structure | MS M + 1 |
|---|---|---|
| 6-9 | 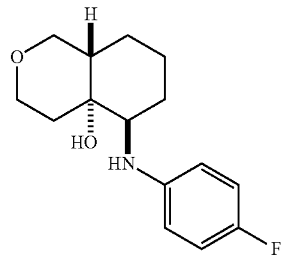 [SMILES: O[C@]12CCOC[C@@H]1CCC[C@H]2Nc1ccc(F)cc1] | 266.1549 |
| 6-10 | 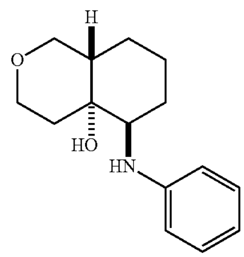 [SMILES: O[C@]12CCOC[C@@H]1CCC[C@H]2Nc1ccccc1] | 248.1646 |
| 6-11 | 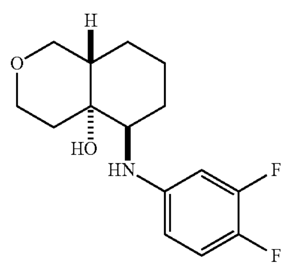 [SMILES: O[C@]12CCOC[C@@H]1CCC[C@H]2Nc1ccc(F)c(F)c1] | 284.1458 |

Example 7

(4aS,5R,8aR)-5-[(4-fluorophenyl)amino]hexahydro-2H-chromen-4a(5H)-ol

Reaction Scheme 7

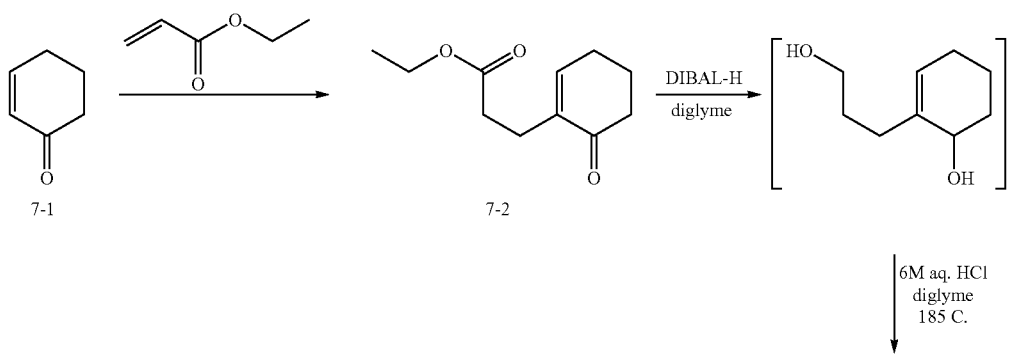

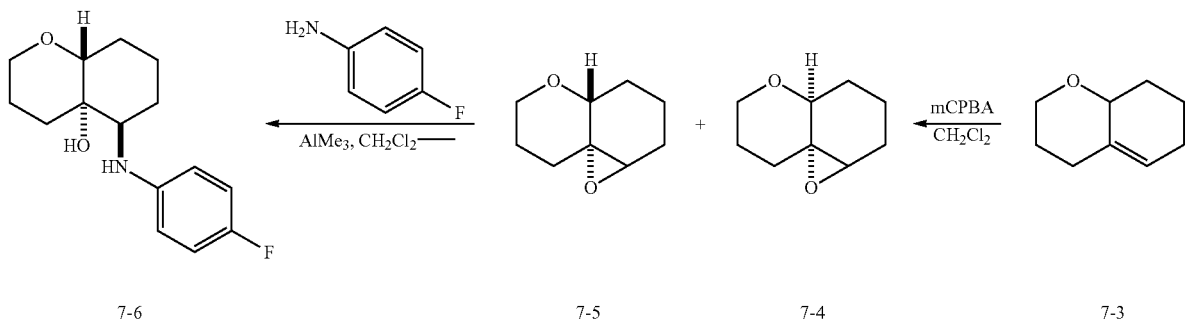

7-6  7-5  7-4  7-3 ethyl 3-(6-oxocyclohex-1-en-1-yl)propanoate (7-2)

Compound 7-2 and compound 7-3 were made according to literature reference (Yeh, M-C; Lee, Y-C, Young, T-C, Synthesis, 2006, 21, 3621-3624). To a solution of 5 mL of cyclohex-2-en-1-one in 100 mL 1,3-dimethyl-2-imidazolidinone (DMEU) was added 7.4 mL ethyl acrylate followed by 4 mL 2,3,4,6,7,8,9,10-octahydropyrimido[1,2-a]azepine (DBU). The reaction was heated to 185° C. in a sealed tube overnight, then cooled to RT and added to water. The resultant mixture was extracted with $Et_2O$, and the crude extract was dried over $Na_2SO_4$ then filtered, concentrated, and purified on silica (0-60% $Et_2O$ in hexanes) to provide the title compound.

3,4,6,7,8,8a-hexahydro-2H-chromene (7-3)

A solution of 48 mL diisobutylaluminum hydride (1.0 M in cyclohexane) was cooled to −78° C. and a solution of 2.335 g ethyl 3-(6-oxocyclohex-1-en-1-yl)propanoate in 48 mL THF was added. The reaction was warmed to 0° C. and stirred for one hour, then warmed to RT and stirred for one more hour. The reaction was not complete at this point, so 10 mL additional diisobutylaluminum hydride solution was added the reaction was and stirred at RT for two hours. The reaction was then cooled to −78° C. and then 25 mL 6 M HCl was added dropwise. After the addition was complete, the reaction was allowed to return to RT and was stirred overnight. The reaction was diluted with 200 mL $Et_2O$ then washed 2× with water, then with brine. The organic layer was dried over $Na_2SO_4$ then filtered, concentrated, and purified on silica gel to provide the title compound.

(1aS,4aS,8aS)-hexahydro-1aH,6H-oxireno[e]chromene (7-4) and (1aS,4aR,8aS)-hexahydro-1aH,6H-oxireno[e]chromene (7-5)

Dissolved 431 mg 3,4,6,7,8,8a-hexahydro-2H-chromene in 12.5 mL $CH_2Cl_2$ then added 700 mg meta-chloroperoxybenzoic acid (77% pure) and stirred for several hours. TLC shows two products. Quenched excess oxidant with saturated sodium sulfite, diluted with water, then extracted with $CH_2Cl_2$ and dried extract over $Na_2SO_4$. Filtered, concentrated, then purified on silica gel to yield the individual title compounds. Compound 7-4: $^1$H NMR (500 MHz, $CDCl_3$) δ=1.26-1.31 (m, 1H), 1.42-1.46 (m, 1H), 1.49-1.58 (m, 2H), 1.65-1.72 (m, 1H), 1.76-1.88 (m, 3H), 1.95-2.03 (m, 2H), 3.05 (d, J=4.9 Hz, 1H), 3.49 (td, $J_1$=11.5 Hz, $J_2$=2.9 Hz, 1H), 3.72-3.74 (m, 1H), 3.97-4.01 (m, 1H) ppm. (7-5) $^1$H NMR (500 MHz, $CDCl_3$) δ 1.21-1.31 (m, 1H), 1.34-1.39 (m, 1H), 1.47-1.69 (m, 4H), 1.77-1.88 (m, 2H), 2.01-2.13 (m, 2H), 3.07 (d, 3.9 Hz, 1H), 3.60-3.66 (m, 2H), 4.05-4.09 (m, 1H) ppm.

(4aS,5R,8aR)-5-[(4-fluorophenyl)amino]hexahydro-2H-chromen-4a(5H)-ol (7-6)

Dissolved 55 uL 4-fluoroaniline in 1.3 mL $CH_2Cl_2$ then cooled to 0° C. and added 0.21 mL $AlMe_3$ (2.0M in toluene). Warmed to RT, stirred for 30 minutes, then added 50 mg (1aS,4aR,8aS)-hexahydro-1aH,6H-oxireno[e]chromene (7-5) in 1.0 mL $CH_2Cl_2$. Stirred for two hours at RT, then sat. sodium potassium tartrate solution was added dropwise to the reaction, allowing gas evolution to cease between drops, until no further gas evolution was noted. The mixture was diluted with water, then extracted with $CH_2Cl_2$. The extract was dried over $Na_2SO_4$, filtered, concentrated, then purified on silica (0-40% EtOAc in hexanes) to yield the title compound. $^1$H NMR (500 MHz, $CDCl_3$) δ=1.42-1.69 (m, 7H), 1.90-2.09 (m, 3H), 2.47 (s, 1H), 3.38-3.48 (m, 3H), 3.53 (s, broad, 1H), 3.92-3.95 (m, 1H), 6.54-6.59 (m, 2H), 6.84-7.26 (m, 2H) ppm. HRMS (ES) m/z M±H calc'd: 266.1551. found 266.1551.

TABLE 7

| # | Structure | MS M + 1 |
|---|---|---|
| 7-7 | 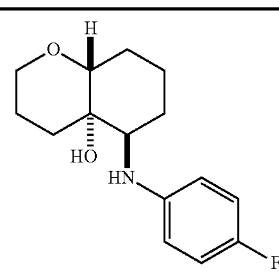 | 266.1551 |

TABLE 7-continued
| # | Structure | MS M + 1 |
|---|-----------|----------|
| 7-8 | 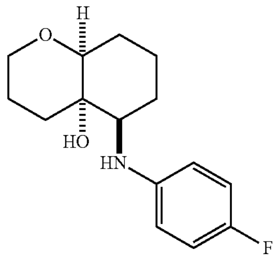 [SMILES: O[C@]12CCCO[C@H]1CCC[C@H]2Nc1ccc(F)cc1] | 266.1552 |
| 7-9 | 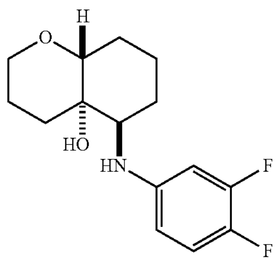 [SMILES: O[C@]12CCCO[C@@H]1CCC[C@H]2Nc1ccc(F)c(F)c1] | 284.1454 |
| 7-10 | 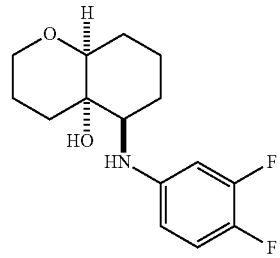 [SMILES: O[C@]12CCCO[C@H]1CCC[C@H]2Nc1ccc(F)c(F)c1] | 284.1454 |
Example 8
(4aR,5R,8S,8aR)-5-[(4-fluorophenyl)amino]-8-(methoxymethyl)hexahydro-2H-chromen-4a(5H)-5-ethenyl-3,4-dihydro-2H-pyran (8-2)
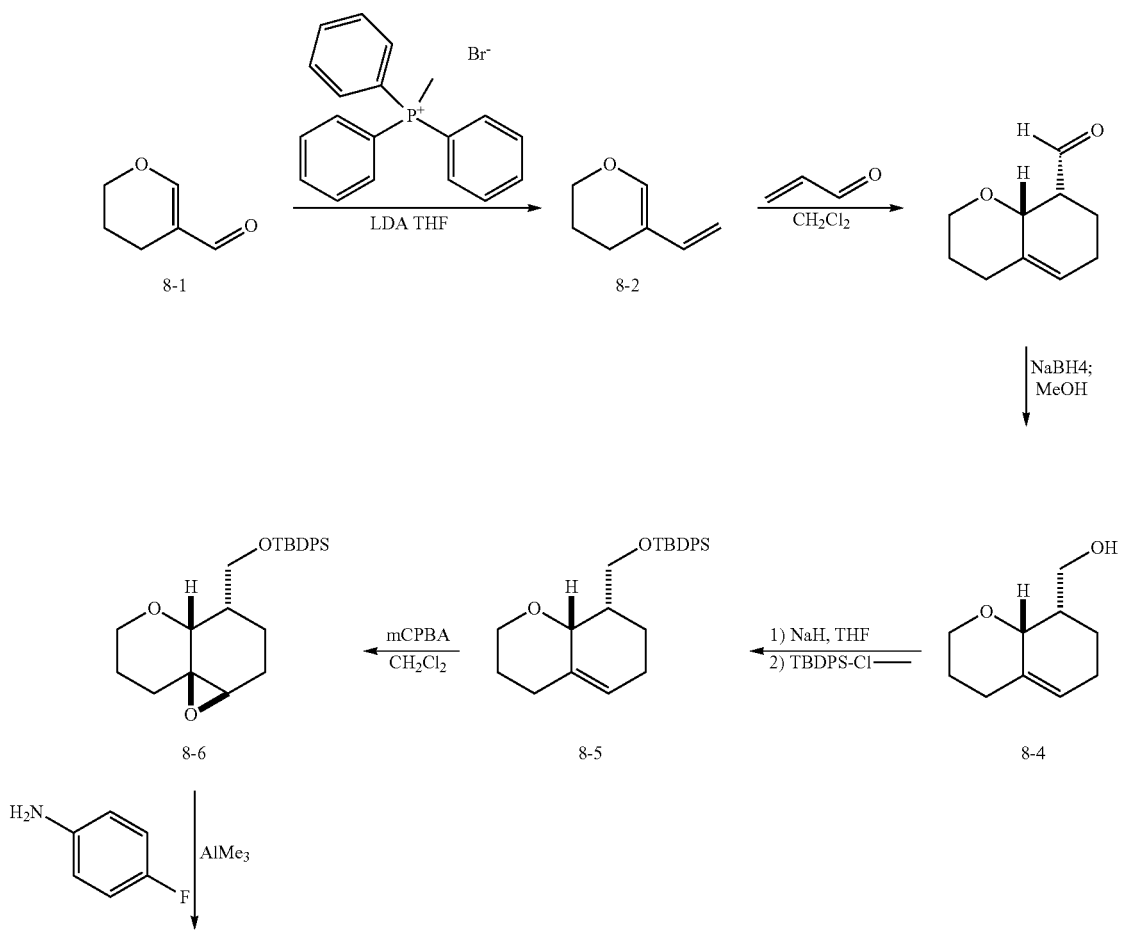

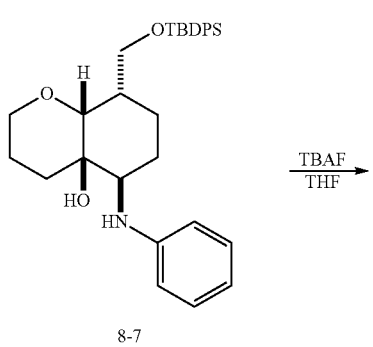
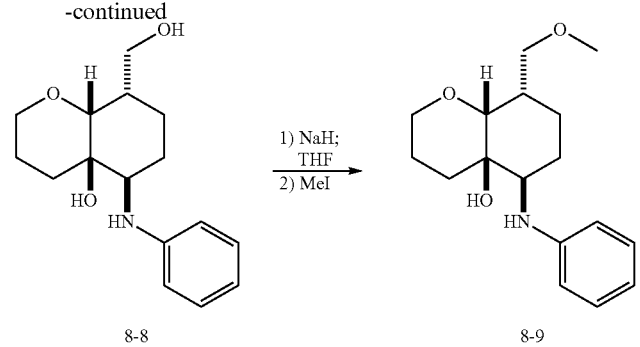

8-7   8-8   8-9

A solution of 21.0 g methyltriphenylphosphonium bromide in 120 mL THF was cooled to 0 C and added 30 mL lithium diisopropylamide (2.0 M in THF) and stirred for one hour at 0 C. 5.09 g 3,4-dihydro-2H-pyran-5-carbaldehyde in 5 mL THF was then added slowly via syringe to the reaction mixture, and the reaction was warmed to RT and stirred overnight. The reaction was added to water, extracted WI petroleum ether and dried over $Na_2SO_4$. Subsequent cooling in a freezer for several hours caused much of the triphenylphosphine oxide to crystallize out of solution, and the drying agent and phosphine byproduct were removed by filtration. The solution was concentrated in vacuo, and the remaining crude mixture was distilled at reduced pressure to afford the title compound. $^1$H NMR (500 MHz, CDCl$_3$) δ=1.89-1.94 (m, 2H), 2.15 (t, J=6.3 Hz, 2H), 3.99 (t, J=5.1 Hz, 2H), 4.77 (d, J=10.7 Hz, 1H), 4.90 (d, J=17.3 Hz, 1H), 6.24 (dd, J$_1$=17.3 Hz, J$_2$=10.7 Hz, 1H), 6.57 (s, 1H) ppm.

(8R,8aR)-3,4,6,7,8,8a-hexahydro-2H-chromene-8-carbaldehyde (8-3)

A mixture of 2.613 g 5-ethenyl-3,4-dihydro-2H-pyran and 8.9 mL acrolein (90% pure) was dissolved in 39 mL $CH_2Cl_2$ and stirred overnight at RT. The reaction was added to water and extracted with $CH_2Cl_2$. The crude extract was filtered, concentrated using a rotovap, then purified on silica gel to provide the title compound. $^1$H NMR (500 MHz, CDCl$_3$) δ=1.64-1.98 (m, 5H), 2.04-2.16 (m, 1H), 2.23-2.29 (m, 1H), 2.34-2.38 (m, 1H), 2.60-2.64 (m, 1H), 3.55-3.61 in, 1H), 3.99-4.04 (m, 1H), 4.21 (d, J=5.6 Hz, 1H), 5.55 (s, 1H), 9.88 (s, 1H) ppm.

(8S,8aR)-3,4,6,7,8,8a-hexahydro-2H-chromen-8-ylmethanol (8-4)

202 mg (8R,8aR)-3,4,6,7,8,8a-hexahydro-2H-chromene-8-carbaldehyde was dissolved in 8 mL MeOH and the solution was cooled to 0° C. and 52 mg sodium borohydride was added slowly. The reaction was stirred for several hours and gradually warmed to RT. The methanol was removed using a rotovap and the residue was diluted with $CH_2Cl_2$ and added to sat. $NH_4Cl$. The mixture was separated, and the aqueous was extracted with $CH_2Cl_2$. The crude extract was dried over $Na_2SO_4$, filtered, concentrated, then purified on silica gel to provide the title compound. $^1$H NMR (400 MHz, CDCl$_3$) δ=1.46-1.80 (m, 4H), 1.84-2.10 (m, 3H), 2.13-2.38 (m, 2H), 2.78-2.86 (m, 1H), 3.52-3.62 (m, 1H), 3.66-3.76 (m, 1H), 3.76-3.87 (m, 1H), 3.94-3.47 (m, 2H), 5.52 (s, 1H) ppm.

tert-butyl[(8S,8aR)-3,4,6,7,8,8a-hexahydro-2H-chromen-8-ylmethoxy]diphenylsilane (8-5)

To a solution of 360 mg (8S,8aR)-3,4,6,7,8,8a-hexahydro-2H-chromen-8-ylmethanol added 2.2 mL DMF, then 224 mg imidazole followed by 0.66 mL tert-butyl(chloro)diphenylsilane. The reaction was stirred overnight at RT, then added to water and extracted with diethyl ether. The crude extract was dried over $Na_2SO_4$, filtered, concentrated, then purified on silica gel to provide the title compound. $^1$H NMR (500 MHz, CDCl$_3$) δ=1.05 (s, 9H), 1.37-1.46 (m, 1H), 1.54-1.58 (m, 1H), 1.63-1.73 (m, 2H), 1.86-2.09 (m, 3H), 2.16-2.24 (m, 1H), 2.25-2.31 (m, 1H), 3.53 (m, 1H), 3.60 (dd, J$_1$=9.8 Hz, J$_2$=7.7 Hz, 1H), 3.80 (d, J=5.1 Hz, 1H), 3.90 (dd, 10.0 Hz, J2=7.4 Hz, 1H), 3.94-3.98 (m, 1H), 4.49-5.52 (m, 1H), 7.35-7.42 (m, 6H), 7.67-7.72 (m, 4H) ppm.

tert-butyl[(1aR,4S,4aR,8aR)-hexahydro-1aH,6H-oxireno[e]chromen-4-ylmethoxy]diphenylsilane (8-6)

Dissolved 424 mg text-butyl[(8S,8aR)-3,4,6,7,8,8a-hexahydro-2H-chromen-8-ylmethoxy]diphenylsilane in 10 mL $CH_2Cl_2$ then added 264 mg meta-chloroperoxybenzoic acid and stirred at RT overnight. Quenched excess oxidant with saturated sodium sulfite, diluted with water, then extracted with $CH_2Cl_2$ and dried extract over $Na_2SO_4$. Filtered, concentrated, then purified on silica gel to provide the title compound. $^1$H NMR (500 MHz, CDCl$_3$) δ=1.05 (s, 9H), 1.16-1.22 (m, 1H), 1.24-1.34 (m, 1H), 1.42-1.46 (m, 1H), 1.76-1.91 (m, 2H), 1.99-2.11 (m, 2H), 3.04 (d, J=5.1 Hz), 3.38-3.48 (m, 2H), 3.68 (t, J=9.0 Hz), 3.87 (d, J=2.9 Hz), 3.94-3.98 (m, 1H), 7.35-7.43 (m, 6H), 7.64-7.69 (m, 4H) ppm.

(4aR,5R,8S,8aR)-8-({[tert-butyl(diphenyl)silyl]oxy}methyl)-5-[(4-fluorophenyl)amino]hexahydro-2H-chromen-4a(5H)-ol (8-7)

Dissolved 114 uL 1 in 2.4 mL $CH_2Cl_2$ then added 0.59 mL trimethylaluminum (2.0 M in toluene). Stirred for 45 minutes then added 100 mg tert-butyl[(1aS,4aR,8aS)-hexahydro-1aH,6H-oxireno[e]chromen-4-ylmethoxy]diphenylsilane in 0.50 mL $CH_2Cl_2$. The reaction was stirred overnight at RT, then sat. sodium potassium tartrate solution was added dropwise to the reaction, allowing gas evolution to cease between drops, until no further gas evolution was noted. The mixture was diluted with water, then extracted with $CH_2Cl_2$. The extract was dried over $Na_2SO_4$, filtered, concentrated, then purified on silica gel to provide the title compound. $^1$H NMR (500 MHz, CDCl$_3$) δ=1.05 (s, 9H), 1.26-1.33 (m, 3H), 1.56-1.65 (m, 2H), 1.71-1.76 (m, 1H), 1.78-1.86 (m, 1H), 2.11-

2.16 (m, 1H), 2.21-2.28 (m, 1H), 2.32-2.42 (m, 1H), 3.40-3.48 (m, 2H), 3.52-3.57 (m, 2H), 3.76 (t, J=9.0 Hz, 1H), 4.07 (dd, $J_1$=11.5 Hz, $J_2$=5.4 Hz, 1H), 4.58 (d, J=11.5 Hz), 6.48-6.52 (m, 2H), 6.84-6.88 (m, 2H), 7.36-7.44 (m, 6H), 7.68-7.71 (m, 4H) ppm.

(4aR,5R,8S,8aR)-5-[(4-fluorophenyl)amino]-8-(hydroxymethyl)hexahydro-2H-chromen-4a(5H)-ol (8-8)

Dissolved 68 mg (4aS,5R,8S,8aR)-8-({[tert-butyl(diphenyl)silyl]oxy}methyl)-5-[(4-fluorophenyl)amino]hexahydro-2H-chromen-4a(5H)-ol in 4 mL tetrabutylammonium fluoride solution (2.0 M in THF) and stirred overnight at RT. Excess solvent was removed using a rotovap, then the residue was diluted with $CH_2Cl_2$, added to water, and extracted with $CH_2Cl_2$. The crude extract was dried over $Na_2SO_4$, filtered, concentrated, then purified on silica gel to provide the title compound. $^1$H NMR (500 MHz, $CDCl_3$) δ=1.32-1.39 (m, 1H), 1.55-1.90 (m, 5H), 2.06-2.16 (m, 2H), 2.24-2.28 (m, 1H), 2.34-2.46 (m, 1H). 3.46 (s, 1H), 3.49-3.56 (m, 2H), 3.68-3.75 (m, 1H), 3.77-3.82 (m, 1H), 4.12 (dd, $J_1$=11.4 Hz, $J_2$=6.0 Hz, 1H), 4.64 (d, J=11.2 Hz), 6.50-6.56 (m, 2H), 6.85-6.90 (m, 2H) ppm.

(4aR,5R,8S,8aR)-5-[(4-fluorophenyl)amino]-8-(methoxymethyl)hexahydro-2H-chromen-4a(5H)-ol (8-9)

Dissolved 95 mg (4aS,5R,8S,8aR)-5-[(4-fluorophenyl)amino]-8-(hydroxymethyl)hexahydro-2H-chromen-4a(5H)-ol in 2.1 mL THF then added 39 mg NaH. The reaction was stirred for 1.5 hours at RT, then diluted with an additional 1 mL of THF before adding 50 uL iodomethane. The reaction was stirred overnight at RT, then added to sat. $NH_4Cl$. The mixture was diluted with water and extracted with $CH_2Cl_2$. The crude extract was dried over $Na_2SO_4$ then filtered, concentrated, then purified on silica gel to provide the title compound. $^3$H NMR (500 MHz, $CDCl_3$) δ=1.34-1.40 (m, 2H), 1.54-1.62 (m, 2H), 1.72-1.77 (m, 1H), 1.78-1.87 (m, 1H), 2.10-2.16 (m, 1H), 2.22-2.30 (m, 1H), 2.32-2.42 (m, 1H), 3.29 (dd, $J_1$=9.3 Hz, $J_2$=6.6 Hz, 1H), 3.31-3.33 (m, 1H), 3.44-3.50 (m, 2H), 3.53 (bd, J=11.2 Hz), 4.09 (dd, $J_z$=11.6 Hz, $J_2$=6.5 Hz, 1H), 4.58 (d, J=11.2 Hz) ppm. HRMS (ES) m/z calc'd: 310.1813. found 310.1811.

TABLE 8

| # | Structure | MS M + 1 |
|---|-----------|----------|
| 8-10 | | 310.1811 |
| 8-11 | 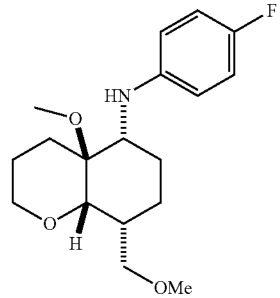 [SMILES: COC[C@H]1CC[C@@H](Nc2ccc(F)cc2)[C@@]2(OC)CCCO[C@@H]12] | 324.1968 |
| 8-12 | 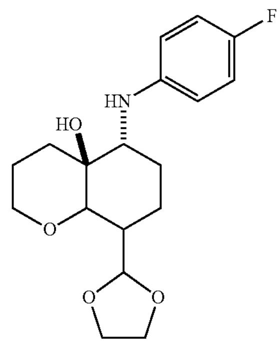 [SMILES: O[C@]12CCCOC1C(C1OCCO1)CC[C@H]2Nc1ccc(F)cc1] | 338.1763 |
| 8-13 | 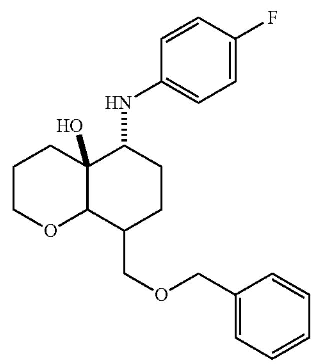 [SMILES: O[C@]12CCCOC1C(COCc1ccccc1)CC[C@H]2Nc1ccc(F)cc1] | 386.4 |
| 8-14 | 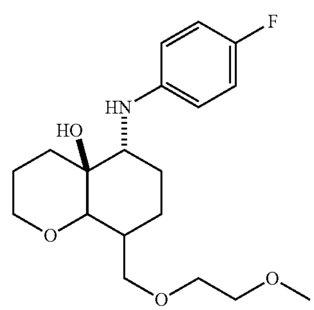 [SMILES: COCCOCC1CC[C@@H](Nc2ccc(F)cc2)[C@@]2(O)CCCOC12] | 354.4 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

BIOLOGICAL EXAMPLES

High Throughput Calcium Imaging Assay

The assay was dependent on detecting the change in intracellular Ca2+ concentration following activation of the channel in cells stably expressing the TRPA1 channel. Activation of the TRPA1 channel was followed by Ca2+ influx. Ca2+ increase was quantified through the use of a fluorescent Ca2+ indicator that was loaded into the cells. Compounds which inhibited Ca2+ increase were considered "hits" warranting additional examination.

The HEK293 FlpIn cell line (Invitrogen) was stably transfected as per the manufacturers guidelines with a construct encoding a human TRPA1 protein with the amino acid sequence depicted in SEQ ID NO: 1. The resulting cell line was maintained in the growth medium recommended by the manufacturer and supplemented with 100 ug/mL Hygromycin B to promote the selection of cells stably expressing the TRPA1 channel. After growing to confluency, cells were plated at a density of 24,000 cells/well in 384 well Black/Clear Microtest plates (Falcon) in the recommended growth medium supplemented with hygromycin, and allowed to grow for 20-24 hours resulting in a ~90% confluent monolayer of cells. Cells were then loaded with assay buffer containing the Ca2+ dye Fluo-4AM (Invitrogen) to a final concentration of 4 uM, and incubated for 60 minutes at room temperature in the dark. The assay buffer consisted of 138 mM NaCl, 5.33 mM KCl, 1.26 mM CaCl2, 0.49 mM MgCl2, 0.41 mM MgSO4 5.56 mM D-glucose, 0.44 mM KH2PO4, 0.34 mM Na2HPO4, 20 mM HEPES, 2.5 mM Probenecid, and 4% TR-40; pH 7.8. Following 1 hour dye loading, cells were assayed using the FLIPR TETRA (Molecular Devices) which permits excitation of the Fluo-4AM dye, and subsequent recording of emission spectra according to the manufacturer's guidelines. A total of 5 baseline readings were acquired prior to each reagent addition, after which, readings were acquired at a rate of 1 every 3 seconds for 195 seconds, and then 1 every 10 seconds for an additional 420 seconds. During the assay, reagents were added and mixed after each addition by the FLIPR TETRA pippetor. EC60 concentration of Cinnamaldehyde was determined before the screening assay, and used as the activating concentration henceforth. For the screening assay, the baseline reading was taken, followed by addition of 10 uL of a compound stock at six-times the final concentration, followed by 615 seconds of read time as previously described. Following baseline readings, 10 μl, of six-times final concentration Cinnamaldehyde was added to each well, achieving a final concentration of 10 uM compound, and on average, 12 uM Cinnamaldehyde (depending on the EC60 derived during that experiment). Following addition of Cinnamaldehyde, readings were taken for 615 seconds as previously described. Negative controls consisted of HEK293 FlpIn TRPA1 cells exposed to compound vehicle and then Cinnamaldehyde. Positive controls consisted of HEK293 FlpIn TRPA1 cells exposed to a concentration of reference antagonist capable of fully blocking the response to Cinnamaldehyde. "Hits" were identified as compounds which inhibited the fluorescence response in the presence of Cinnamaldehyde as compared to the negative and positive controls. IC50 values were determined for compounds defined as "hits" which reached fully inhibition. This cell-based fluorescence assay was used to determine Ca2+ influx through the channel in the presence of compound at the following concentrations: 10 uM, 3.33 uM, 1.11 uM, 0.37 uM, 0.12 uM, 0.041 uM, 0.014 uM, 0.0046 uM, 0.0015 uM, and 0.00051 uM. Highly potent "hits" were also investigated at 1000 nM, 333.33 nM, 111.11 nM, 37.04 nM, 12.35 nM, 4.12 nM, 1.37 nM, 0.46 nM, 0.15 nM, and 0.05 nM.

Human TRPA1 - NM_007332.1

[SEQ ID. NO: 1]

MKCSLRKMWRPGEKKEPQGVVYEDVPDDTEDFKESLKVVFEGSAYGLQN

FNKQKKLKTCDDMDTFFLHYAAAEGQIELMEKITRDSSLEVLHEMDDYG

NTPLHCAVEKNQIESVKFLLSRGANPNLRNFNMMAPLHIAVQGMNNEVM

KVLLEHRTIDVNLEGENGNTAVIIACTTNNSEALQILLNKGAKPCKSNK

WGCFPIHQAAFSGSKECMEIILRFGEEHGYSRQLHINFMNNGKATPLHL

AVQNGDLEMIKMCLDNGAQIDPVEKGRCTAIHFAATQGATEIVKLMISS

YSGSVDIVNTTDGCHETMLHRASLFDHHELADYLISVGADINKIDSEGR

SPLILATASASWNIVNLLLSKGAQVDIKDNFGRNFLHLTVQQPYGLKNL

RPEFMQMQQIKELVMDEDNDGCTPHLYACRQGGPGSVNNLLGFNVSIHS

KSKDKKSPLHFAASYGRINTCQRLLQDISDTRLLNEGDLHGMTPLHLAA

KNGHDKVVQLLLKKGALFLSDHNGWTALHHASMGGYTQTMKVILDTNLK

CTDRLDEDGNTALHFAAREGHAKAVALLLSHNADIVLNKQQASFLHLAL

HNKRKEVVLTIIRSKRWDECLKIFSHNSPGNKCPITEMIEYLPECMKVL

LDFCMLHSTEDKSCRDYYIEYNFKLQCPLEFTKKTPTQDVIYEPLTALN

AMVQNNRIELLNHPVCKEYLLMKWLAYGFRAHMMNLGSYCLGLIPMTIL

VVNIKPGMAFNSTGIINETSDHSEILDTTNSYLIKTCMILVFLSSIFGY

CKEAGQIFQQKRNYFMDISNVLEWIIYTTGIIFVLPLFVEIPAHLQWQC

GAIAVYFYWMNFLLYLQRFENCGIFIVMLEVILKTLLRSTVVFIFLLLA

FGLSFYILLNLQDPFSSPLLSIIQTFSMMLGDINYRESFLEPYLRNELA

HPVLSFAQLVSFTIFVPIVLMNLLIGLAVGDIAEVQKHASLKRIAMQVE

LHTSLEKKLPLWFLRKVDQKSTIVYPNKPRSGGMLFHIFCFLFCTGEIR

QEIPNADKSLEMEILKQKYRLKDLTFLLEKQHELIKLIIQKMEIISETE

DDDSHCSFQDRFKKEQMEQRNSRWNTVLRAVKAKTHHLEP

The TRPA1 antagonists of this invention were found to have IC50's for inhibition of human TRPA1 of 100 micromolar or less, in some cases 50 micromolar or less, in some cases 20 micormolar or less, in some cases 10 micromolar or less, in some cases 5 micromolar or less, in some cases 2 micromolar or less, in some cases 1 micromolar or less, in some cases 500 nanomolar or less, in some cases 250 nanomolar or less, in some cases 200 nanomolar or less, in some cases 100 nanomolar or less, and in some cases 20 nanomolar or less. In certain embodiments, the TRPA1 antagonists of this invention inhibit one or both of inward and outward TRPA1-mediated current with an IC50 of 100 micromolar or less, in some cases 50 micromolar or less, in some cases 20 micormolar or less, in some cases 10 micromolar or less, in some cases 5 micromolar or less, in some cases 2 micromolar or less, in some cases 1 micromolar or less, in some cases 500 nanomolar or less, in some cases 200 nanomolar or less, and in some cases 100 nanomolar or less, in some cases 50 nanomolar or less and in some cases 20 nanomolar or less. In certain embodiments, the TRPA1 antagonist inhibits at least 95% of TRPA1-mediated current or TRPA1-mediated ion flux when administered at 5 micromolar or less, and even more preferably at 1 micromolar or less.

Ideally TRPA1 inhibitors of the claimed invention have an 1050 for TRPA1 inhibition that, at that concentration, does not cause QT interval elongation in the patient nor alter temperature regulation in the patient.

In certain embodiments, the pharmaceutical composition comprises an effective amount of any of the compound of formula I, wherein the compound inhibits TRPA1 (e.g., a TRPA1-mediated current and/or TRPA1-mediated ion flux) with an $IC_{50}$ of 10 micromolar or less. For example, in Table C below nanomolar IC50 values were observed.

TABLE C

| TRPA1 hFLIPR IC50 (nM) | IUPAC name |
|---|---|
| 19 | (4aR,8aR)-4-[(4-fluorophenyl)amino]octahydronaphthalen-4a(2H)-ol |
| 54 | (4R,4aR,8aR)-4-(phenylamino)octahydronaphthalen-4a(2H)-ol |
| 35 | (4aR,5S)-5-[(4-fluorophenyl)amino]-8-(methoxymethyl)hexahydro-2H-chromen-4a(5H)-ol |
| 850 | (4aR,5S,8aS)-5-[(4-fluorophenyl)amino]hexahydro-2H-chromen-4a(5H)-ol |

TABLE C-continued

| TRPA1 hFLIPR IC50 (nM) | IUPAC name |
|---|---|
| 520 | (4aS,5R,8aS)-5-[(4-fluorophenyl)amino]hexahydro-2H-chromen-4a(5H)-ol |

What is claimed is:

1. A compound represented by Formula I:

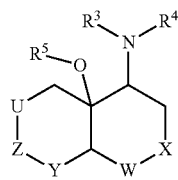

I or a pharmaceutically acceptable salt thereof, a solvate, hydrate, stereoisomer, or enantiomer of the compound or its salt wherein:
W represents $CH_2$, or $CHR^4$,
U, X, Y, and Z independently represent $CH_2$,
$R^2$ represents hydrogen, or $C_{1-6}$ alkyl;
$R^5$ represents hydrogen;
one of $R^3$ and $R^4$ independently represents H or $C_{1-6}$ alkyl, and the other represents $(CHR^2)_n C_{5-10}$ heterocyclyl, $(CHR^2)_n C_{6-10}$ aryl, $(CHR^2)_n C_{3-10}$ cycloalkyl, or $C_{1-6}$ alkyl; said alkyl, cycloalkyl, heterocyclyl and aryl optionally substituted with 1 to 3 groups of $R^a$, wherein n=0 or 1;
$R^a$ represents $C_{1-6}$ alkyl, halogen, hydroxyl, $OR^2$, $(CH_2)_n CF_3$, $C_{3-6}$ cycloalkyl, $C(O)N(R^2)_2$, $C(R^2)_2 OR^2$, $C(O)R^2$, $NO_2$, CN, $N(R^2)_2$, $C(O)OR^2$, $(CH_2)_n C_{5-10}$ heterocyclyl, or $(CH_2)_n C_{6-10}$ aryl, said heterocyclyl and aryl optionally substituted with 1 to 3 groups of $C_{1-6}$ alkyl, halogen, hydroxyl, $(CH_2)_n CF_3$, or CN; and
n represents 0 to 4.

2. The compound according to claim 1 wherein $R^5$ is hydrogen, one of $R^3$ and $R^4$ is hydrogen, or $CH_3$, and the other is selected from the group consisting of $(CHR^2)_n C_{5-10}$ heterocyclyl, $(CHR^2)_n C_{6-10}$ aryl, $(CHR^2)_n C_{3-10}$ cycloalkyl, or $C_{1-6}$ alkyl; said alkyl, cycloalkyl, heterocyclyl and aryl optionally substituted with 1 to 3 groups of $R^a$, wherein n=0 or 1.

3. The compound according to claim 1 wherein the alkyl, aryl and heterocyclyl of $R^3$ and $R^4$ are selected from the group consisting of methyl, ethyl, propy, butyl, cyclobutyl, cyclopropyl, cyclopentyl, or cyclohexyl, phenyl, piperonyl, indolyl, pyridyl, imidazolyl, pyrimidinly, quinolinyl, isoquinolinyl, pyranoyl, or naphthyl, all optionally substituted with 1 to 3 groups of $R^a$.

4. A compound represented by structural formula Ic:

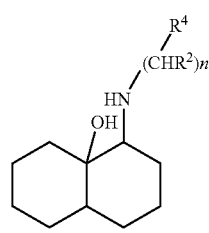

Ic or a pharmaceutically acceptable salt thereof, a solvate, hydrate, stereoisomer, or enantiomer of the compound or its salt wherein:
$R^2$ represents hydrogen, or $C_{1-6}$ alkyl;
$R^a$ represents $C_{1-6}$ alkyl, halogen, hydroxyl, $OR^2$, $(CH_2)_n CF_3$, $C_{3-6}$ cycloalkyl, $C(O)N(R^2)_2$, $C(R^2)_2 OR^2$, $C(O)R^2$, $NO_2$, CN, $N(R^2)_2$, $C(O)OR^2$, $(CH_2)_n C_{5-10}$ heterocyclyl, or $(CH_2)_n C_{6-10}$ aryl, said heterocyclyl and aryl optionally substituted with 1 to 3 groups of $C_{1-6}$ alkyl, halogen, hydroxyl, $(CH_2)_n CF_3$, or CN;
n represents 0 to 4;
$R^4$ is selected from the group consisting of $(CHR^2)_n C_{5-10}$ heterocyclyl, $(CHR^2)_n C_{6-10}$ aryl, $(CHR^2)_n C_{3-10}$ cycloalkyl, or $C_{1-6}$ alkyl; said alkyl, cycloalkyl, heterocyclyl and aryl optionally substituted with 1 to 3 groups of $R^a$.

5. The compound according to claim 4 wherein the alkyl of $R^4$ is methyl, ethyl, propy, or butyl optionally substituted with 1 to 3 groups of $R^a$; the cycloalkyl of $R^4$ is selected from the group consisting of cyclobutyl, cyclopropyl, cyclopentyl, and cyclohexyl, all optionally substituted with 1 to 3 groups of $R^a$ and n=0 or 1.

6. The compound according to claim 4 wherein the aryl and heterocyclyl of $R^4$ is selected from the group consisting optionally substituted piperonyl, indolyl, pyridyl, imidazolyl, pyrimidinly, quinolinyl, isoquinolinyl, pyranoyl, or naphthyl, and n=0 or 1.

7. The compound according to claim 1 represented by structural formula Ia:

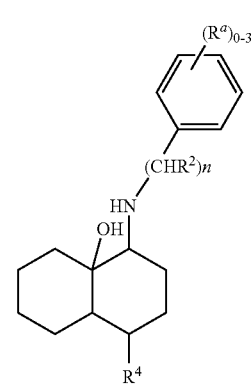

Ia or a pharmaceutically acceptable salt thereof, a solvate, hydrate, stereoisomer, or enantiomer, of the compound or its salt,
wherein $R^4$ is H, $R^a$ is selected from the group consisting of $C_{1-6}$ alkyl, halogen, CN, $OR^2$, $(CH_2)_n CF_3$, $C_{3-6}$ cycloalkyl, $(CH_2)_n C_{5-10}$ heterocyclyl, or $(CH_2)_n C_{6-10}$ aryl, said heterocyclyl and aryl optionally substituted with 1 to 3 groups of $C_{1-6}$ alkyl, halogen, hydroxyl, $(CH_2)_n CF_3$, or CN and n=0 or 1.

8. The compound according to claim 7 represented by structural formulas Ib:

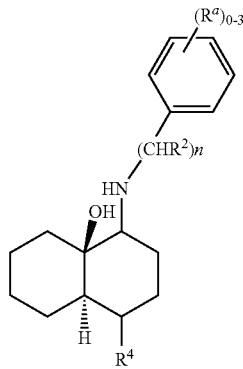

or a pharmaceutically acceptable salt thereof, or a solvate, hydrate, stereoisomer, or enantiomer thereof.

9. A compound which is:
(4aR,8aR)-4-[(4-fluorophenyl)amino]octahydronaphthalen-4a(2H)-ol,
(4aR,8aR)-4-[(3,4-difluorophenyl)amino]octahydronaphthalen-4a(2H)-ol,
(4aR,8aR)-4-(cyclopropylamino)octahydronaphthalen-4a(2H)-ol,
(4aR,8aR)-4-(propan-2-ylamino)octahydronaphthalen-4a(2H)-ol,
(4aR,8aR)-4-[(2,4,6-trifluorophenyl)amino]octahydronaphthalen-4a(2H)-ol,
(4aR,8aR)-4-[(2,4,5-trifluorophenyl)amino]octahydronaphthalen-4a(2H)-ol,
(4aR,8aR)-4-[(3,4,5-trifluorophenyl)amino]octahydronaphthalen-4a(2H)-ol,
(4aR,8aR)-4-[(2,3,5-trifluorophenyl)amino]octahydronaphthalen-4a(2H)-ol,
(4aR,8aR)-4-[(2,3,4-trifluorophenyl)amino]octahydronaphthalen-4a(2H)-ol,
(4aR,8aR)-4-[(3,5-difluorophenyl)amino]octahydronaphthalen-4a(2H)-ol,
(4aR,8aR)-4-[(3,4-difluorophenyl)amino]octahydronaphthalen-4a(2H)-ol,
(4aR,8aR)-4-[(2,6-difluorophenyl)amino]octahydronaphthalen-4a(2H)-ol,
(4aR,8aR)-4-[(2,5-difluorophenyl)amino]octahydronaphthalen-4a(2H)-ol,
(4aR,8aR)-4-[(2,3-difluorophenyl)amino]octahydronaphthalen-4a(2H)-ol,
(4aR,8aR)-4-[(4-fluorophenyl)amino]octahydronaphthalen-4a(2H)-ol,
(4aR,8aR)-4-[(3-fluorophenyl)amino]octahydronaphthalen-4a(2H)-ol,
(4aR,8aR)-4-[(2-fluorophenyl)amino]octahydronaphthalen-4a(2H)-ol,
(4aR,8aR)-4-{[4-(1H-tetrazol-5-yl)phenyl]amino}octahydronaphthalen-4a(2H)-ol,
(4aR,8aR)-4-{[3-(1H-tetrazol-5-yl)phenyl]amino}octahydronaphthalen-4a(2H)-ol,
(4aR,8aR)-4-{[2-(1H-tetrazol-5-yl)phenyl]amino}octahydronaphthalen-4a(2H)-ol,
4-(phenylamino)octahydronaphthalen-4a(2H)-ol,
4-(phenylamino)octahydronaphthalen-4a(2H)-ol,
(4aR,8aR)-4-(1H-indol-7-ylamino)octahydronaphthalen-4a(2H)-ol,
(4aR,8aR)-4-(biphenyl-4-ylamino)octahydronaphthalen-4a(2H)-ol,
(4aR,8aR)-4-(biphenyl-3-ylamino)octahydronaphthalen-4a(2H)-ol,
ethyl 3-{[(4aR,8aR)-8a-hydroxydecahydronaphthalen-1-yl]amino}-1H-indole-2-carboxylate,
(4aR,8aR)-4-(1H-indol-4-ylamino)octahydronaphthalen-4a(2H)-ol,
(4aR,8aR)-4-(quinolin-8-ylamino)octahydronaphthalen-4a(2H)-ol,
(4aR,8aR)-4-(isoquinolin-5-ylamino)octahydronaphthalen-4a(2H)-ol,
(4aR,8aR)-4-(quinolin-5-ylamino)octahydronaphthalen-4a(2H)-ol,
(4aR,8aR)-4-(isoquinolin-1-ylamino)octahydronaphthalen-4a(2H)-ol,
(4aR,8aR)-4-(quinolin-2-ylamino)octahydronaphthalen-4a(2H)-ol,
(4aR,8aR)-4-(quinolin-6-ylamino)octahydronaphthalen-4a(2H)-ol,
(4aR,8aR)-4-(quinolin-3-ylamino)octahydronaphthalen-4a(2H)-ol,
(4aR,8aR)-4-(isoquinolin-3-ylamino)octahydronaphthalen-4a(2H)-ol,
(4aR,8aR)-4-(naphthalen-2-ylamino)octahydronaphthalen-4a(2H)-ol,
(4aR,8aR)-4-(naphthalen-1-ylamino)octahydronaphthalen-4a(2H)-ol,
(4aR,8aR)-4-(biphenyl-2-ylamino)octahydronaphthalen-4a(2H)-ol,
(4aS,8aR)-4-(morpholin-4-yl)octahydronaphthalen-4a(2H)-ol,
(4S,4aS,8aR)-4-{[2-(1H-indol-3-yl)ethyl]amino}octahydronaphthalen-4a(2H)-ol,
(4R,4aS,8aR)-4-{[2-(1H-indol-3-yl)ethyl]amino}octahydronaphthalen-4a(2H)-ol,
(4S,4aS,8aR)-4-[(2-phenylethyl)amino]octahydronaphthalen-4a(2H)-ol,
(4R,4aS,8aR)-4-[(2-phenylethyl)amino]octahydronaphthalen-4a(2H)-ol,
(4R,4aS,8aR)-4-[(1,3-benzodioxol-5-ylmethyl)amino]octahydronaphthalen-4a(2H)-ol,
(4S,4aS,8aR)-4-[(1,3-benzodioxol-5-ylmethyl)amino]octahydronaphthalen-4a(2H)-ol,
(1R,4aR,8aS)-8a-hydroxy-N-(1-phenylethyl)decahydronaphthalen-1-aminium,
(1S,4aR,8aS)-8a-hydroxy-N-(1-phenylethyl)decahydronaphthalen-1-aminium,
(1R,4aR,8aS)-N-benzyl-8a-hydroxydecahydronaphthalen-1-aminium,
(1S,4aR,8aS)-N-benzyl-8a-hydroxydecahydronaphthalen-1-aminium,
(4aS,8aR)-4-(3,4-dihydroisoquinolin-2(1H)-yl)octahydronaphthalen-4a(2H)-ol,
(4aS,8aR)-4-(pyridin-3-ylamino)octahydronaphthalen-4a(2H)-ol,
(4R,4aS,8aR)-4-(1,3-benzodioxol-5-ylamino)octahydronaphthalen-4a(2H)-ol,
(4S,4aS,8aR)-4-(1,3-benzodioxol-5-ylamino)octahydronaphthalen-4a(2H)-ol,
(4R,4aS,8aR)-4-[(4-methylphenyl)amino]octahydronaphthalen-4a(2H)-ol,
(4S,4aS,8aR)-4-[(4-methylphenyl)amino]octahydronaphthalen-4a(2H)-ol,
(4R,4aS,8aR)-4-[(3-chlorophenyl)amino]octahydronaphthalen-4a(2H)-ol, (4S,4aS,8aR)-4-[(3-chlorophenyl)amino]octahydronaphthalen-4a(2H)-ol,
(4aS,8aR)-4-[(2-chlorophenyl)amino]octahydronaphthalen-4a(2H)-ol,
(4R,4aS,8aR)-4-[(4-methoxyphenyl)amino]octahydronaphthalen-4a(2H)-ol,
(4S,4aS,8aR)-4-[(4-methoxyphenyl)amino]octahydronaphthalen-4a(2H)-ol,
(4R,4aS,8aR)-4-[(3-methoxyphenyl)amino]octahydronaphthalen-4a(2H)-ol,
(4S,4aS,8aR)-4-[(3-methoxyphenyl)amino]octahydronaphthalen-4a(2H)-ol,
(4R,4aS,8aR)-4-[(2-methoxyphenyl)amino]octahydronaphthalen-4a(2H)-ol,
(4S,4aS,8aR)-4-[(2-methoxyphenyl)amino]octahydronaphthalen-4a(2H)-ol,
4-{[(1R,4aR,8aS)-8a-hydroxydecahydronaphthalen-1-yl]amino}benzonitrile,
4-{[(1S,4aR,8aS)-8a-hydroxydecahydronaphthalen-1-yl]amino}benzonitrile,
3-{[(1R,4aR,8aS)-8a-hydroxydecahydronaphthalen-1-yl]amino}benzonitrile,
3-{[(1S,4aR,8aS)-8a-hydroxydecahydronaphthalen-1-yl]amino}benzonitrile,
(4R,4aS,8aR)-4-(phenylamino)octahydronaphthalen-4a(2H)-ol,
(4S,4aS,8aR)-4-(phenylamino)octahydronaphthalen-4a(2H)-ol,
(4aR,8aR)-4-(2,3-dihydro-1H-inden-2-ylamino)octahydronaphthalen-4a(2H)-ol,
(4aR,8aR)-4-(2,3-dihydro-1H-inden-1-ylamino)octahydronaphthalen-4a(2H)-ol,
(4aR,8aR)-4-[(2,5-difluorophenyl)amino]octahydronaphthalen-4a(2H)-ol,
(4aR,8aR)-4-[(2-methylpropyl)amino]octahydronaphthalen-4a(2H)-ol,
(4aR,8aR)-4-(1H-indol-5-ylamino)octahydronaphthalen-4a(2H)-ol,
(4aR,8aR)-4-(pyridin-4-ylamino)octahydronaphthalen-4a(2H)-ol,
(4S,4aR,8aR)-4-(tetrahydro-2H-pyran-4-ylamino)octahydronaphthalen-4a(2H)-ol,
(4R,4aR,8aR)-4-(tetrahydro-2H-pyran-4-ylamino)octahydronaphthalen-4a(2H)-ol,
(4aR,8aR)-4-(cyclopentylamino)octahydronaphthalen-4a(2H)-ol,
(4aR,8aR)-4-(1,2,3,4-tetrahydronaphthalen-1-ylamino)octahydronaphthalen-4a(2H)ol,
(4aR,8aR)-4-{[(1S,2R)-2-hydroxycyclohexyl]amino}octahydronaphthalen-4a(2H)-ol,
(4aR,8aR)-4-[(pyrimidin-5-ylmethyl)amino]octahydronaphthalen-4a(2H)-ol,
(4aR,8aR)-4-(tetrahydro-2H-pyran-3-ylamino)octahydronaphthalen-4a(2H)-ol,
(4aR,8aR)-4-[(2,2,2-trifluoroethyl)amino]octahydronaphthalen-4a(2H)-ol,
(4aR,8aR)-4-[(2-methylcyclohexyl)amino]octahydronaphthalen-4a(2H)-ol,
(4aR,8aR)-4-[(2-methoxyethyl)amino]octahydronaphthalen-4a(2H)-ol,
(4aR,8aR)-4-[(3S,5S,7S)-tricyclo[3.3.1.1$^{3,7}$]dec-1-ylamino]octahydro-naphthalen-4a(2H)-ol,
(4aR,8aR)-4-(2,3-dihydro-1H-inden-2-ylamino)octahydronaphthalen-4a(2H)-ol,
(4aR,8aR)-4-(morpholin-4-yl)octahydronaphthalen-4a(2H)-ol,
(4aR,8aR)-4-{[2-(1H-indol-3-yl)ethyl]amino}octahydronaphthalen-4a(2H)-ol,
(4aR,8aR)-4-[(2-phenylethyl)amino]octahydronaphthalen-4a(2H)-ol,
(4aR,8aR)-4-[(1,3-benzodioxol-5-ylmethyl)amino]octahydronaphthalen-4a(2H)-ol,
(4aR,8aR)-4-[(1-phenylethyl)amino]octahydronaphthalen-4a(2H)-ol,
(4aR,8aR)-4-(benzylamino)octahydronaphthalen-4a(2H)-ol,
(4aR,8aR)-4-(3,4-dihydroisoquinolin-2(1H)-yl)octahydronaphthalen-4a(2H)-ol,
(4aR,8aR)-4-(pyridin-3-ylamino)octahydronaphthalen-4a(2H)-ol,
(4aR,8aR)-4-(1,3-benzodioxol-5-ylamino)octahydronaphthalen-4a(2H)-ol,
(4aR,8aR)-4-[(4-methylphenyl)amino]octahydronaphthalen-4a(2H)-ol,
(4aR,8aR)-4-[(3-chlorophenyl)amino]octahydronaphthalen-4a(2H)-ol,
(4aR,8aR)-4-[(3-chlorophenyl)amino]octahydronaphthalen-4a(2H)-ol,
(4aR,8aR)-4-[(4-methoxyphenyl)amino]octahydronaphthalen-4a(2H)-ol,
(4aR,8aR)-4-[(3-methoxyphenyl)amino]octahydronaphthalen-4a(2H)-ol,
(4aR,8aR)-4-[(2-methoxyphenyl)amino]octahydronaphthalen-4a(2H)-ol,
4-{[(4aR,8aR)-8a-hydroxydecahydronaphthalen-1-yl]amino}benzonitrile,
3-{[(4aR,8aR)-8a-hydroxydecahydronaphthalen-1-yl]amino}benzonitrile,
2-{[(4aR,8aR)-8a-hydroxydecahydronaphthalen-1-yl]amino}benzonitrile,
4-(phenylamino)octahydronaphthalen-4a(2H)-ol,
or a pharmaceutically acceptable salt thereof, or a solvate, hydrate, stereoisomer, or enantiomer of the compound or its salt.

10. The compound according to claim 5 which is (4aR,8aR)-4-[(4-fluorophenyl)amino]octahydronaphthalen-4a(2H)-ol, or a pharmaceutically acceptable salt thereof, or a solvate, hydrate, stereoisomer, or enantiomer of the compound or its salt.

11. The compound according to claim 5 which is (4R,4aR,8aR)-4-(phenylamino)octahydronaphthalen-4a(2H)-ol, or a pharmaceutically acceptable salt thereof, or a solvate, hydrate, stereoisomer, or enantiomer of the compound or its salt.

12. A pharmaceutical composition comprising a compound according to claim 1 and a pharmaceutically acceptable carrier.

\* \* \* \* \*